United States Patent
Van Heerden et al.

(10) Patent No.: US 6,376,657 B1
(45) Date of Patent: Apr. 23, 2002

(54) PHARMACEUTICAL COMPOSITIONS HAVING APPETITE SUPPRESSANT ACTIVITY

(75) Inventors: Fanie Retief Van Heerden, Fairland; Robert Vleggaar, Pretoria; Roelof Marthinus Horak, Pretoria; Robin Alec Learmonth, Pretoria; Vinesh Maharaj, Pretoria; Rory Desmond Whittal, Pretoria, all of (ZA)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 09/402,962

(22) PCT Filed: Apr. 15, 1998

(86) PCT No.: PCT/GB98/01100

§ 371 Date: Oct. 13, 1999

§ 102(e) Date: Oct. 13, 1999

(87) PCT Pub. No.: WO98/34624

PCT Pub. Date: Oct. 22, 1998

(30) Foreign Application Priority Data

Apr. 15, 1997 (ZA) .................................................. 97/3201

(51) Int. Cl.[7] ...................... A61K 39/385; A61K 31/44; C07J 5/00
(52) U.S. Cl. ................ 536/5; 424/195.1; 514/278; 514/221; 514/90; 514/303; 514/326
(58) Field of Search .................... 536/5; 424/195.1; 514/278, 221, 90, 303, 326

(56) References Cited

U.S. PATENT DOCUMENTS

PP4,199 P    1/1978   Cobia et al.

(List continued on next page.)

FOREIGN PATENT DOCUMENTS

| EP | 0 101 383 A1 | 2/1984 |
|----|-------------|--------|
| WO | WO 97/47316 | 12/1997 |
| WO | WO 98/10068 | 3/1998 |
| WO | WO 98/27113 | 6/1998 |
| WO | WO 98/28335 | 7/1998 |

OTHER PUBLICATIONS

E. Borowski et al., "Chemical Studies on Amphotericin B II. 2-Methylheptadecanedioic Acid From Perhydrogenated Amphotericin B", *Tetrahedron Letters*, No. 9, pp. 473–478, 1965.

(List continued on next page.)

*Primary Examiner*—Ralph Gitomer
*Assistant Examiner*—Devesh Khare
(74) *Attorney, Agent, or Firm*—Morgan, Lewis & Bockius LLP

(57) ABSTRACT

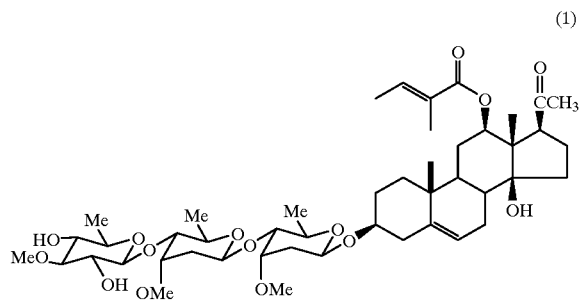

A pharmaceutical composition which contains an extract obtainable from a plant of the genus Trichocaulon or Hoodia containing an appetite suppressant agent having the formula (1). A process for obtaining the extract and a process for synthesizing compound (1) and its analogues and derivatives is also provided. The invention also extends to the use of such extracts and compound (1) and its analogues for the manufacture of medicaments having appetite suppressant activity. The invention further provides novel intermediates for the synthesis of compound (1).

58 Claims, 6 Drawing Sheets

U.S. PATENT DOCUMENTS

| | | |
|---|---|---|
| 4,185,116 A | 1/1980 | Barnish et al. |
| 4,302,447 A | 11/1981 | Horrobin |
| 4,302,477 A | 11/1981 | Mendy et al. |
| 4,393,049 A | 7/1983 | Horrobin |
| 4,584,289 A | 4/1986 | Jarreau et al. ............... 514/182 |
| 4,882,315 A | 11/1989 | Chiodini et al. |
| 4,931,463 A | 6/1990 | Barbier et al. |
| 5,175,186 A | 12/1992 | Barbier et al. |
| 5,246,960 A | 9/1993 | Barbier et al. |
| 5,364,636 A | 11/1994 | Ochi |
| 5,516,516 A | 5/1996 | Cherksey |
| 5,605,698 A | 2/1997 | Ueno |
| 5,693,327 A | 12/1997 | Shah |
| 5,698,199 A | 12/1997 | Mori et al. |
| 5,798,101 A | 8/1998 | Haveson |
| 5,824,668 A | 10/1998 | Rubinfeld et al. |
| 5,908,609 A | 6/1999 | Lee et al. ..................... 424/9.2 |
| 6,100,048 A | 8/2000 | Cone et al. ................ 435/7.21 |

OTHER PUBLICATIONS

Bando H et al., "Constituents of Asclepiacaceae plants. XXXI. Component of *Stapelia grandiflora* MASS", Chemical and Pharmaceutical Bulletin. 1974; 22(5):1209–1211.

Bruyns P, "A revision of Hoodia and Lavrania (Asclepiadaceae—Stapelieae)", Botanische Jahrbucher Fur Systematik Pflanzengeschichte Und Pflanzengeographie. 1993; 115(2):145–270.

Bruyns P, "New combinations in Hoodia and Lavrania (Asclepiadaceae—Stapelieae)", South African Journal of Botany. 1993; 59(3):342.

Chen et al., "A novel C–21 steroidal glycoside from *Marsdenia incisa*", Chemical Abstracts. 1991. Dec. 23; 115(25):591. Abstract No. 275751.

Chen SW et al., "The hyperphagic effect of 3 alpha–hydroxylated pregnane steroids in male rats", Pharmacol Biochem Behav. Apr. 1996; 53(4):777–782.

Coombes AJ, 1985, *Dictionary of Plant Names,* Timber Press Inc., Portland, Oregon, p. 31.

De Rick A and Belpaire F, "Digoxin–quinidine interaction in the dog", J Vet Pharmacol Ther. Sep. 1981; 4(3):215–218.

Deepak D et al., "A new pregnane glycoside from *Periploca calophylla*", Indian Journal of Chemistry, Section B. Jan. 1986; 25b(1):44–45.

Dolle RE and Nicolaou KC, "Total synthesis of elfamycins: aurodox and efrotomycin. 1. Strategy and construction of key intermediates", J Am Chem Soc. Mar. 20, 1985; 107(6):1691–1694.

Dolle RE and Nicolaou KC, "Total synthesis of elfamycins: aurodox and efrotomycin. 2. Coupling of key intermediates and completion of the synthesis", J Am Chem Soc. Mar. 20, 1985; 107(6):1695–1698.

Douketis JD et al., "Periodic health examination, 1999 update: 1. Detection, prevention and treatment of obesity", Canadian Medical Association Journal, Feb. 23, 1999; 160:513–525.

Fan W et al., "Role of melanocortinergic neurons in feeding and the agouti obesity syndrome", Nature. Jan. 9, 1997; 385(6612):165–168.

Foster S and Duke JA, 1990, *A Fiueld Guide to Medicinal Plants, Eastern and Central North American,* Houghton Mifflin Company, Boston, pp. 136, 154.

Glendinning JI, "Effectiveness of cardenolides as feeding deterrents to Peromyscus mice", Journal of Chemical Ecology. 1982. 18(9):1559–1575. Chemical Abstracts. Dec. 12, 1992; 117(25):463. Abstract No.: 249115.

Habermehl G et al., "Rearrangement of 14β–hydroxy–12β–sulfoxy–steroids to 13,17–seco–12, 17–cyclo–steroids; a 2D–NMR analysis", Z Naturforsch. May 1985; 40b(5):656–660.

Haskell–Luevano C et al., "Discovery of prototype peptidomimetic agonists at the human melanocortin receptors MC1R and MC4R", J Med Chem. Jul. 4, 1997;40(14):2133–2139.

Hayashi K et al., "Four pregnane glycosides, boucerosides AI, AII, BI and BII, from *Boucerosia aucheriana*", Phytochemistry. 1988; 27(12):3919–3924.

Heller M et al., "Electrophilic addition to the delta–14 double bond of a steroid", Steroids. Feb. 1964; 3(2):193–201.

Hill BCF, "Hoodia Gordonii", Nat. Cact. and Succ. Journal, Sep. 1969; 24(3):69–70.

Huszar D et al., "Targeted disruption of the melanocortin–4 receptor results in obesity in mice", Cell. Jan. 10, 1997;88(1):131–141.

Kopelman P, "Prescribing for obesity", Journal of the Royal College of Physicians of London, Jan./Feb 1999; 33(1):31–32.

Millspaugh CF, 1974, *American Medicinal Plants,* Dover Publications, Inc., New York, pp. 534–543.

Mitsuhashi H et al., "Studies on the constituents of Asclepiadaceae plants. XIII. Epimerization at C–17 and optical rotatory dispersion Study of C/D cis pregnane–2–one derivatives", Steroids. 1964; 4(4):483–493.

Mitsuhashi H and Nomura T, "Constituents of Asclepiadaceae plants. XVI. Components of Metaplexis japonica", Chem Pharm Bull. 1965. 13(11):1332–1340. Chemical Abstracts. Nov. 7, 1966; 65(10) Abstract No. 15447d.

Mitsuhashi H and Mizuta H, "Constituents of Asclepiadaceae plants. XXV. Components of *Cynanchum boerhavifolium*", Yakugaku Zasshi. 1969. 89(10):1352–1357. Chemical Abstracts. Feb. 16, 1970; 72(7):53. Abstract No. 028873.

Miwa H et al., "Structural determinants of the melanocortin peptides required for activation of melanocortin–3 and melanocortin–4 receptors", J Pharmacol Exp Ther. Apr. 1995; 273(1):367–372.

Nikaido et al., "Components of *Boucherosia aucheriana* DECNE", Chemical and Pharmaceutical Bulletin. 1967; 15(5):725–726.

Oki et al., "Intramolecular interaction between hydroxyl group and carbonyl moiety in keto–alcohols", Bulletin of the Chemical Society of Japan. Jan. 1968; 41(1):176–182.

Swarupanandan K et al., "The subfamilial and tribal classification of the family Asclepiadaceae", Botanical Journal of the Linnaean Society. 1996; 120;327–369.

Tanaka T et al., "Studies on the constitutuents of Asclepiadaceae plants. Part 71. Pregnane glycosides from *Boucerosia aucheriana*", Phytochemistry. 1990; 29(1):229–237.

Templeton JF et al., "Progesterone derivatives that bind to the digitalis receptor: synthesis of 14 beta–hydroxyprogesterone. A novel steroid with positive inotropic activity", J Med Chem. Aug. 1987; 30(8):1502–1505.

Trivedi R et al., "A pregnane ester oligoglycoside from Oxystelma Esculentum", Phytochemistry. 1989; 28(4):1211–1213.

Tschesche R and Grimmer G, "Uber pflanzliche Herzgifte, XXX. Mitteil.: Neue Glykoside aus den Blattern von *Digitalis purpurea* und *Digitalis lanata*", Chemische Berichte. 1955; 88(10):1569–1576.

Tschesche R et al., "Uber Digitanolglykoside—XI (1) Zur Konstitiution des Digipupuogenin", Tetrahedron Letters. 1964; 9:473–480.

Tschesche R and Schwinum E, "Uber digitanolglykoside, 15. Synthese von 12α.20R–epoxy–5α. 14β.17βH–pregnanen", Chemische Berichte. 1967; 100(2):464–479.

Warburg O, "Die Pflanzenwelt, Dritter Band", 1922, Bibliographisches Institut, Leipzig, p. 146, paragraph 7.

www4.torget.se/users/k/Kohleria/Engelska/ascltaxonomi.html Asclepiadaceae accessed Sep. 6, 1999.

www.graylab.ac.uk/usr/hodgkiss/aclass.html Succulent Asclepiad Genera accessed Sep. 6, 1999.

www.graylab.ac.uk/usr/hodgkiss/asclep.html The Asclepiad Page accessed Jun. 15, 1999.

www.graylab.ac.uk/usr/hodgkiss/iassale.html The International Asclepiad Society accessed Jun. 15, 1999.

Yoshii E et al., "Pregn–14–en–20–ones. Facile preparation and 14β–hydroxylation", Chem Pharm Bull. 1972. 20(8):1827–1829. Chemical Abstracts. Oct. 23; 77(17):477. Abstract No. 114653.

Yoshikawa K et al., "Steroidal glycosides from the fresh stem of *Stephanotis lutchuensis* var. *japonica* (Asclepiadaceae). Chemical structures of stephanosides A–J", Chem Pharm Bull (Tokyo). Dec. 1996; 44(12):1790–1796.

Yoshikawa K et al., "Steroidal glycosides from the fresh stem of *Stephanotis lutchuensis* var. *japonica* (Asclepiadaceae). Chemical structures of stephanosides K–Q", Chem Pharm Bull (Tokyo). Dec. 1996; 44(12):2243–2248.

Chen et al. "The hyperphagic effect of 3–alpha–hydroxylated pregnane steroids in male rats"., Pharmacology Biochemistry and Behavior, vol., 53, No.4, pp. 777–782, 1996.

Wada et al. "Studies on the constituents of Asclepiadaceae plants. L. Two new oligoglycosides, cynanchoside C2 and cynanchoside C1, from *Cynanchum caudatum* Max." Chem. Pharm. Sci., (1982), 30(10), 3500–4.

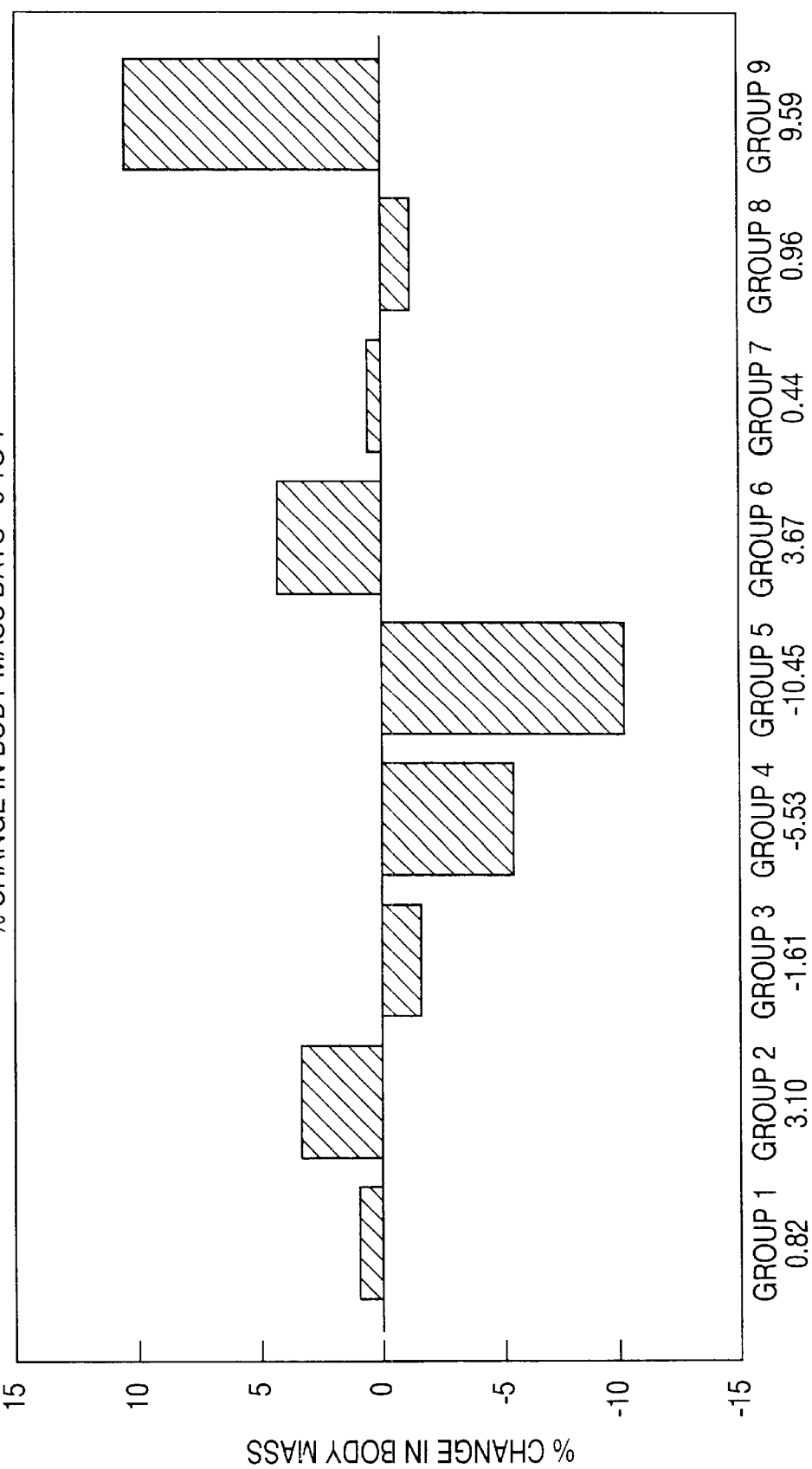

PHARMACEUTICAL COMPOSITIONS HAVING APPETITE SUPPRESSANT ACTIVITY

This application is the U.S. national phase of PCT International Application No. PCT/GB98/01100, filed Apr. 15, 1998, which claims priority to South African application No. 97/3201, filed Apr. 15, 1997.

THIS INVENTION relates to steroidal glycosides, to compositions containing such steroidal glycosides and to a new use for these steroidal glycosides and the compositions containing them. The invention further relates to a method of extracting and isolating these steroidal glycosides from plant material, to a method of synthetically producing these steroidal glycosides, and to the products of such an extraction and such a synthesis process.

In a particular application, the invention relates to an appetite suppressant agent, to a process for synthetically producing the appetite suppressant agent, to a process for extracting the appetite suppressant agent from plant material, to an appetite suppressant composition containing the appetite suppressant agent, and to a method of suppressing an appetite.

According to the invention, there is provided a process for preparing an extract of a plant of the genus Trichocaulon or of the genus Hoodia, the extract comprising an appetite suppressant agent, the process including the steps of treating collected plant material with a solvent to extract a fraction having appetite suppressant activity, separating the extraction solution from the rest of the plant material, removing the solvent from the extraction solution and recovering the extract. The extract so recovered may be further purified, eg by way of suitable solvent extraction procedures.

The invention also provides a plant extract made of plants of the group comprising the genus Trichocaulon and the genus Hoodia and having appetite suppressant activity.

The extract may be prepared from plant material such as the stems and roots of said plants of the genus Trichocaulon or of the genus. Hoodia. The genus Trichocaulon and the genus Hoodia include succulent plants growing in arid regions such as are found in Southern Africa. In one application of the invention, the active appetite suppressant extract is obtained from the species *Trichocaulon piliferum*. The species *Trichocaulon officinale* may also be used to provide an active appetite suppressant extract. In another application of the invention, the active appetite suppressant extract may be obtained from the species *Hoodia currorii*, *Hoodia gordonii* or *Hoodia lugardii*. Bioassays conducted by the Applicant on rats have indicated that certain of the extracts possess appetite suppressant activity.

The plant material may be homogenised in the presence of a suitable solvent, for example, a methanol/methylene chloride solvent, by means of a device such as a Waring blender. The extraction solution may then be separated from the residual plant material by an appropriate separation procedure such as, for example, filtration or centrifugation. The solvent may be removed by means of the rotary evaporator, preferably in a water bath at a temperature of 60° C. The separated crude extract may then be further extracted with methylene chloride and water before being separated into a methylene chloride extract and a water extract. The methylene chloride extract may have the solvent removed preferably by means of evaporation on a rotary evaporator and the resultant extract may be further purified by way of a methanol/hexane extraction. The methanol/hexane extraction product may then be separated to yield a methanol extract and a hexane extract. The methanol extract may be evaporated to remove the solvent in order to yield a partially purified active extract.

The partially purified active extract may be dissolved in methanol, and may be further fractionated by column chromatography, employing silica gel as an adsorption medium and a chloroform/30% methanol mixture as an eluent. A plurality of different fractions may be obtained, and each may be evaluated, by suitable bioassaying procedures, to determine the appetite suppressant activity thereof.

A fraction having appetite suppressant activity may preferably be further fractionated such as by column chromatography using silica gel as an adsorption medium and a 9:1 chloroform:methanol solvent, and the resultant sub-fractions bioassayed for their appetite suppressant activity. A sub-fraction displaying appetite suppressant activity may, if desired, be further fractionated and purified, conveniently using a column chromatographic procedure with silica gel as the adsorption medium and a 9:1 ethylacetate:hexane solvent. The resultant purified fractions may again be evaluated by suitable bioassay procedures for their appetite suppressant activity.

The Applicant has found that at least one such purified fraction has good appetite suppressant activity, and the active principle in the fraction was identified by conventional chemical techniques including nuclear magnetic resonance, and was found to be a compound of the structural formula

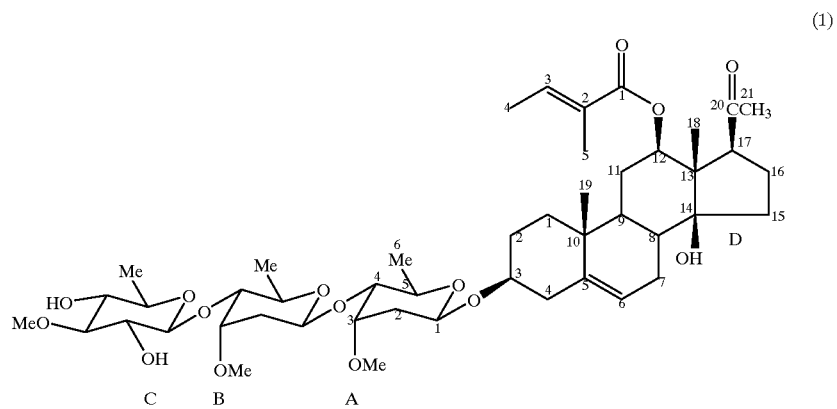

(1)

In accordance with S.I. nomenclature, the active principle (1) is the compound 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5β-en-20-one ($C_{47}H_{74}O_{15}$ $M^+878$).

According to another aspect of the invention, there is provided a process for preparing an extract of a plant of the genus Trichocaulon or of the genus Hoodia, the extract comprising an appetite suppressant agent, the process including the steps of pressing collected plant material to separate sap from solid plant material and recovering the sap free of the solid plant material to form the extract.

The extract may be dried to remove moisture, e.g. by spray-drying, freeze-drying or vacuum drying, to form a free-flowing powder.

The invention extends to a composition having appetite suppressant activity comprising an extract as described above.

The composition may be admixed with a pharmaceutical excipient, diluent or carrier and optionally it is prepared in unit dosage form.

The invention also extends to the use of an extract as described above in the manufacture of a medicament having appetite suppressant activity, to an extract as described above for use as a medicament having appetite suppressant activity, and to a method of suppressing an appetite by administering to a human or animal an effective dosage of a composition as described above.

Compound (1) is a novel compound and the invention extends to compound (1) and certain analogues or derivatives of this steroidal trisaccharide having appetite suppressant properties. The molecules chosen as the analogues or derivatives are intended to affect the properties of the steroidal trisaccharide with the aim of increasing the activity of the active ingredient. The following effects were taken into consideration when the analogues were chosen:

(i) Hydrophobic interactions and lipophilicity

Functional group modifications of the active molecule is intended to change the hydrophobicity and lipophilicity of the molecule. Increased lipophilicity has been shown to correlate with increased biological activity, poorer aqueous solubility, increased detergency/cell lysis, increased storage in tissues, more rapid metabolism and elimination, increased plasma protein binding and faster rate of onset of action.

(ii) Electronic properties and ionization constants

Functional group modification of the molecule is also intended to change the acidity and basicity which would have a major role in controlling the transport of the compound to its site of action and the binding at this target site.

(iii) Hydrogen bonding

Functional group modifications of carboxyl and carbonyl groups in the active molecule are intended to change the interactions between the proteins in biological systems and the chemically modified functional groups.

(iv) Steric parameters

The purpose of changing the steric features of the molecule is to increase binding to its receptor and thus increase its biological activity.

The following chemical modifications to the molecule are intended to affect the hydrophobicity and lipophilicity electronic properties, hydrogen bonding and steric parameters on the molecule:

a) Chemical modification of the C-12 group and ester functionality;
b) Chemical modification of the 5,6-double bond, e.g. hydrogenation and migration;
c) Chemical modification of the C-20 carbonyl and C-17 acetyl group;
d) Chemical modification of the "D" ring of the steroid or aglycone ring;
e) Modification of the carbohydrates of the trisaccharide moiety.

Accordingly, the invention provides a compound having the general structural formula

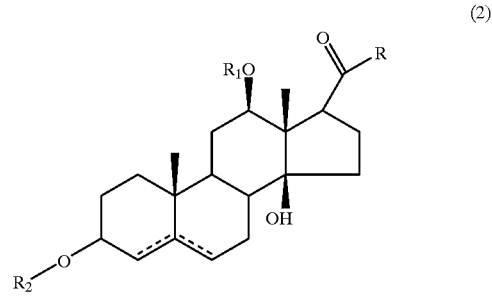

(2)

in which R=alkyl;

$R_1$=H, alkyl, tigloyl, benzoyl, or any other organic ester group;

$R_2$=H, or one or more 6-deoxy carbohydrates, or one or more 2,6-dideoxy carbohydrates, or glucose molecules, or combinations thereof;

and in which the broken lines indicate the optional presence of a further bond between C4–C5 or C5–C6.

The invention also provides a compound as described above wherein there is a further bond between C5–C6, R=methyl, $R_1$=tigloyl, $R_2$=3-O-[-β-D-thevetopyranosyl-(1→4)-β-D-cymaropyranosyl-(1→4)-β-D-cymaropyranosyl] and having the structural formula.

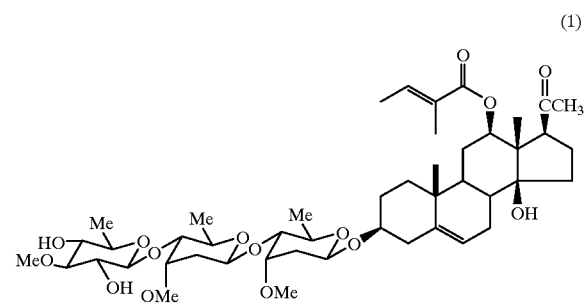

(1)

Further active analogues or derivatives of the appetite suppressant compound (1) in accordance with the invention are compounds having the following structural formulae:

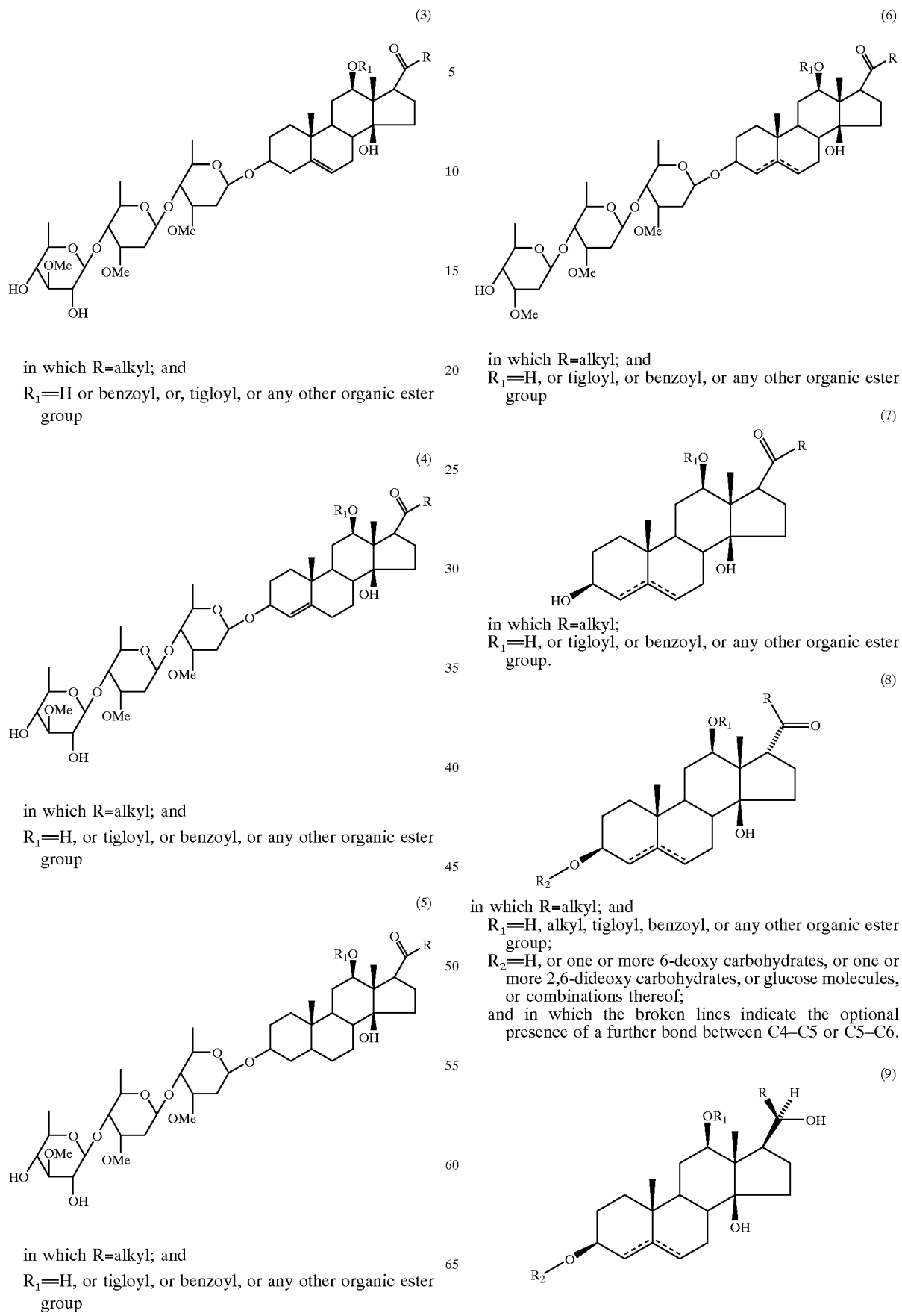

(3)

in which R=alkyl; and
R₁=H or benzoyl, or, tigloyl, or any other organic ester group (4)

in which R=alkyl; and
R₁=H, or tigloyl, or benzoyl, or any other organic ester group (5)

in which R=alkyl; and
R₁=H, or tigloyl, or benzoyl, or any other organic ester group (6)

in which R=alkyl; and
R₁=H, or tigloyl, or benzoyl, or any other organic ester group (7)

in which R=alkyl;
R₁=H, or tigloyl, or benzoyl, or any other organic ester group.

(8)

in which R=alkyl; and
R₁=H, alkyl, tigloyl, benzoyl, or any other organic ester group;
R₂=H, or one or more 6-deoxy carbohydrates, or one or more 2,6-dideoxy carbohydrates, or glucose molecules, or combinations thereof;
and in which the broken lines indicate the optional presence of a further bond between C4–C5 or C5–C6.

(9)

in which R=alkyl; and

R$_1$=H, alkyl, tigloyl, benzoyl, or any other organic ester group;

R$_2$=H, or one or more 6-deoxy carbohydrates, or one or more 2,6-dideoxy carbohydrates, or glucose molecules, or combinations thereof;

and in which the broken lines indicate the presence of a further bond between C4–C5 or C5–C6.

(10)

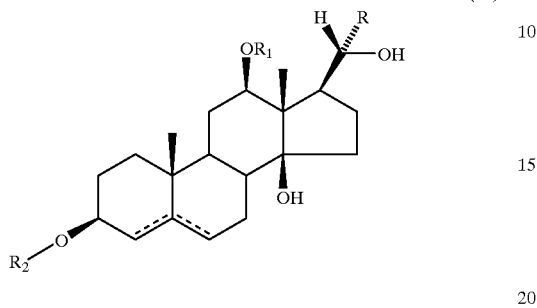

in which R=alkyl; and

R$_1$=H, alkyl, tigloyl, benzoyl, or any other organic ester group;

R$_2$=H, or one or more 6-deoxy carbohydrates, or one or more 2,6-dideoxy carbohydrates, or glucose molecules, or combinations thereof;

and in which the broken lines indicate the optional presence of a further bond between C4–C5 or C5–C6.

(11)

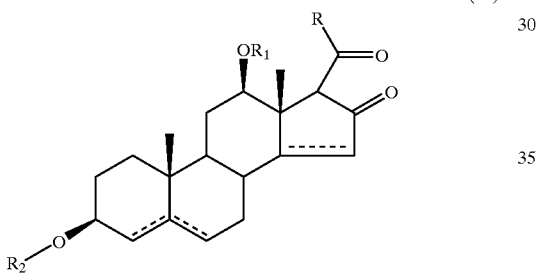

in which R=alkyl; and

R$_1$=H, alkyl, tigloyl, benzoyl, or any other organic ester group;

R$_2$=H, or one or more 6-deoxy carbohydrates, or one or more 2,6-dideoxy carbohydrates, or glucose molecules, or combinations thereof;

and in which the broken lines indicate the optional presence of a further bond between C4–C5, C5–C6 or C14–C15.

(52)

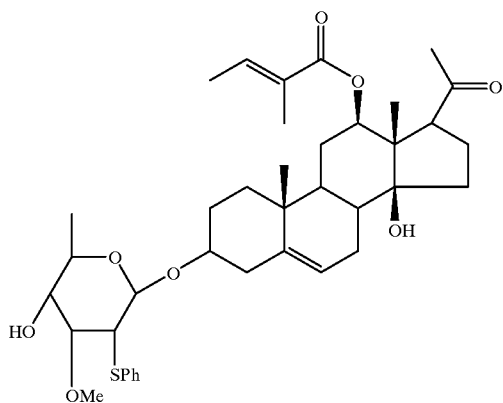

in which R=alkyl; and

R$_1$=H, alkyl, tigloyl, benzoyl, any other organic ester group;

R$_2$=H, or one or more 6-deoxy carbohydrates, or one or more 2,6-dideoxy carbohydrates, or glucose molecules, or combinations thereof;

and in which the broken lines indicate the optional presence of a further bond between C4–C5, C5–C6 or C14–C15.

(13)

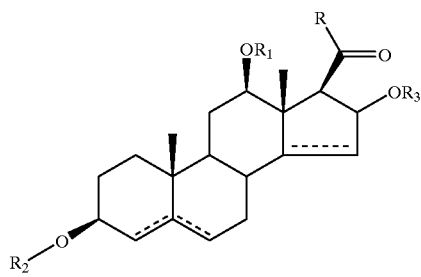

in which R=alkyl; and

R$_1$=H, alkyl, tigloyl, benzoyl, any other organic ester group;

R$_2$=H, or one or more 6-deoxy carbohydrates, or one or more 2,6-dideoxy carbohydrates, or glucose molecules, or combinations thereof;

and in which the broken lines indicate the optional presence of a further bond between C4–C5, C5–C6 or C14–C15; and R$_3$=H, alkyl, aryl, acyl, or glucoxy.

(14)

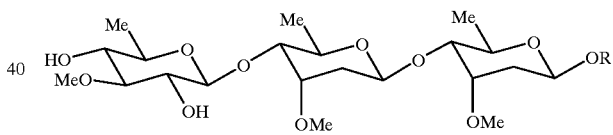

in which R=H, alkyl, aryl or any steroid possessing a C14 beta hydroxy group, or a C12 beta hydroxy functionality, or a C17 acyl group, or a C5–C6 olefin, or combinations thereof.

The invention still further extends to a process for synthetically producing a compound having appetite suppressant activity.

The process uses a steroid as a starting material (or intermediate or precursor), the steroid having the chemical formula (15)

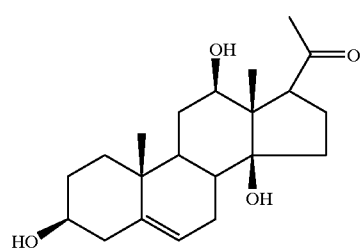

The steroid (15) can be prepared from a compound having the formula (22) by a process which includes the steps of
(i) treating progesterone having the formula (16)

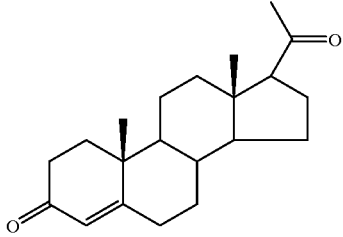

with the micro-organism *Calonectria decora* to produce a compound 12β, 15α-dihydroxy progesterone of the formula (17)

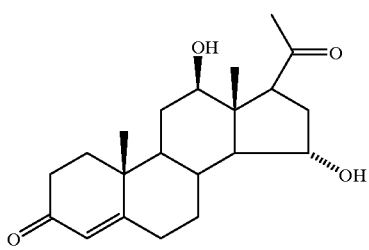

(ii) treating compound (17) with tosyl chloride and pyridine to produce a compound 12β-hydroxy-15α-(p-toluene sulfonyl)-progesterone of the formula (18)

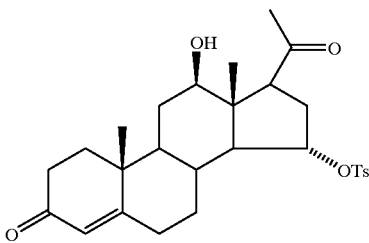

(iii) treating the compound (18) with collidine at 150° C. to produce a compound 12β-hydroxy-$\Delta^4$-progesterone of the formula (19)

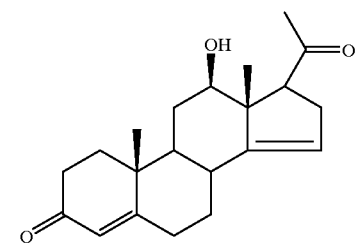

(iv) treating the compound (19) with acetyl chloride and acetic anhydride at 120° C., to produce a compound 3,12β-diacetoxypregna-3,5,14-trien-20-one of the formula (20)

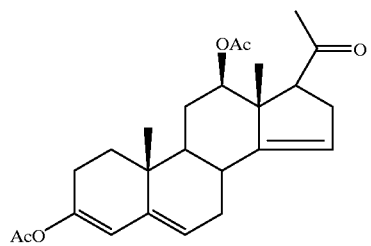

(v) treating the compound (20) with ethylene glycol and a catalytic amount of p-toluene sulphonic acid, to produce a compound 3,12β-diacetoxy-20,20-ethylenedioxypregna-3,5,14-triene of the formula (21)

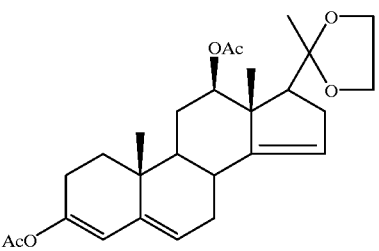

(vi) treating the compound (21) with $NaBH_4$ to produce a compound 3β, 12β-dihydroxy-20,20-ethylenedioxypregna-5,14-diene-12-acetate of the formula (22)

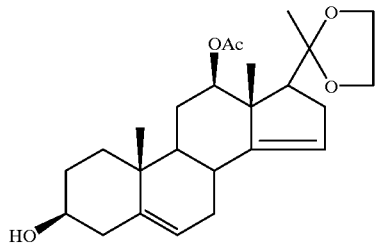

In a first alternative procedure, a process for the preparation of steroid (15) according to the invention includes the steps of (a) treating compound (22) with a reducing agent, e.g. $LiAlH_4$, to produce a compound 3β, 12β-dihydroxy-20,20-ethylenedioxypregna-5,14-diene of the formula (23)

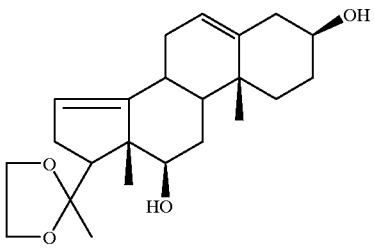

(b) treating compound (23) with N-bromoacetamnide (NBA) and a base, e.g. pyridine, to produce a compound 3β, 12β-dihydroxy-14,15-epoxy-20,20-ethylenedioxypregn-5-ene of the formula

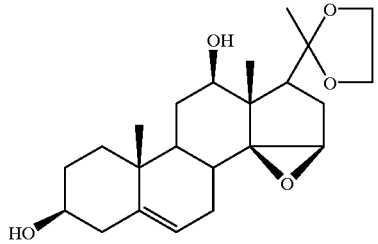

(24)

(c) treating compound (24) with a reducing agent, e.g. LiAlH$_4$, e.g. with refluxing, to produce a compound 3β, 12β, 14β-trihydroxy-20,20-ethylenedioxypregn-5-ene of the formula

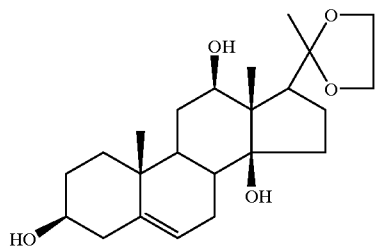

(25)

and (d) treating compound (25) with an acid, e.g. acetic acid, and water to produce the steroid intermediate compound 3β, 12β, 14β-trihydroxypregn-5-ene (15).

Reaction Scheme A depicts the procedure for the preparation of steroid intermediate (15) from compound (22) according to "the first alternative procedure" of the invention (and includes the preparation of compound (22) from compound (16) for illustrative purposes).

Reaction Scheme A

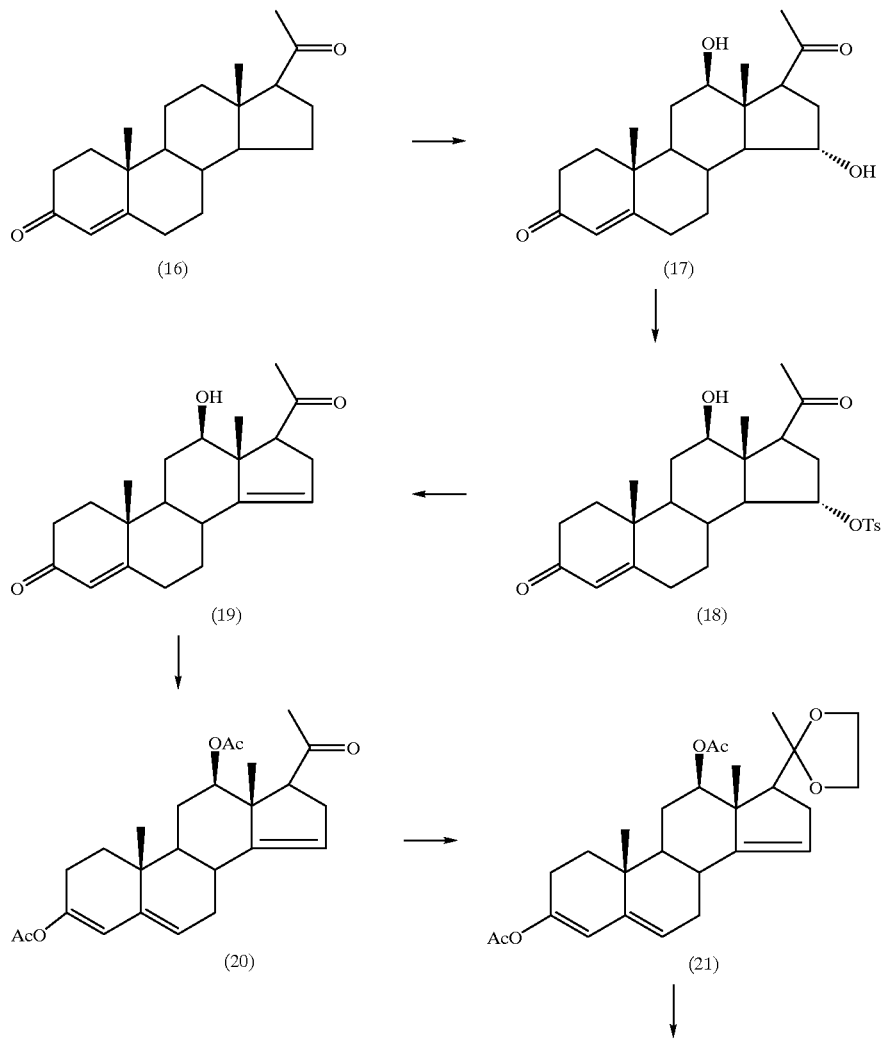

-continued

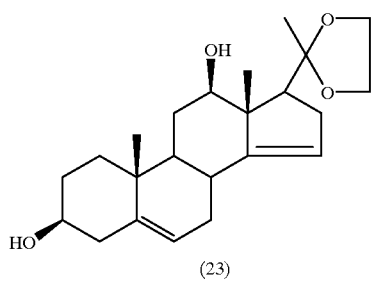
(23)

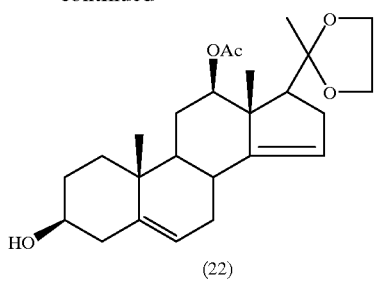
(22)

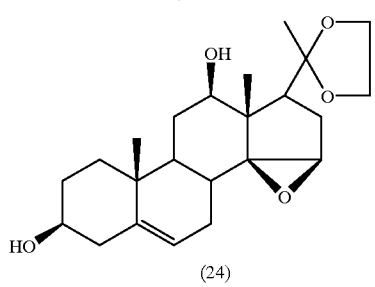
(24)

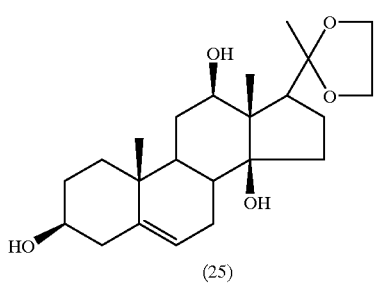
(25)

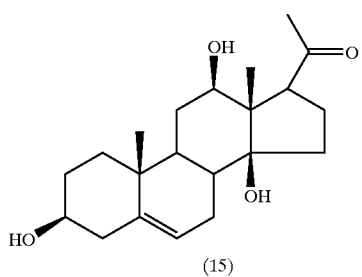
(15)

In a second alternative procedure, a process for the preparation of steroid (15) according to the invention includes the steps of (a) treating compound (22) (3β, 12β-dihydroxy-20,20-ethylenedioxypregna-5,14-diene-12-acetate) with p-toluenesulfonyl chloride and a base, e.g. pyridine, to produce a compound 3β, 12β-dihydroxy-20,20-ethylenedioxypregna-5,14-diene-3-tosyl-12-acetate of the formula (26)

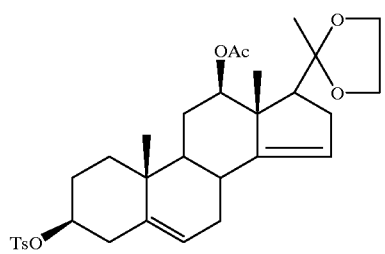

(b) treating compound (26) with potassium acetate in a solvent, e.g. acetone, to produce a compound 6β, 12β-dihydroxy-20,20-ethylenedioxy-3,5α-cyclopregnan-14-ene-12-acetate of the formula (27)

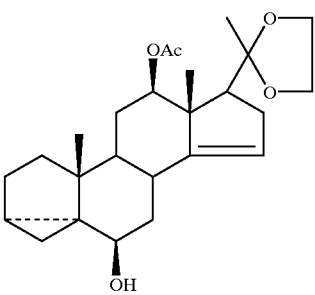

(c) treating the compound (27) with a reducing agent, e.g. LiAlH$_4$, and e.g. tetrahydrofuran, to produce a compound 6β, 12β-dihydroxy-20,20-ethylenedioxy-3,5α-cyclopregnan-14-ene of the formula

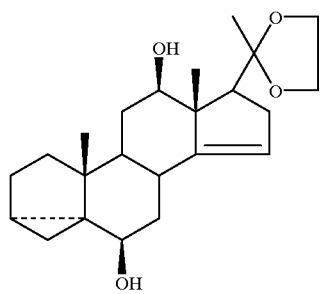

(28)

(d) treating the compound (28) with N-bromoacetamide, optionally acetic acid, and a base, e.g. pyridine, to produce a compound 6β, 12β-dihydroxy-20,20-ethylenedioxy-14,15-epoxy-3,5α-cyclopregnane of the formula

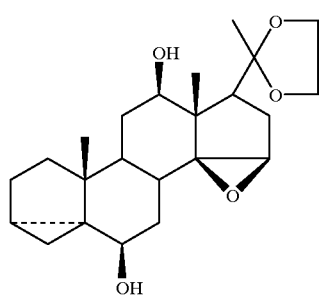

(29)

(e) treating the compound (29) with a reducing agent, e.g. LiAlH$_4$, and e.g. tetrahydrofuran, to produce a compound 6β, 12β, 14β-trihydroxy-20,20-ethylenedioxy- 3,5α-cyclopregnane of the formula

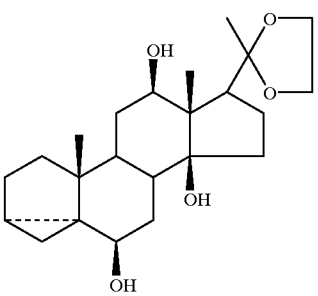

(30)

and (f) treating compound (30) with an acid, e.g. hydrochloric acid, and a solvent e.g. acetone, to produce compound (15).

Reaction Scheme B shows the procedure for the preparation of steroid intermediate (15) from compound (22) according to "the second alternative procedure" of the invention.

Reaction Scheme B

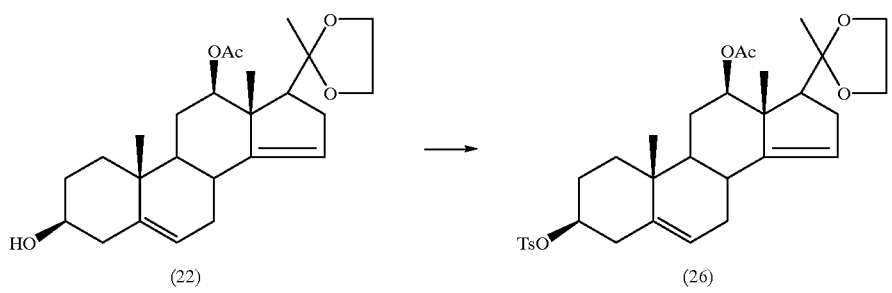

(22)                (26)

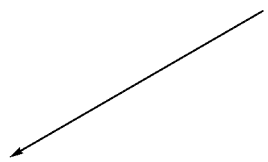

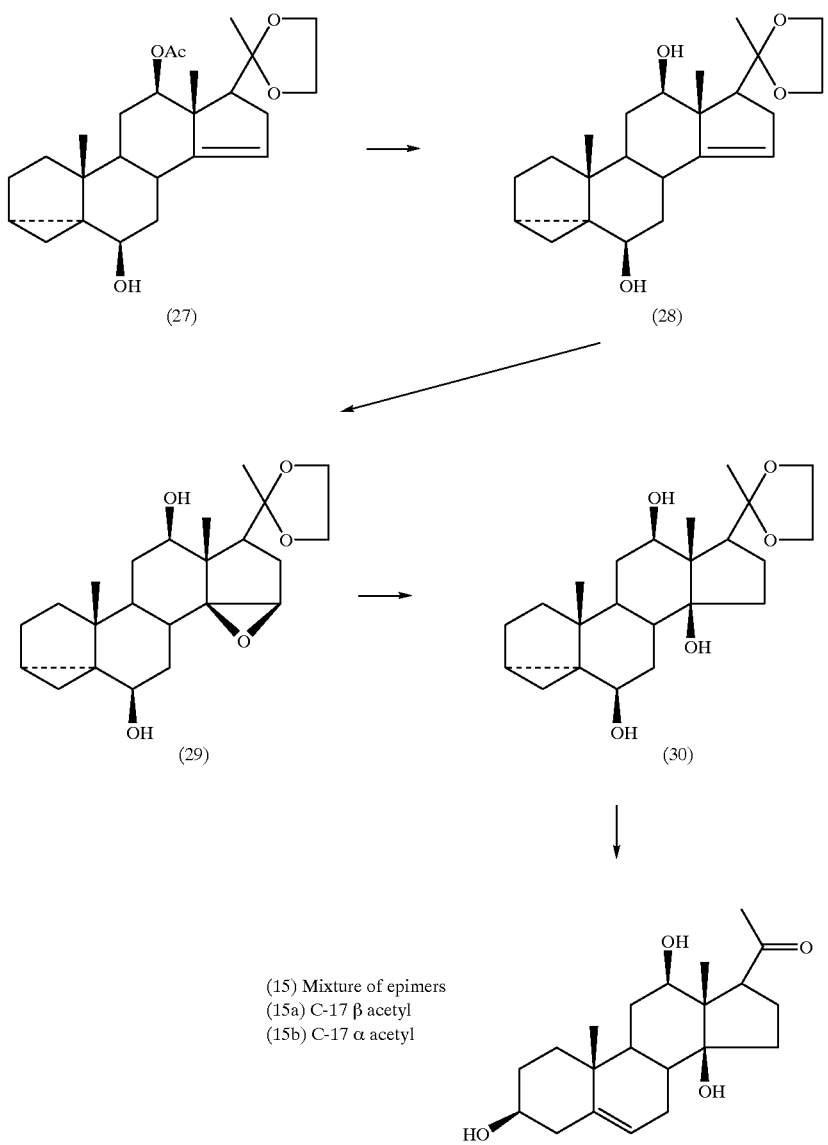

(15) Mixture of epimers
(15a) C-17 β acetyl
(15b) C-17 α acetyl

Compound (I) may be synthesized from a first carbohydrate intermediate in the form of an activated monosaccharide cymarose moiety, which can be prepared from a compound having the formula (36). Compound (36) can be prepared by a process which includes the steps
(i) treating methyl-α-D-glucose having the formula (31)

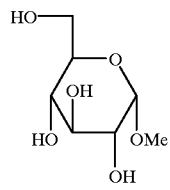

with benzaldehyde and zinc chloride to produce a compound methyl-4,6-0-benzylidene-α-D-glucopyranoside of the formula (32)

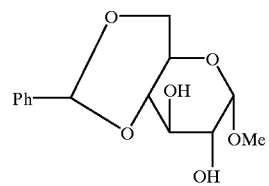

(ii) treating the compound (32) with tosyl chloride and pyridine at 0° C., to produce a compound methyl-4,6-0-benzylidene-2-0-tosyl-α-D-glucopyranoside of the formula

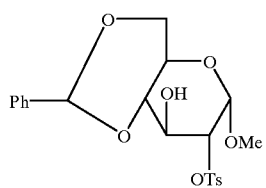

(33)

(iii) treating the compound (33) with NaOMe at 100° C. to produce a compound methyl 4,6-0-benzylidene-3-0-methyl-α-D-altropyranoside of the formula

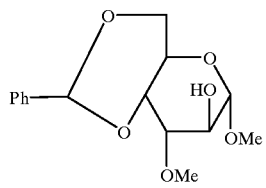

(34)

(iv) treating the compound (34) with N-bromosuccinamide (NBS) to produce a compound methyl 6-bromo-4-0-benzoyl-3-0-methyl-6-deoxy-α-D-altropyranoside of the formula

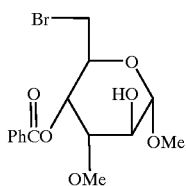

(35)

and (v) treating the compound (35) with NaBH$_4$ and NiCl$_2$, to produce a compound methyl 4-0-benzoyl-3-0-methyl-6-deoxy-α-D-altropyranoside of the formula

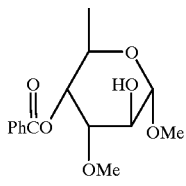

(36)

The invention extends to a process for the preparation of a carbohydrate intermediate in the form of an activated monosaccharide cymarose moiety which includes the steps of (i) treating the compound (36) with PhSSiMe$_3$, ZnI$_2$ and Bu4$^+$I$^-$ to produce a compound 4-0-benzoyl-3-0-methyl-6-deoxy-αβ-D-phenylthioaltroside of the formula

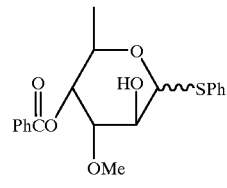

(37)

(ii) optionally treating the compound (37) with diethylaminosulphur trifluoride (DAST), e.g. at 0° C., to produce a compound 4-0-benzoyl-3-0-methyl-2-phenylthio-2,6-dideoxy-αβ-D-fluorocymaropyranoside having the formula

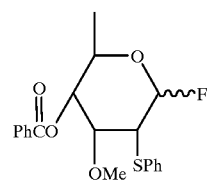

(38)

or (iii) optionally, treating the compound (37) with t-butyldimethylsilylchloride and imidazole in a solvent, e.g. pyridine, to produce 4-0-benzoyl-3-0-methyl-2-0-t-butyldimethylsilyl-αβ-D-phenylthioaltroside having the formula

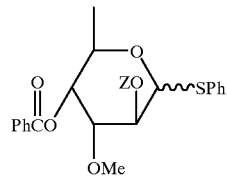

(39)

in which Z=TBDMS=t-butyldimethylsilyl and (iv) treating the compound (39) with a base, e.g. sodium methoxide, to produce 3-0-methyl-2-0-t-butyldimethylsilyl-αβ-D-phenylthioaltroside having the formula

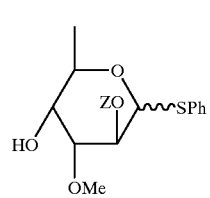

(40)

in which Z=TBDMS=t-butyldimethylsilyl.

Reaction Scheme C shows the procedure for the synthesis of the activated monosaccharide cymarose moiety (40) from compound (36) according to the invention (and includes the preparation of compound (36) from compound (31) for illustrative purposes).

Reaction Scheme C

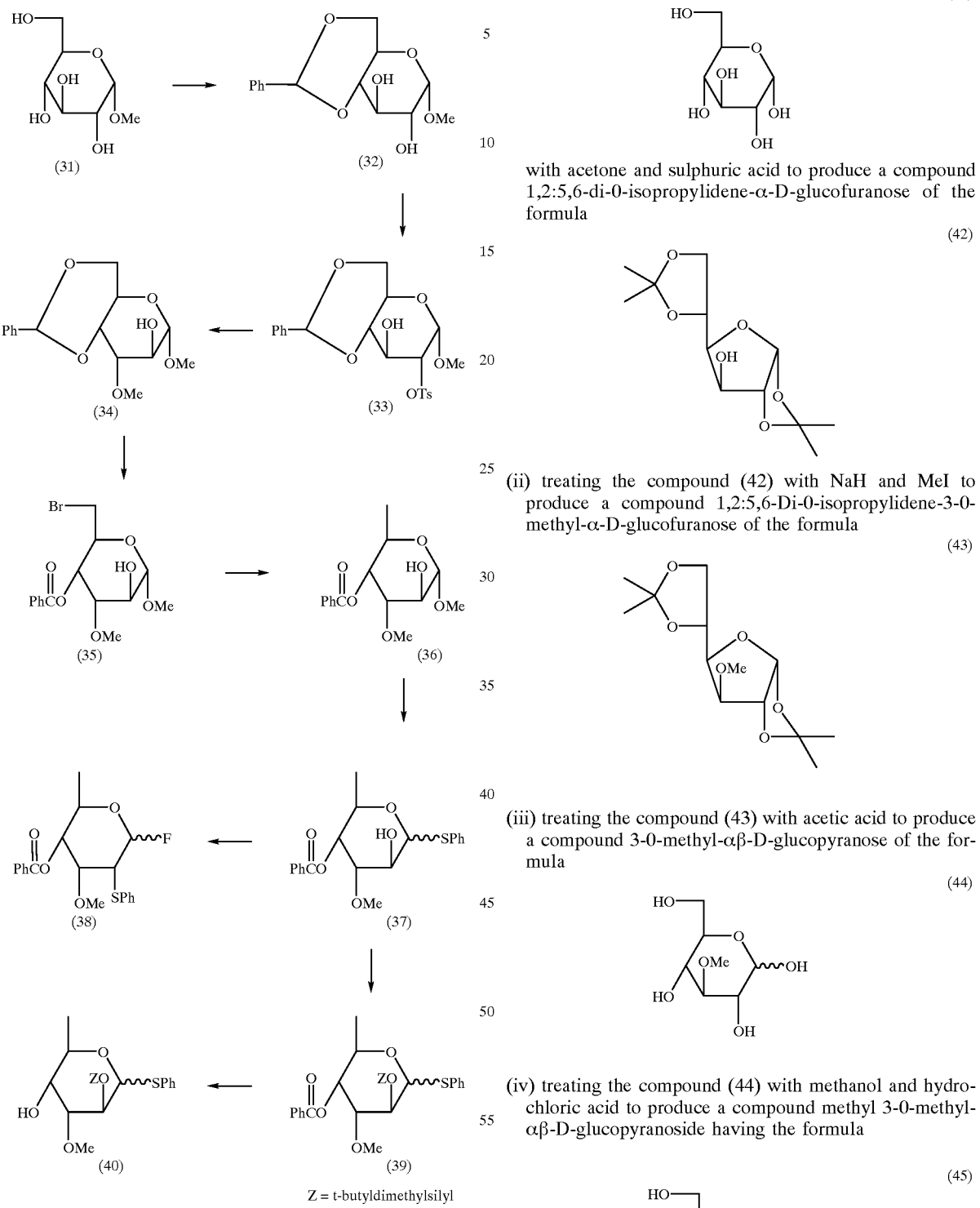

Z = t-butyldimethylsilyl

The synthesis of compound (1) may also involve a second carbohydrate intermediate in the form of an activated monosaccharide thevetose moiety, which can be prepared from a compound having the formula (47). Compound (47) can be prepared by a process which includes the steps of (i) treating α-D-glucose having the formula (41)

with acetone and sulphuric acid to produce a compound 1,2:5,6-di-0-isopropylidene-α-D-glucofuranose of the formula (42)

(ii) treating the compound (42) with NaH and MeI to produce a compound 1,2:5,6-Di-0-isopropylidene-3-0-methyl-α-D-glucofuranose of the formula (43)

(iii) treating the compound (43) with acetic acid to produce a compound 3-0-methyl-αβ-D-glucopyranose of the formula (44)

(iv) treating the compound (44) with methanol and hydrochloric acid to produce a compound methyl 3-0-methyl-αβ-D-glucopyranoside having the formula (45)

(v) treating the compound (45) with benzaldehyde and zinc chloride to produce a compound methyl 4,6-O-benzylidene-3-O-methyl-αβ-glucopyranoside having the formula (46)

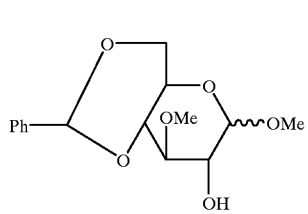

(vi) treating the compound (46) with N-bromosuccinamide, nickel chloride and sodium borohydride to produce a compound methyl 4-O-benzoyl-3-O-methyl-6-deoxy-αβ-glucopyranoside having the formula (47)

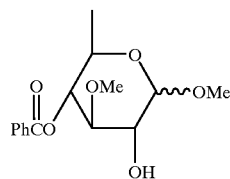

The invention extends to a process for the preparation of an activated monosaccharide thevetose moiety which includes the steps of (i) treating the compound (47) with phenylthiotrimethylsilane and trimethylsilyltrifluoromethanesulphonate to produce a compound 4-O-benzoyl-3-O-methyl-1-phenylthio-6-deoxy-αβ-glucopyranoside having the formula (48)

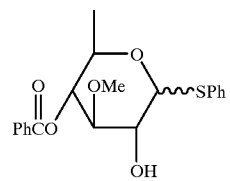

(ii) treating the compound (48) with pivaloyl chloride and a solvent, e.g. pyridine, to produce a compound 4-O-benzoyl-3-O-methyl-2-O-pivaloyl-1-phenylthio-6-deoxy-αβ-glucopyranoside having the formula (49)

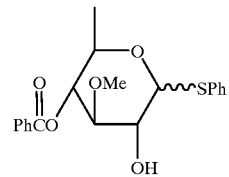

and (iii) treating the compound (49) with a brominating agent, e.g. N-bromosuccinimnide, and diethylaminosulphur trifluoride to produce a comnpound 4-0benzoyl-3-0-methyl-2-O-pivaloyl-1-stereo-isomers having the formula (50A)

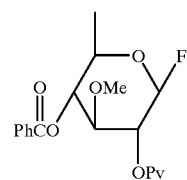

(50B)

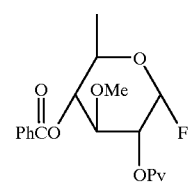

Reaction Scheme D shows the procedure for the synthesis of the activated monosaccharide thevetose moiety (50(A) and 50(B)) from compound (48) according to the invention (and includes the preparation of compound (47) from compound (41) for illustrative purposes)

Reaction Scheme D

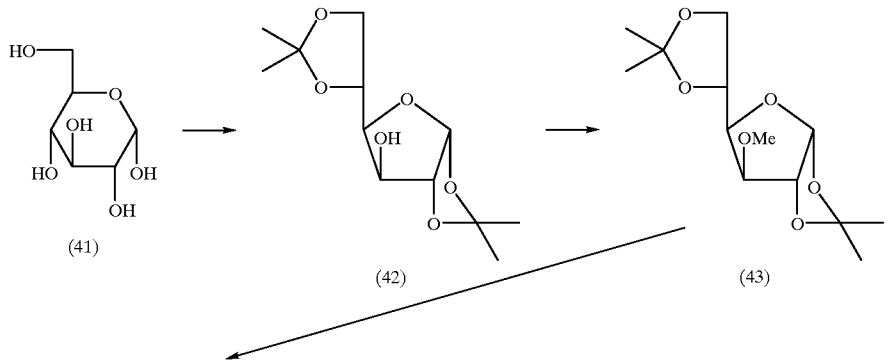

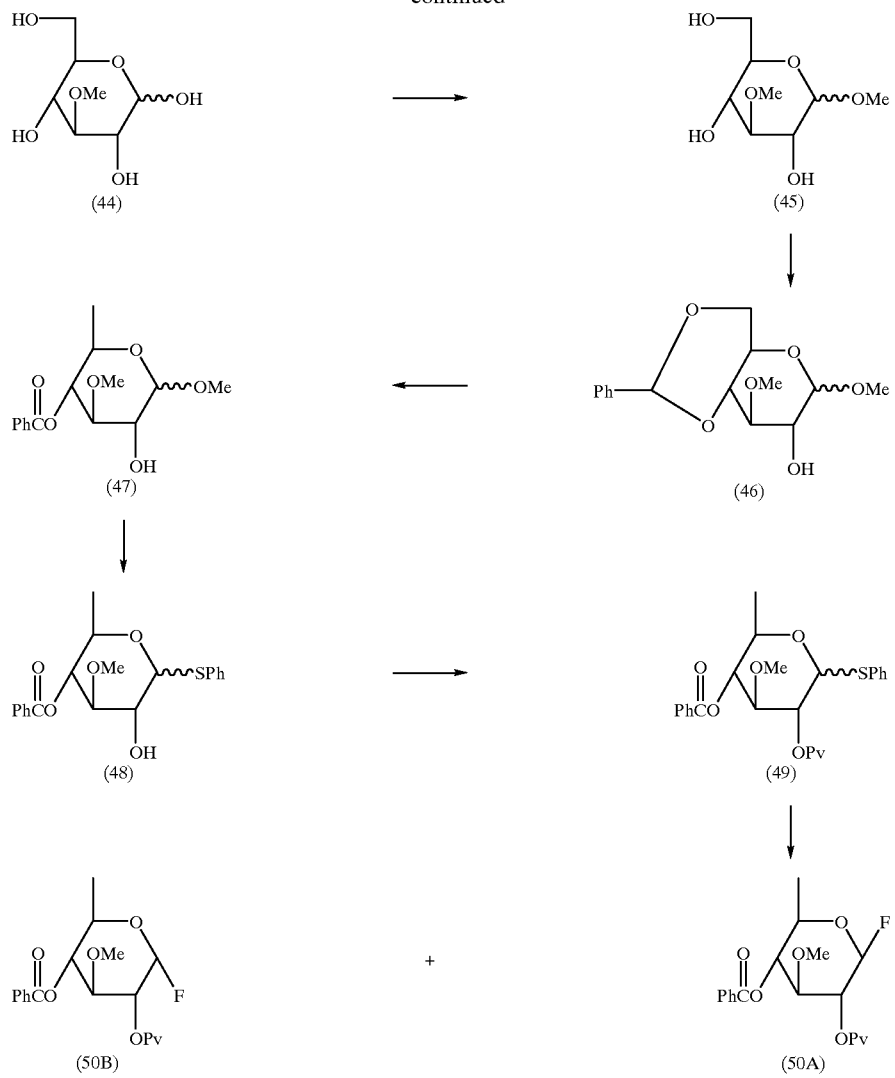

According to a still further aspect of the invention there is provided a process of synthetically producing a compound of the formula (1) and analogues and derivatives thereof which includes the steps of synthesising a suitable steroid intermediate or precursor and coupling the required number of suitable monosaccharides with the steroid intermediate.

The invention also provides a process of coupling a monosaccharide cymarose with the steroid intermediate, which includes the steps of (i) reacting a cymarose moiety (38) with a steroid intermediate (15), e.g. at −15° C., and in the presence of tin chloride, in a solvent, e.g. ether, to produce a compound 3-0-[4-0-benzoyl-2-phenylthio-β-D-cymaropoyranosyl]-12,14-β-dihydroxy-pregn-5-ene-20-one of the formula

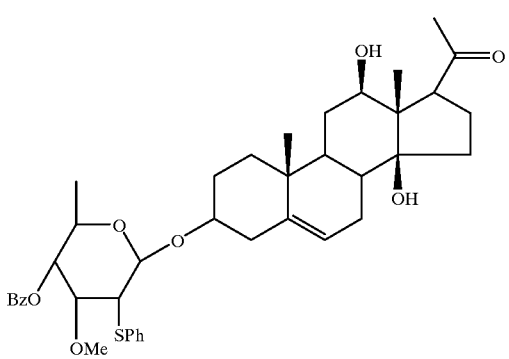

(51)

and (ii) treating the compound (51) with tiglic acid chloride in pyridine and thereafter with a base, e.g. NaOMe, to produce a compound 3-0-[-2-phenylthio-β-D-cymaropyranosyl]-12β-tigloyloxy-14-hydroxy-14β-pregn-5-ene-20-one of the formula (52)

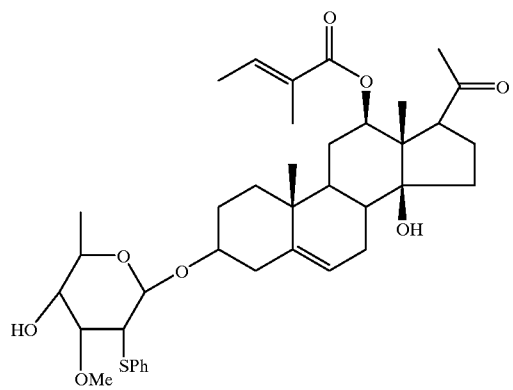

The invention extends to a process which includes coupling a monosaccharide cymarose moiety to a monosaccharide thevetose moiety and coupling the resultant disaccharide with the combined steroid product (52) to form compound (1).

The process of coupling the monosaccharide cymarose moiety to the monosaccharide thevetose moiety and coupling the resultant disaccharide to the combined steroid product (52) may include the steps of (4) coupling a selectively protected cymarose moiety (40) and a selectively protected thevetose moiety (50 A) using tin chloride (SnCl₂) and silver trifluoromethanesulphonate, e.g. at −15° C., to produce a compound of the formula (53)

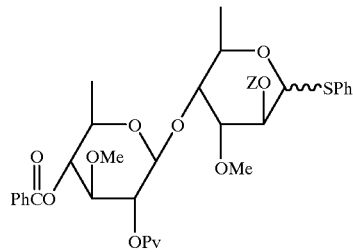

in which Z=TBDMS=t-butyldimethylsilyl
(ii) treating compound (53) with tetrabutylammoniumfluoride to produce a compound of the formula (54)

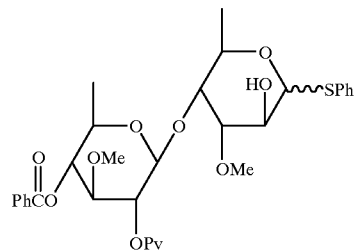

(iii) treating compound (54) with diethylaminosulphur trifluoride, e.g. at 0° C., to produce a compound of the formula (55)

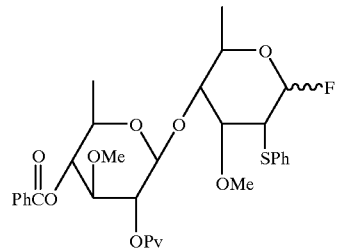

(iv) reacting compound (55) with compound (52) to produce a compound of the formula (56)

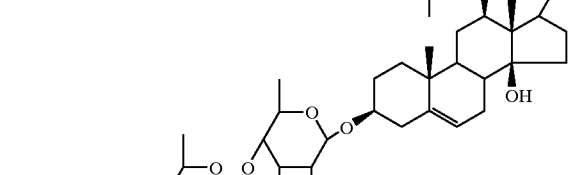

and (v) treating compound (56) in a Raney-Nickel reaction and thereafter with a base, e.g. NaOMe, to produce compound (1) as described above.

Reaction Scheme E shows the procedure for the synthesis of intermediates (52) and (55) and coupling them to form compound (56).

Reaction Scheme E
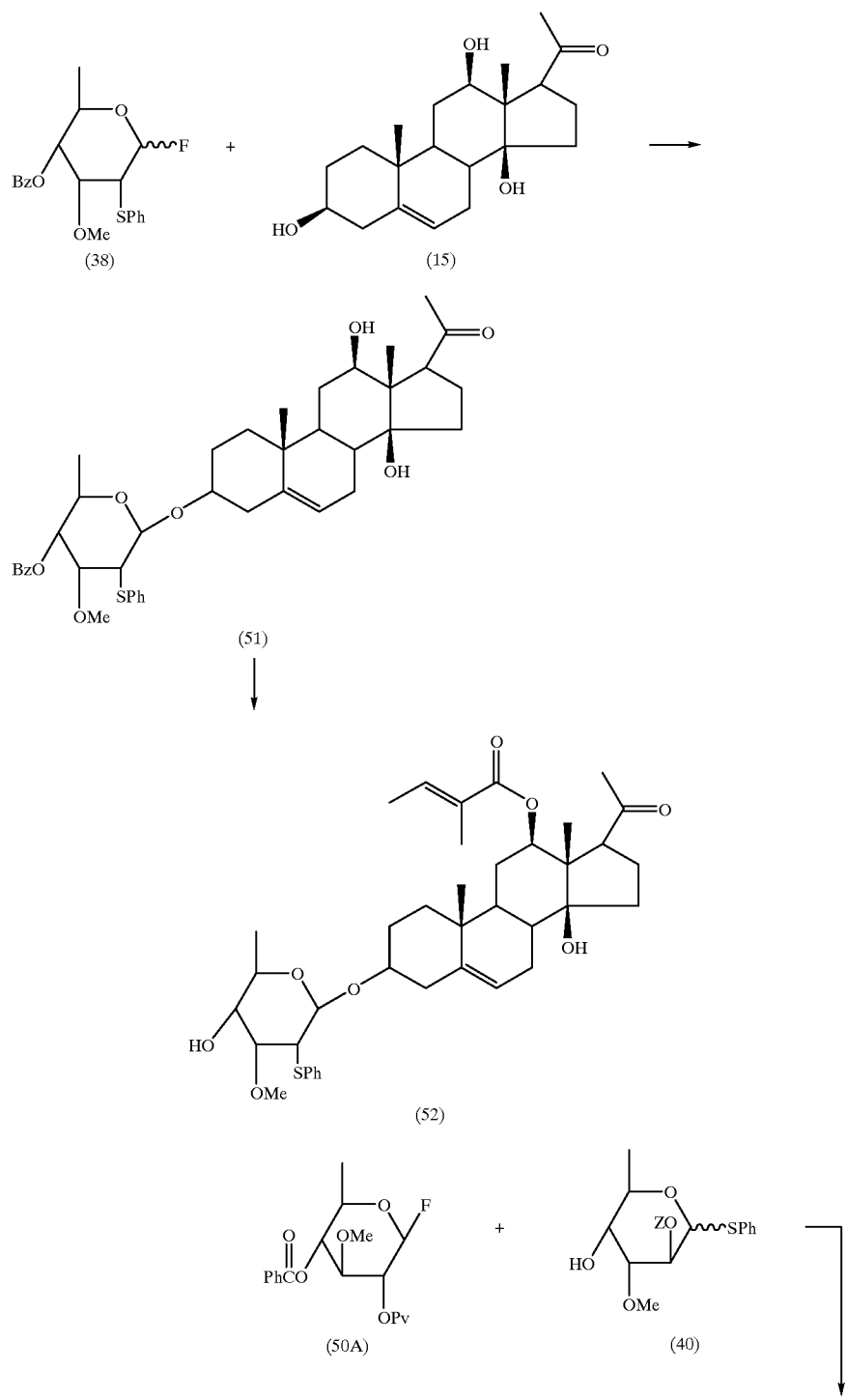

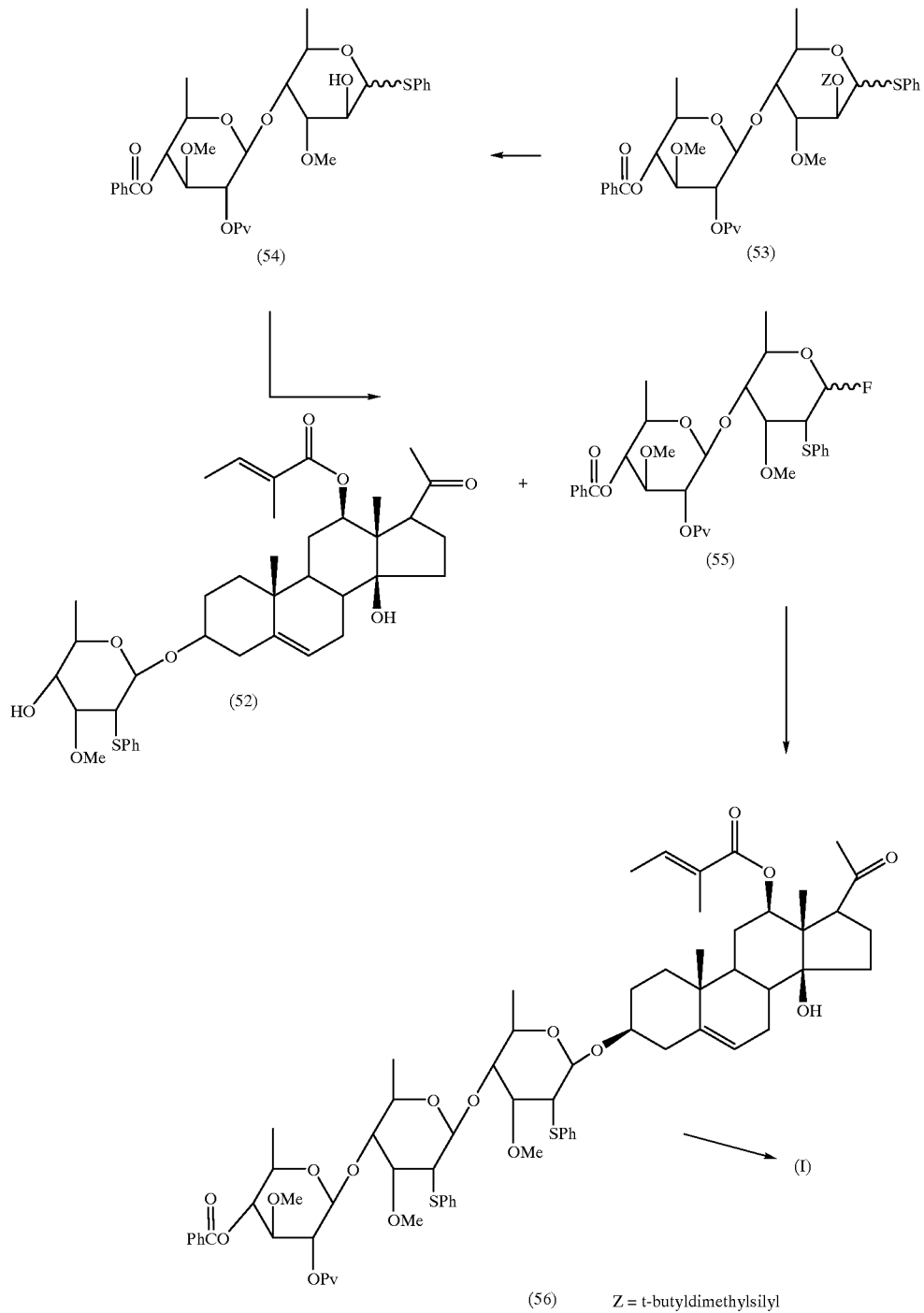

According to the invention, an alternative process is provided which includes coupling cymarose and thevetose moieties to form a trisaccharide and coupling the trisaccharide onto a steroid derivative to form a compound of the formula (1).

The process of forming the trisaccharide and coupling the resultant trisaccharide to a steroid derivative may include the steps of (i) coupling a selectively protected cymarose moiety (40) and compound (45) using tin (II) chloride, AgOTf, Cp$_2$ZrCl$_2$ to produce a compound of the formula

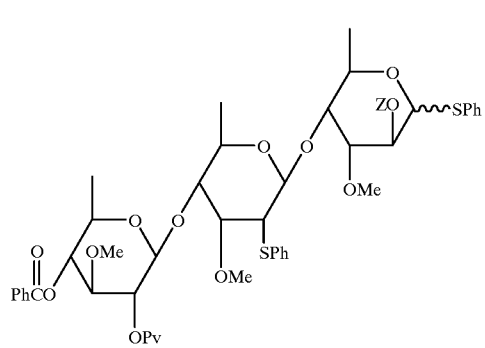

(57)

in which Z=TBDMS=t-butyldimethylsilyl
(i) treating compound (57) with tetrabutylammonium luoride and diethylaminosulphur trifluoride to produce a trisaccharide compound having the formula

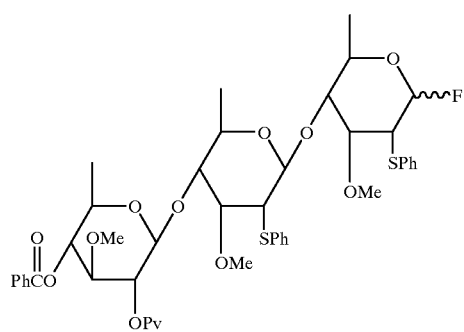

(58)

and (iii) coupling the trisaccharide (58) with a steroid intermediate of the formula

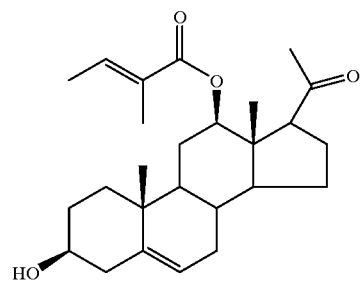

(59)

using tin (II) chloride, AgOTf, Cp$_2$ZrCl$_2$ to produce compound (1).

The steroid intermediate (59) may be produced by treating steroid (15) with tiglic acid chloride.

Reaction Scheme F shows the procedure for the synthesis of the trisaccharide (58) and the synthesis of compound (1) by coupling the trisaccharide (58) with the steroid intermediate (59).

Reaction Scheme F

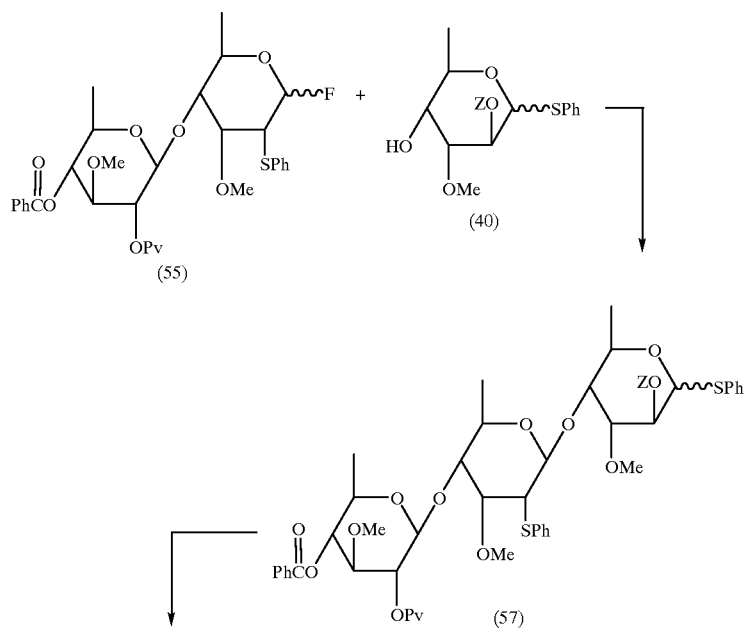

-continued

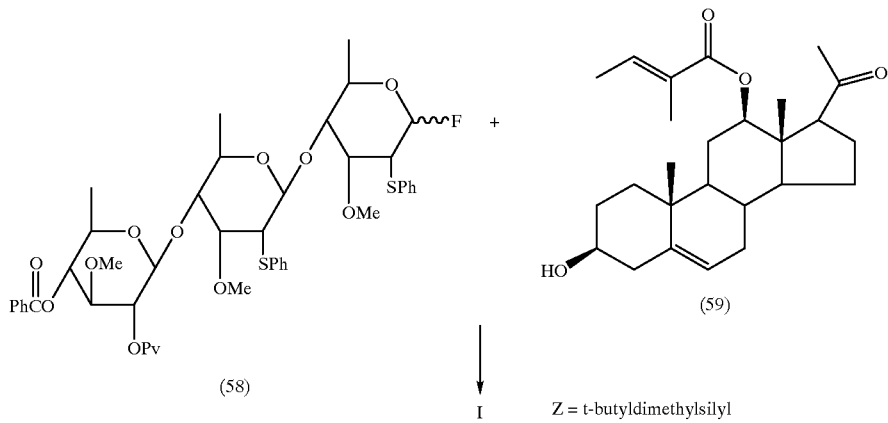

(58)

(59)

I    Z = t-butyldimethylsilyl

The intermediates (23), (24), (25), (27), (28), (29), (30), (37), (38), (39), (40), (48), (49), (50), (51), (53), (54), (55), (56), (57) and (58) described above are novel compounds and the invention extends to these compounds as such.

Compound (1), 3-0-[-β-D-thevecopyranosyl-(1→4)-β-D-cymaropyranosyl-(1→4)-β-D-cymaropyranosyl]-12β-0-tigloyloxy-14-hydroxy-14β-pregn-5-en-20-one, and various analogues and derivatives thereof have been found to have appetite suppressing activity.

The invention extends also to a composition or formulation having appetite suppressant activity, in which the active ingredient is an extract obtained from a plant of the genus Trichocaulon or the genus Hoodia.

The active ingredient may be a compound of the formula (1), extracted from a plant of the genus Trichocaulon or Hoodia or a derivative thereof. The plant may be of the species *Trichocaulon officinale* or *Trichocaulon piliferum*, or the species *Hoodia currorii, Hoodia gordonii* or *Hoodia lugardii*.

The invention extends also to a composition or formulation having appetite suppressant activity, in which the active ingredient is a synthetically produced compound of the formula (1) or a derivative or analogue thereof, as hereinbefore set out with reference to compounds (2) to (14).

According to another aspect of the invention there is provided a method of suppressing an appetite by administering to a human or animal a suitable dosage of an appetite suppressant agent comprising an extract of a plant of the genus Trichocaulon or Hoodia. The extract may be incorporated in a composition or formulation including also pharmaceutically acceptable other ingredients.

The appetite suppressant agent may be an isolated natural chemical or a synthetic chemical compound of the formula:

(1)

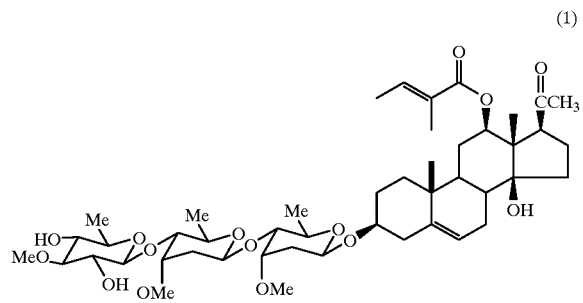

or derivatives or analogues thereof, as set out before.

The appetite suppressant composition or formulation may consist of the appetite suppressant agent admixed with a Apharmaceutical excipient, diluent or carrier. Other suitable additives, including a stabilizer and such other ingredients as may be desired may be added.

The invention extends to the use of compound (1) or its derivatives or analogues in the manufacture of a medicament having appetite suppressant activity.

The invention further extends to compound (1), or its derivatives or analogues as set out before, for use as a medicament having appetite suppressant activity.

A method of suppressing an appetite by administering to a human or animal an effective dosage of a composition as described above is also provided.

A method has been described herein for extracting a steroidal glycoside having appetite suppressant activity from plant material obtained from a plant of the Trrichocaulon or Hoodia genus. The invention thus extends to an extract obtained from plant material of the Trichocaulon or Hoodia genus and containing a substantially pure steroidal glycoside of formula (1).

The invention extends also to a foodstuff or a beverage containing an effective quantity of the steroidal glycoside of the formula (1), or its derivatives or analogues as set out before, to have an appetite suppressant effect when ingested.

Molecular genetic studies have led to a considerable increase in the understanding of the regulation of appetite, satiety and bodyweight. These studies have revealed numerous central regulatory pathways, mediated by a number of neuropeptides. The maintenance of a normal body weight is achieved by an intricate balance between energy intake, food consumption, and energy expenditure. Energy homeostasis is subject to a wide range of influences, ultimately controlled by the brain. The different signals include such things as sense of smell and taste and gastro-intestinal signals such as distension of the gastro-intestinal tract, chemical signals to the gastric mucosa and blood-borne metabolites such as fatty acids and glucose.

Centrally, neuropeptide "Y" (NPY) which is negatively regulated by leptin, has been established as one of the positive regulators of feeding behaviour. Expression of the endogenous antagonist for melanocortin receptors has also been shown to be the basis for obesity in a particular model (the ob/ob mouse). Indeed deficiency at the MC4 melanocortin receptor completely replicates the obesity syndrome. Other mediators which have been shown to have roles in the energy balance include bombesin, galonin and glucagon-like peptide-1.

Without being bound by theory, the Applicant believes that compound (1) and its analogues as described above act as an agonist of the melanocortin 4 receptor. The effect of this is to regulate NPY but also to increase cholecystokinin. The effect of cholecystokinin amongst other things is to inhibit gastric emptying.

Accordingly, the invention extends to a composition having appetite suppressant activity comprising a melanocortin 4 receptor agonist.

The agonist may be an extract or compound as previously described, in particular the compound of formula (1) The composition may be admixed with a pharmaceutical excipient, diluent or carrier and is optionally prepared in unit dosage form.

The invention still further extends to the use of a melanocortin 4 receptor agonist in the manufacture of a medicament having appetite suppressant activity, to a melanocortin 4 receptor agonist for use as a medicament having appetite suppressant activity, to a method of suppressing an appetite by administering to a human or animal an effective dosage of a composition comprising a melanocortin 4 agonist as described above, and to the use of a melanocortin 4 receptor agonist to suppress the appetite of and/or to combat obesity in a human or animal.

The invention and its efficacy will now be further described, without limitation of the scope of the invention, with reference to the following examples and drawings.

BRIEF DESCRIPTION OF THE DRAWINGS

In the drawings,

FIG. 5 and 6 show a graphical representation of the percentage change of body mass of rats for different groups for days −7 to 7 and days 0 to 7 respectively in a repeat dose study using a sap extract and a spray-dried sap extract of plant material of the species *Hoodia gordonii*.

EXAMPLE 1

Figure 1:
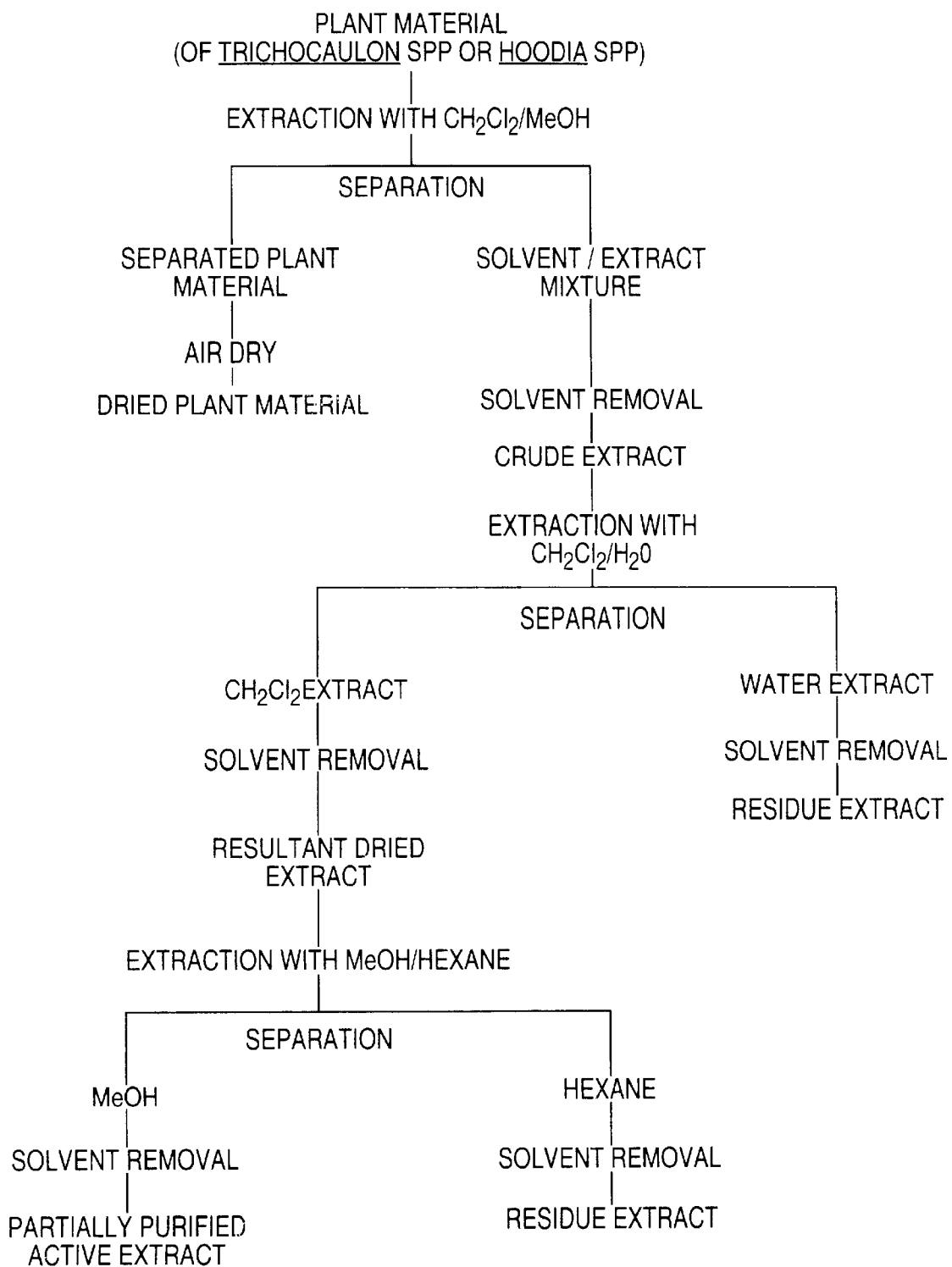
FIG. 1 shows a flow diagram of the general method of extracting a first crude appetite suppressant extract and a purified appetite suppressant extract from plant material of the genus Trichocaulon or Hoodia.

The general method of extracting a first crude appetite suppressant extract and a purified appetite suppressant extract from plant material of the genus Trichocaulon or of the genus Hoodia is illustrated by way of the flow diagram of FIG. 1.

EXAMPLE 2

Bioassays carried out on rats using a partially purified methanol extract obtained in the manner illustrated in Example 1, indicated that the extract does in fact exhibit appetite suppressant activity. The appetite suppressant activity of the active extract can be illustrated by way of a typical example of the effect of the methanol extract of *Trichocaulon piliferum* on rats, by way of the graphic representation in FIG. 2.

Figure 2:
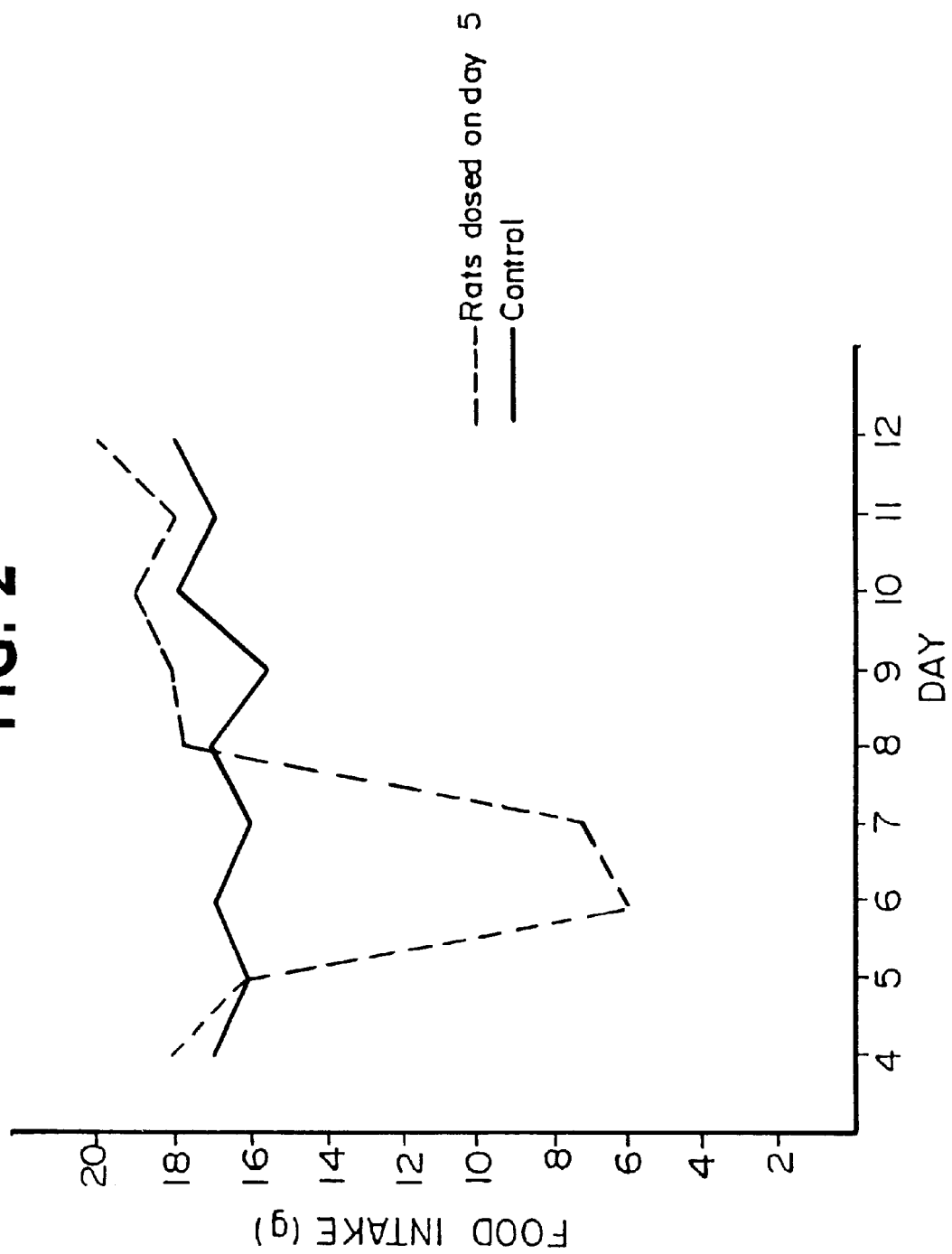
FIG. 2 shows a graphical representation of a bioassay carried out on rats using a partially purified methanol extract of *Trichocaulon piliferum*.

It will be evident from FIG. 2 that the test group of rats dosed with the extract on day 5 displayed a substantially diminished food intake over the next two days, while a control group did not disclose a comparable reduced food intake. The food intake of the test group returned to normal, and in fact increased, from day 8 onwards.

EXAMPLE 3

Figure 3:
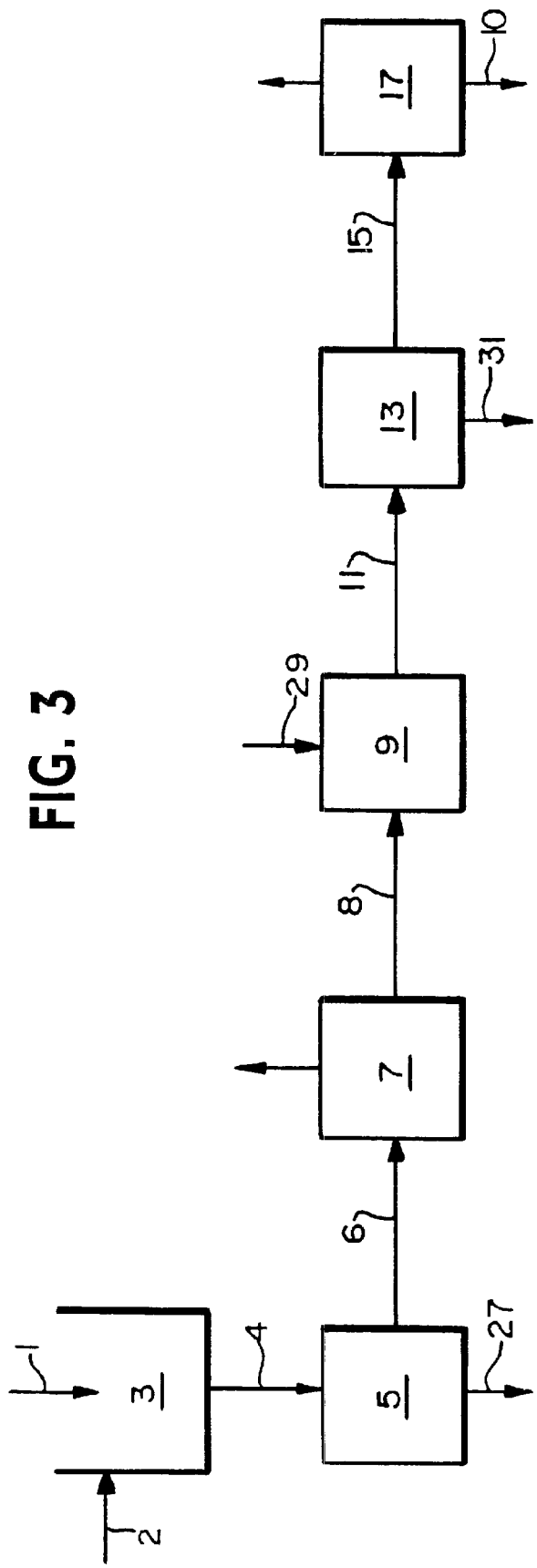
FIGS. 3 and 4 together show a schematic representation of a preferred embodiment of the process of the invention for producing an extract of plant material of the genus Trichocaulon or Hoodia.
Figure 4:
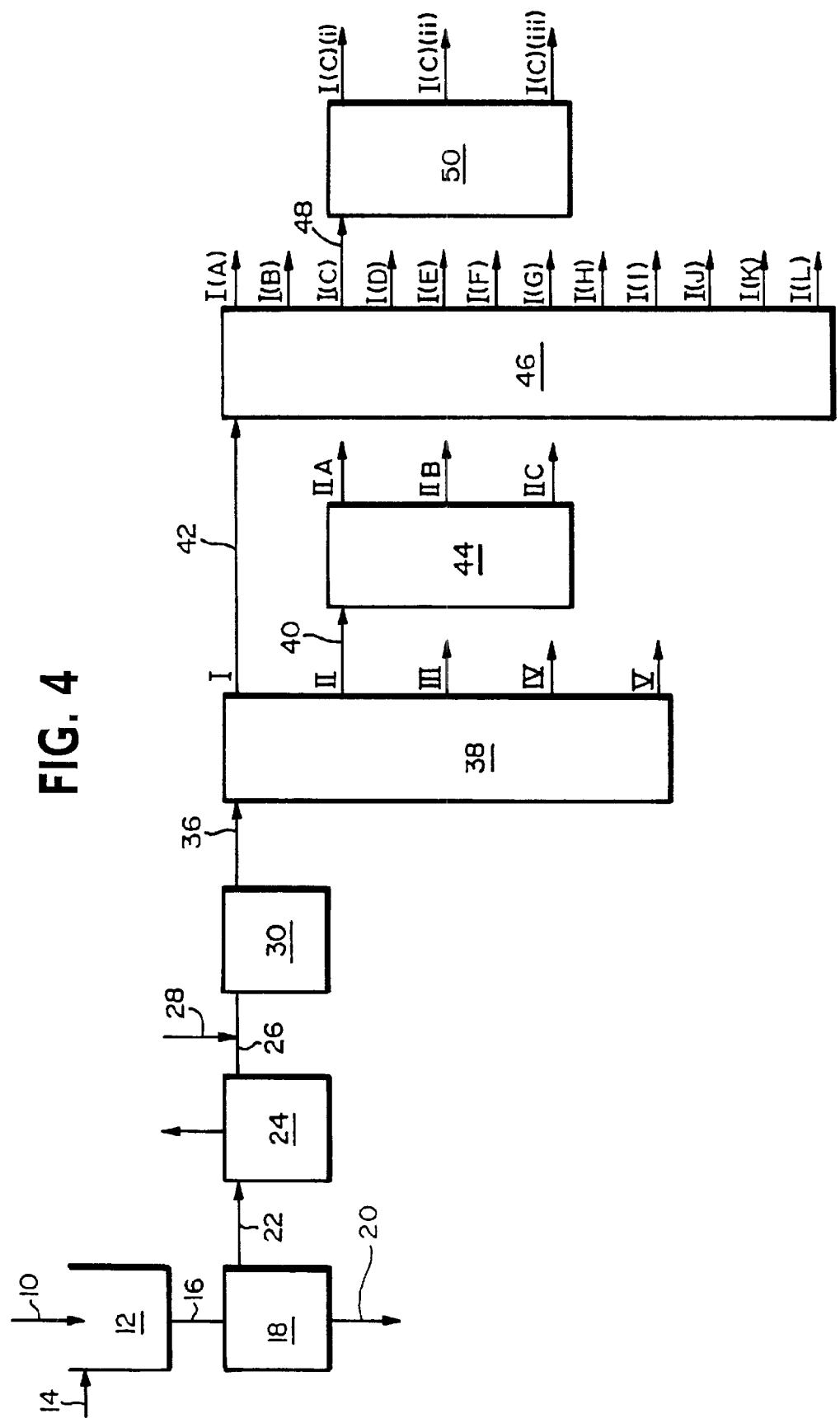

A preferred embodiment of a process in accordance with the invention for producing an extract having appetite suppressant activity is illustrated schematically by way of example in FIGS. 3 and 4, which two Figures together illustrate the comprehensive process. However, various other procedures may be used, as will be understood by persons skilled in the art.

Referring to FIG. 3, plant material of the genus Trichocaulon or the genus Hoodia is fed into a blender 3, eg a Waring blender, by way of feedline 1, with a solvent in the form of a methylene chloride/methanol solution introduced via feedline 2. The homogenised product is fed via line 4 into a separation stage 5, eg in the form of a filter or centrifuge, and the residual plant material is removed via line 27.

The solvent/extract mixture is fed via line 6 into an evaporation stage 7, where the solvent is removed, for example by means of a rotor evaporator. The dried crude extract is fed via line 8 into a further extraction stage 9 with the addition of a methylene chloride/water solution introduced via feedline 29 for further extraction, and then to a separation stage 13 by way of line 11, where the water fraction is removed via line 31. The dissolved extract fraction is fed via line 15 into a drier stage 17 where the solvent is evaporated, for example by a rotor evaporator.

Referring to FIG. 4, the dried extract is fed via line 10 into an extraction stage 12. A methanol/hexane solution is also fed via line 14 into the extraction stage 12 for further purification and extraction of the dried extract. The extract/methanol/hexane mixture is fed via nine 16 into a separation stage 18, the hexane fraction is removed via line 20, and the methanol/extract mixture is then fed via line 22 into a drying stage 24. In the drying stage 24, the solvent is removed, eg by evaporation on a rotor evaporator.

The dried, partially purified active extract is fed via line 26 and with the addition of methanol via line 28 into a solution stage 30, and the dissolved fraction is fed via line 36 to a chromatography column 38.

In the column 38 the methanol soluble fraction is further fractionated, using silica gel and a chloroform/30% methanol solvent, into different fractions schematically indicated as fractions I to V. According to an actual fractionation procedure carried out by the Applicant, the fractionation procedure yielded the following fraction weights: I(3.9 g); II(2.6 g); III(2.1 g); IV(1.1 g) and V(2.0 g). These fractions are individually evaluated by a suitable bioassaying procedure (in a step not shown) and those fractions identified as fractions I and II, displaying marked appetite suppressant activity, are fed by feedlines 40 and 42 into columns 44 and 46 respectively where they are further fractionated and purified by column chromatography, again by using silica gel and a 9:1 chloroform:methanol system.

The sub-fractions II(A)–(C) obtained from column 44 do not, when assayed, display a noteworthy appetite suppressant activity, and may be recycled for further chromatography.

The sub-fractions I(A)–(L) obtained from column 46 are also evaluated (by an assaying step not shown), and the sub-fraction I(C) is found to have marked appetite suppressant activity.

The sub-fraction I(C) is fed via line 48 into column 50 for a further fractionation and purification, using silica gel and a 9:1 ethyl acetate:hexane eluent. Of the resultant purified fractions, fraction I(C) (ii) is found, after assaying, to possess marked appetite suppressant activity.

The purified product is identified by nuclear magnetic resonance spectroscopy (as indicated in Tables 1 and 2 below), to be compound (1).

TABLE 1

$^1$H (300.13 MHz) n.m.r. data for compound (1) CDCl$_3$

Compound (1)

| Hydrogen Atom | J(HH)/Hz | $\delta_H$/p.p.m. |
|---|---|---|
| Aglycone-3 | — | 3.522 m |
| 6 | — | 5.381 m |
| 12 | 11.5, 4.1 | 4.607 dd |
| 17 | 9.3, 9.3 | 3.157 dd |
| 18 | — | 1.029 s |
| 19 | — | 0.951 s |
| 21 | — | 2.164 s |
| 3* | 7.1, 1.5 | 6.888 qq |
| 4* | 7.1, 1.2 | 1.806 dq |
| 5* | 1.6, 1.2 | 1.853 dq |
| Cym-1' | 9.4, 2.1 | 4.816 dd |
| 2'$_{aq}$ | 13.8, 3.7, 2.1 | 2.055 ddd |
| 2'$_{ax}$ | 13.8, 9.4, 2.6 | 1.552 ddd |
| 3' | 3.7, 2.9, 2.6 | 3.776 ddd |
| 4' | 9.4, 2.9 | 3.179 dd |
| 5' | 6.3, 9.4 | 3.821 dd |
| 6' | 6.3 | 1.279 d$^a$ |
| 3'-OMe | — | 3.408 s$^d$ |
| 1" | 9.4, 2.1 | 4.730 dd |
| 2" | 13.8, 3.7, 2.1 | 2.108 ddd |
| 2"$^{aq}$ | 13.8, 9.4, 2.6 | 1.601 ddd |
| 3"$^{ax}$ | 3.7, 2.9, 2.6 | 3.755 ddd |
| 4" | 9.4, 2.9 | 3.239 dd |
| 5" | 6.3, 9.4 | 3.898 dd |
| 6" | 6.3 | 1.243 d$^b$ |
| 3"-OMe | — | 3.392 s$^e$ |
| Thev-1''' | 7.7 | 4.273 d |
| 2''' | 7.7, 8.0 | 3.469 dd |
| 3''' | 8.0, 2.9 | 3.099 dd |
| 4''' | 9.3, 2.9 | 3.179 dd |
| 5''' | 6.3, 9.3 | 3.351 dd |
| 6''' | 6.3 | 1.183 d$^c$ |
| 3'''-OMe | — | 3.622 s |

$^a$, $^b$, $^c$ in each column may be interchangeable.
$^d$, $^e$ in each column may be interchangeable,
*Refers to the tigloate group atoms

TABLE 2

Relevant $^{13}$C (75.25 MHz) n.m.r. data for Compound (1) in CDCl$_3$

| Aglycone moiety | | Sugar moiety | |
|---|---|---|---|
| Carbon | $\delta_c$/p.p.m. | Carbon | $\delta_c$/p.p.m. |
| 1 | 37.04 T | cym- 1' | 95.84 D |
| 2 | 29.44 T | 2' | 35.57 T |
| 3 | 77.24 D | 3' | 77.05 D |
| 4 | 38.62 T | 4' | 82.57 D |
| 5 | 138.95 S | 5' | 68.48 D |
| 6 | 131.90 D | 6' | 18.14 Q |
| 7 | 27.30 T | 3'-OMe | 57.93 Q |
| 8 | 35.30 D | 1" | 99.54 D |
| 9 | 43.04 D | 2" | 35.17 T |
| 10 | 37.22 S | 3" | 76.99 D |
| 11 | 26.04 T | 4" | 82.52 D |
| 12 | 75.88 D | 5" | 68.30 D |
| 13 | 53.71 S | 6" | 18.36 Q |
| 14 | 85.69 S | 3"-OMe | 57.09 Q |
| 15 | 34.36 T | Thev- 1''' | 104.28 D |

TABLE 2-continued

Relevant $^{13}$C (75.25 MHz) n.m.r. data for Compound (1) in CDCl$_3$

| Aglycone moiety | | Sugar moiety | |
|---|---|---|---|
| Carbon | $\delta_c$/p.p.m. | Carbon | $\delta_c$/p.p.m. |
| 16 | 24.31 T | 2''' | 74.62 D |
| 17 | 57.18 D | 3''' | 85.30 D |
| 18 | 9.85 Q | 4''' | 74.62 D |
| 19 | 19.27 Q | 5''' | 71.62 D |
| 20 | 216.85 S | 6''' | 17.75 Q |
| 21 | 33.01 Q | 3'''-OMe | 60.60 Q |
| 1* | 167.60 S | | |
| 2* | 128.69 D | | |
| 3* | 137.66 D | | |
| 4* | 14.41 Q | | |
| 5* | 12.08 Q | | |

*Refers to the tigloate group atoms

Compound (1)

IR data: 3440 cm$^{-1}$ (OH), 2910 cm$^{-1}$ (CH), 1700 cm$^{-1}$ (C=O) $[\alpha_D]^{20}_{589}$=12,67° (C=3, CHCl$_3$): m.p. 147° C.–152° C.

Examples 4 to 13 illustrate the synthetic procedures whereby the intermediate compounds and steroid (15) may be prepared according to "the first alternative procedure".

EXAMPLE 4

12β, 15β-Dihydroxy progesterone (17)

Cultures of Calonectria decora (ATCC 14767) are prepared by the inoculation of a culture medium comprised of sucrose (900 g), K$_2$HPO$_4$ (30 g), Czapek concentrate (300 ml), corn steep liquor (300 ml) and distilled water (30 l) (150×500 ml flasks). After 5 days of shaking at 26° C., progesterone (16) (150 g) in a suspension of Tween 80 (0,1% soln., 1,5 l) is added to the flasks. The cultures are incubated for a further 5 days and then worked-up by centrifugation, decantation, extraction of the medium with chloroform, and then evaporation to yield the dihydroxy progesterone (17) (75 g, 45%)

$^1$H NMR (CDCl$_3$): 5,71 (1H, s, H-4); 4,12–4,22 (1H, m, H-15) 4,43 (1H, br, s, OH); 3,46–3,53 (1H, dd, J=4,6 Hz, H-12); 2,16 Hz (3H, s, H-21); 1,18 (3H, s, H-19) 0,74 (3H, s, H-18).

EXAMPLE 5

12β-Hydroxy-15α-(p-toluene sulfonyl)-progesterone (18)

The dihydroxy progesterone (17) (75 g, 0.22 mol) is dissolved in dry pyridine (300 ml) and cooled to 0° C. p-Toluene sulfonyl chloride (46 g, 0,24 mol) in dry pyridine (200 ml) is added dropwise to the reaction mixture at 0° C. The reaction is stirred overnight at 0° C., and quenched by the addition of H$_2$O (500 ml). The water layer is extracted with ethyl acetate (1 l), and the organic extract washed with hydrochloric acid (6M, 3×1 l), aqueous saturated sodium bicarbonate (500 ml), aqueous saturated sodium chloride (500 ml), and water (500 ml). The organic layer is dried (MgSO$_4$), filtered and evaporated to yield p-toluene sulfonated progesterone (18) (98 g, 92%) as a viscous dark yellow oil.

$^1$H NMR (CDCl$_3$): 7,7 (2H, d, J=14 Hz, H-2,6); 7,34 (2H, d, J=8,4 Hz, H-3,5); 5,67 (1H, s, H-4); 4,86–4,93 (1H, m, H-15); 3,45–3,50 (1H, dd, J=4,6 Hz, H-12); 2,44 (3H, s, H-4Me); 2,15 (3H, s, H-21) 1,13 (3H, s, H-19); 0,74 (3H, s, H-18).

EXAMPLE 6

12β-Hydroxy-Δ$^{14}$-Droaesterone (19)

A solution of the tosylated progesterone (18) (98 g, 0,19 mol) in 2,4,6-trimethyl collidine (500 ml) is refluxed at 150° C. for 3 h. The reaction mixture is cooled and poured into water (500 ml). The water layer is extracted with ethyl acetate (1 l), after which the organic layer is washed with hydrochloric acid (6M, 3×1 l), aqueous saturated sodium bicarbonate (500 ml), aqueous saturated sodium chloride (500 ml), and water (500 ml). After drying (MgSO$_4$) and filtering, the ethyl acetate is evaporated and the crude mixture is purified by silica gel chromatography, eluting with acetone:chloroform (1:10) to afford Δ$^{14}$-progesterone (19) (50 g, 78 %) as a dark red oil.

$^1$H NMR (CDCl$_3$): 5,73 (1H, s, H-4), 5,28 (1H, dd, J=2,2 Hz, H-15), 4,41 (1H, br, s, OH), 3,49–3,52 (1H, dd, J=4,3 Hz, H-12), 2,80–2,84 (1H, dd, J=9,2 Hz, H-17), 2,14 (3H, s, H-21), 1,19 (3H, S, H-19), 0.89 (3H, s, H-18).

EXAMPLE 7

3,12β-Diacetoxypregna-3,5,14-trien-20-one (20)

A solution of Δ$^{14}$-progesterone (19) (50 g, 0,15 mol) in acetyl chloride (1,5 l) and acetic anhydride (750 ml) is refluxed for 2 hours. The reaction mixture is poured into cold ethyl acetate (1 l) and aqueous saturated sodium bicarbonate is added with stirring until the effervescence ceases. The ethyl acetate layer is separated from the sodium bicarbonate layer and washed with further portions of aqueous sodium bicarbonate (3×700 ml), thereafter with aqueous saturated sodium chloride (700 ml) and finally with water (700 ml). The organic layer is dried (MgSO$_4$), filtered and evaporated to afford the 3,12β-diacetoxypregna-3,5,14-trien-20-one (20) (60 g, 93%) as an orange oil.

$^1$H NMR(CDCl$_3$): 5,68 (1H, s, H-4), 5,44 (1H, m, H-6), 5,31 (1H, dd, J=2,2 Hz, H-15), 4,82–4,86 (1H, dd, J=4,5 Hz, H-12), 3,10–3,18 (1H, t, J=9,5 Hz, H-17), 2,18 (3H, s, 3-Ac), 2,11 (3H, s, 12-Ac), 2,08 (3H, s, H-21), 1,02 (3H, s, H-19), 1,01 (3H, s, H-18).

EXAMPLE 8

3,12β-Diacetoxy-20,20-ethylenedioxypregna-3,5,14-triene (21)

The diacetoxy compound (20) (60 g, 0,14 mol) is dissolved in benzene (1 l) and ethylene glycol (60 ml) and p-toluene sulfonic acid (1 g) are added. (The benzene is previously refluxed with a Dean-Stark trap). The mixture is refluxed with stirring and azeotropic removal of water for 16 hours. Aqueous saturated sodium bicarbonate solution (500 ml) is added to the cooled solution. This is then washed with brine (500 ml), and with water (500 ml), and dried (MgSO$_4$). The solvent is evaporated and the crude mixture purified by silica gel column chromatography, eluting with ethyl acetate: hexane (2:8) to yield the ethylenedioxypregna-3,5,14-triene (21) (35 g, 53%).

$^1$H NMR (CDCl$_3$): 5,68 (1H, s, H-4), 5,45 (1H, m, H-6), 5,31 (1H, dd, J=2,2 Hz, H-15), 4,73–4,85 (1H, dd, J=4,4 Hz, H-12), 3,78–3,98 (4H, m, ethylenedioxy), 2,16 (3H, s, 3-Ac), 2,04 (3H, s, 12-Ac), 1,29 (3H, s, H-21), 1,12 (3H, s, H-19), 1,02 (3H, s, H-18).

EXAMPLE 9

3β-12β-Dihydroxy-20,20-ethylenedioxypregna-5,14-diene-12-acetate (22)

The dienolacetate (21) (35g, 0,077 mol) is suspended in ethanol (500 ml) and sodium borohydride (2,8 g, 0.074 mol) is added at 0° C. The mixture is allowed to warm to room temperature and stirred overnight. Most of the solvent is removed in vacuo and the mixture is diluted with water (500 ml) and extracted with ethyl acetate (500 ml). Work-up followed by chromatography on silica gel with acetone/chloroform (1:10) yields the 39-alcohol (22) (25 g, 80%).

$^1$H NMR (CDCl$_3$): 5,41 (1H, m, H-6), 5,28 (1H, dd, J=2,2 Hz, H-15), 4,72–4,81 (1H, dd, J=4,4 Hz, H-12), 3,82–4,02 (4H, m, ethylene dioxy), 3,45–3,59 (1H, m, H-3), 2,03 (3H, s, 12-Ac), 1,28 (3H, s, H-21), 1,10 (3H, s, H-19), 1,01 (3H, s, H-18).

EXAMPLE 10

3β, 12β-Dihydroxy-20,20-ethylenedioxypregn-5,14-diene (23)

The 3β-alcohol (22) (25 g, 60.2 mmol) in dry tetrahydrofuran (300 ml) is added dropwise to a suspension of lithium aluminium hydride (2,7 g, 72,2 mmol) in dry tetrahydrofuran (500 ml). The reaction mixture is stirred at room temperature for 24 hours after which water (2,7 ml) is carefully added and stirred for a further 10 min. Sodium hydroxide (15% soln, 2,7 ml) is then added and the suspension stirred. After 10 min, water (8,1 ml) is added and the suspension stirred for 10 minutes, filtered, dried (MgSO$_4$), and the solvent evaporated to afford the 3β, 12β dihydroxypregna-diene (23) (20 g, 90%).

$^1$H NMR (CDCl$_3$): 5,36 (1H, m, H-6), 5,23 (1H, dd, J=2,2 Hz, H-15), 3,94–4,06 (4H, m, ethylene dioxy), 3,41–3,52 (1H, m, H-3), 3,32–3,36 (1H, dd, J=4,3 Hz, H-12), 1,31 (3H, s, H) 1,01 (3H, s, H-19), 0,96 (3H, s, H-18). $^{13}$C NMR (CDCl$_3$): 152,4 (c-14), 140,2 (c-S), 121,1 (c-15) 119,7 (c-6), 111,1 (C-20), 79,8 (C-12), 71,6 (C-3), 63,7 and 63,6 (ethylene dioxy), 58,8 (C-17), 19,0 (C-19), 11,9 (C-18).

3β, 12β-Dihydroxy-14,15-eloxy-20,20-ethylenedioxypregn-5-ene

3β,12β-Dihydroxy-5,6-eroxy-20,20-ethylenedioxyregn-14-ene

N-Bromoacetamide (211 mg, 1,5 mmol) is added to a stirred solution of the 5,14-diene (23) (500 mg, 1,34 mmol) in acetone (100 ml), acetic acid (2,5 ml), and water (5 ml) at 0° C. After 15 min sodium sulphite (5% soln, 50 ml) is added to the reaction mixture. The acetone is evaporated, and the aqueous layer extracted with dichloromethane (3×50 ml). The organic layer is dried (MgSO$_4$), filtered and evaporated. Pyridine (1 ml) is added to the product, and stirred for 0,5 h. Dichloromethane (100 ml) is then added to the reaction mixture, and the dichloromethane is washed with citric acid (5% soln, 3×100 ml), saturated sodium bicarbonate (50 ml), and water (50 ml). The organic layer is dried (MgSO$_4$), filtered and evaporated to give the mixture of 14,15- and 5,6-epoxides (360 mg, 69%) as a white foam. The mixture of epoxides could not be separated by silica gel column chromatography.

EXAMPLE 11

3β, 12β-Dihydroxy-14,15-epoxy-20,20-ethylenedioxypregn-5-ene (24)

The mixture of 14,15- and 5,6-epoxides (14,4 g, 37,0 mmol) in dry tetrahydrofuran (200 ml) is added to a suspension of lithium aluminium hydride (1,69 g, 44,4 mmol) in dry tetrahydrofuran (300 ml). The reaction mixture is stirred at room temperature for 24 hours, after which it is worked up as described earlier by the addition of water (1,69 ml), and sodium hydroxide (15% soln, 1,69 ml). After filtration and evaporation of the solvent, the crude product is purified by silica gel column chromatography using methanol/chloroform (1:9) as solvent to give the unreacted 14,15 epoxy-20,20-ethylenedioxypregn-5-ene (24) is (300 mg, 2,1%).

$^1$H NMR (CDCl$_3$): 5,31 (1H, m, H-6), 3,82–3,98 (4H, m, ethylene dioxy), 3,43–3,52 (1H, m, H-3), 3,41 (1H, s, H-15), 3,31–3,35 (1H, dd, J=4,3 Hz, H-12), 1,29 (3H, s, H-21), 1,17 (3H, s, H-19), 1,02 (3H, s, H-18). $^{13}$C NMR (CDCl$_3$): 139,8 (C-5), 120,8 (C-6), 112,1 (C-20), 77,2 (C-12), 75,4 (C-14), 61,0 (C-15), 22,3 (C-21), 19,2 (C-19), 9,5 (C-18).

EXAMPLE 12

3β, 12β, 14β-Trihydroxy-20,20-ethylenedioxypregn-5-ene (25)

The 14,15-epoxide (24) (300 mg, 0,77 mmol) in dry tetrahydrofuran (10 ml) is added to a suspension of lithium aluminium hydride (300 mg, 7,89 mmol) in tetrahydrofuran and the reaction refluxed for 48 h. After the addition of water (0,3 ml), sodium hydroxide (15% soln, 0,3 ml) and filtration as described earlier, the mixture is purified by silica gel column chromatography using methanol: chloroform (1:9) as solvent to give the trihydroxy pregnene (25) (250 mg, 83%).

$^1$H NMR (CDCl$_3$): 5,38 (1H, m, H-6), 3,98 (4H, m, ethylene dioxy), 3,43–3,53 (1H, m, H-3), 3,25–3,32 (1H, dd, J=4,1 Hz, H-12), 1,32 (3H, s, H-21), 1,.01 (3H, s, H-19), 0,98 (3H, s, H-18). $^{13}$C NMR CDCl$_3$): 139,1 (C-5), 122,1 (C-6), 112,2 (C-20), 85,1 (C-14), 75,1 (C-12), 71,6 (C-3), 23,4 (C-21), 19,4 (C-19), 8,9 (C-18).

EXAMPLE 13

3β, 12β, 14β-Trihydroxy-pregn-5-ene (15)

The ethylenedioxypregnene (25) (250 mg, 0,64 mmol) is dissolved in acetic acid (13,4 ml) and water which after freeze drying affords the trihydroxy steroid (15) (200 mg, 89%), m.p.: 228°–235° C. (lit 225°–235° C.), M+ 348, $[\alpha_D]^{20}$+35° (lit $[\alpha_D]^{20}$+29°).

$^1$H NMR (CDCl$_3$): 5,39 (1H, m, H-6), 3,56–3,62 (1H, t, J=8,1 Hz, H-17), 3,42–3,51 (1H, m, H-3), 3,28–3,39 (1H, dd, J=4,3 Hz, H-12), 2,23 (3H, s, H-21), 1,01 (3H, s, H-19), 0,90 (3H, s, H-18). $^{13}$C NMR (CDCl$_3$): 217,7 (C-20), 138,9 (C-5), 122,2 (C-6), 85,5 (C-14), 73,6 (C-12), 71,6 (C-3), 57,0 (C-17), 55,1 (C-13), 43,6 (c-9), 42,1 (C-4), 37,3 (C-1), 36,8 (C-10), 35,9 (C-8), 34,5 (C-15), 32,9 (C-21), 31,5 (C-16), 30,1 (C-2), 27,4 (C-7), 24,4 (C-11), 19,4 (C-19), 8,3 (C-18)

Examples 14 to 19 illllustrate the synthetic procedures whereby the intermediate compounds and steroid (15) may be prepared according to "the second alternative procedure".

EXAMPLE 14

20,20-Ethylenedioxy-3β-toluene-p-sulphonyloxy-pregn-5,14-diene-12β-ol acetate (26)

A solution of p-toluenesulphonyl chloride (650 mg, 3.4 mmol) in pyridine (10 ml) was added dropwise to a mixture of the 20,20-Ethylenedioxypregna-5,14-diene-3β,12β-diol 12-acetate (22) (1.3 g, 3.1 mmol) in pyridine (15 ml) at 0° C. The reaction mixture was left stirring at room temperature for 24 hours after which water was added to the reaction mixture. The solution was extracted with ethyl acetate (2×50 ml), the ethyl acetate layer was washed citric acid (5×50 ml), saturated sodium bicarbonate solution (100 ml), saturated sodium chloride solution (100 ml) and water (100 ml) The ethyl acetate was dried (MgSO$_4$), filtered, and evaporated and purified by flash column chromatography using hexane-ethyl acetate (8:2 v/v) as the eluant to give the β-O-tosyl steroid (26), (1.5 g, 84%), as a yellow oil, (Found M 570.271, C$_{32}$H$_{42}$O$_7$S requires: M 570.273).

δ$_H$ 1.021 (3H, s, 19-H), 1.131 (3H, s, 18-H), 1.282 (3H, s, 21-H), 2.021 (acetateOCH$_3$), 2.431 (3H, s, Ar—CH$_3$), 3.883 (4H, m, OCH$_2$CH$_2$O), 4.750 (1H, dd, $^3$ J 10.8 Hz, 5.2 Hz, 12-H), 4.890 (1H, m, 30H), 5.281 (1H, dd, $^3$ J 4.2 Hz, 2.1 Hz, 15-H), 5.388 (1H, m, 6-H), 7.341 (2H, d, $^3$ J 8.2 Hz, ArH), 7.746 (2H, d, $^3$ J 8.2 Hz, ArH). δ$_C$ 13.493Q (C-18), 19.002Q (C-19), 21.612Q (Ar-methyl)*, 21.671Q (C-21)*, 24.175Q (acetate methyl), 63.401T (ethylenedioxy), 63.498T (ethylenedioxy), 71.531S (C-13), 80.912D (C-12), 82.531D (C-3), 111.363S (C-20), 120.881D (C-15), 121.461D (C-6), 123.715– 133.917 (Aromatic), 139,903S (C-14), 151,722S (C-5), 170.819S (ester carbonyl).
*may be interchanged

EXAMPLE 15

20,20-Ethylenedioxy-3α, 5-cyclo-5α-pregn-14-ene-6β, 12β-diol-12-acetate (27)

A solution of 3β-toluene-p-sulphonyloxy-pregn-5,14-diene (26) (1.2 g, 2.1 mmol) and potassium acetate (2.2 g, 22.4 mmol) in water (250 ml) and acetone (500 ml) was refluxed at 60° C. for 16 hours. The acetone was evaporated and the water was extracted with ethyl acetate (200 ml). The ethyl acetate was dried (MgSO$_4$), filtered, and evaporated. Flash chromatographic separation of the mixture using chloroform-acetone (9:1 v/v) as the eluant gave the 3α,5-cyclo derivative (27), (530 mg, 61%) as a yellow oil, (Found M 416.262, C$_{25}$H$_{36}$O$_5$ requires: M 416.263).

δ$_H$ 0.288 (1H, dd, $^3$ J 8.1 Hz, 4.9 Hz, 4H$_a$), 0.477 (1H, dd, $^3$ J 4.4 Hz, 4.4 Hz, 4-H$_b$), 1.025 (3H, s, 19-H), 1.121 (3H, s, 18-H), 1.256 (3H, s, 21-H), 1.989 (3H, s, acetate-CH$_3$), 3.302 (1H, dd, $^3$ J 2.8 Hz 2.8 Hz, 6-H), 3.784–3.947 (4H, m, OCH$_2$CH$_2$O), 4.721 (1H, dd, $^3$ J 8.5 Hz, 5.6 Hz, 12-H), 5.232 (1H, dd, $^3$ J 3.9 Hz, 1.9 Hz, 15-H). δ$_C$ 11.678T(C-4), 12.298Q(C-18), 19.971Q (C-19), 23.623Q(C-21), 24.153Q (acetate methyl), 63.700T (ethylenedioxy), 63.788T (ethylenedioxy), 73.591D (C-6), 80.551D (C-12), 111.126S (C-20), 118.778D (C-15), 152.959S (C-14), 170.991S (ester carbonyl).

EXAMPLE 16

20,20-Ethylenedioxy-3α, 5-cyclo-5α-pregn-14-ene-6β, 12β-diol (28)

A solution of the 3β,5-cyclo derivative (27), (500 mg, 1.2 mmol) in tetrahydrofuran (20 ml) was added dropwise to a suspension of lithium aluminium hydride (50 mg, 1.3 mmol) in tetrahydrofuran (10 ml). The reaction mixture was stirred for 4 hours and quenched by the addition of water (50 μl). After 30 minutes, sodium hydroxide was added (15% solution, 50 μl) and stirring continued for a further 30 minutes. Water (150 μl was added and the reaction mixture was filtered. The tetrahydrofuran was dried (MgSO$_4$) filtered and evaporated and flash chromatographic purification using chloroform-acetone (8:2 v/v) as the eluant to give the diol (28), (370 mg, 83%) as an oil, (Found M 374.250, C$_{23}$H$_{34}$O$_4$ requires: M 374.252)

$\delta_H$ 0.298 (1H, dd, $^3$ J 8.1 Hz, 4.9 Hz, 4-H$_2$), 0.510 (1H, dd, $^3$ J 4.4 Hz, 4.4 Hz, 4-Hb), 0.985 (3H, s, 19-H), 1.055 (3H, s, 18-H), 1.325 (3H, s, 21-H), 3.318 (1H, dd, $^3$ J 3.0 Hz, 3.0 Hz, 6-H),), 3.363 (1H, dd, 3 J 11.4 Hz, 4.2 Hz, 12-H), 4.019 (4H, m, OCH$_2$Ch$_2$O) 4.622 (1H, s, OH), 5.255 (1H, dd, $^3$ J 3.9 Hz, 1.9 Hz, 15-H). $\delta_C$ 11.681T(C-4), 12.243Q(C-18), 19.844Q (C-19), 23.604Q(C-21), 63.620T (ethylenedioxy), 63.733T (ethylenedioxy), 73.569D (C-6), 77.478D (C-12), 111.125S (C-20), 118.702D (C-15), 152.912S (C-14).

EXAMPLE 17

20, 20-Ethylenedioxy-14, 15β-epoxy-3α,5-cyclo-5α, 14β-pregnane-6β,12β-diol (29)

N-bromoacetamide (150 mg, 1.1 mmol) was added to a solution of the 20,20-ethylenedioxy-3α,5-cyclo-5α-pregn-14-ene-6β,12β-diol (28) (340 mg, 0.91 mmol) in acetone (20 ml), water (0.25 ml) and acetic acid (0.25 ml) at 0° C. After 15 min., sodium sulphite (5% solution, 20 ml) was added to the reaction mixture. The acetone was evaporated under reduced pressure and the remaining solution was extracted with dichloromethane (3×30 ml). The dichloromethane layer was dried (MgSO$_4$), filtered and evaporated to a concentrated volume (50 ml). Pyridine (0.5 ml) was added to the mixture and stirred for a further 1 hour after which the dichloromethane layer was washed with a citric acid solution (5%, 3×30 ml), saturated sodium bicarbonate solution (30 ml) and water (30 ml). The dichloromethane layer was dried (MgSO)$_4$), filtered and evaporated and purified by flash column chromatography using chloroform-methanol (9.5:0.5 v/v) as the eluant to give the epoxide (29) (180 mg, 51% as a foam, (Found M 390.245, C$_{23}$H$_{34}$O$_2$ requires: M 390.247).

$\delta_H$ 0.287 (1H, dd, $^3$ J 8.1 Hz, 4.9 Hz, 4H$_a$), 0.501 (1H, dd, $^3$ J 4.4 Hz, 4.4 Hz, 4-H$_b$), 0.978 (3H, s, 19-H), 1.048 (3H, s, 18-H), 1.321 (3H, s, 21-H), 3.318 (1H, dd, $^3$ J 3.1 Hz, 3.1 Hz, 6-H), ), 3.355 (1H, dd, $^3$ J 11.2 Hz, 4.1 Hz, 12-H), 3.491 (1H, s, 15-H), 4.001 (4H, m, OCH$_2$Ch$_2$O), 4.901 (1H, s, OH) $\delta_C$ 11.668T(C-4), 11.973Q(C-18), 19.515Q (C-19), 23.519Q (C-21), 59.910D (C-15), 63.601T (ethylenedioxy), 63.713T (ethylenedioxy), 72.501S (C-14), 73.571D (C-6), 77.471D (C-12), 111.085S (C-20).

EXAMPLE 18

20,20-Ethylenedioxy-6β,12β, 14-trihydroxy-3α,5-cyclo-5α, 14β-pregnane (30)

A solution of the epoxide (29) (170 mg, 0.44 mmol) in tetrahydrofuran (10 ml) was added to a suspension of lithium aluminium hydride (20 mg, 0.53 mmol) in tetrahydrofuran (5 ml). The reaction mixture was refluxed for 2 hours after which water (20 μl) was added and stirring continued for 05 hour. Sodium hydroxide solution (15%, 20 μl) was added and stirring continued for a further 0.5 hour. A further quantity of water was added (60 μl) and the suspension was stirred for 1 hour. After filtration, the suspension was dried (MgSO$_4$) filtered, and the tetrahydrofuran was evaporated. Flash chromatographic separation of the resulting mixture eluting with chloroform-methanol (9:1 v/v) gave the required triol (30), 90 mg, 53%) as a clear oil, (Found M 392.261, C$_{23}$H$_{38}$O$_5$ requires: M 392.263).

$\delta_H$ 0.287 (1H, dd, $^3$ J 8.1 Hz, 4.9 Hz, 4-H$_2$), 0.510 (1H, dd, $^3$ J 4.4 Hz, 4.4 Hz, 4-H$_b$), 0.971 (3H, s, 19-H), 1.042 (3H, s, 18-H), 1.319 (3H, S, 21-H), 3.321 (1H, dd, $^3$ J 3.0 Hz, 3.0 Hz, 6-H), 3.321 (1H, dd, $^3$ J 11.1 Hz, 3.9 Hz, 12-H), 3.561 (1H, s, OH), 4.084 (4h, m, OCH$_2$Ch$_2$O) 4.671 (1H, S, OH). $\delta_C$ 11.668T(C-4), 11.971Q(C-16), 19.511Q (C-19), 23.520Q (C-21), 63.612T (ethylenedioxy), 63. 711T (ethylenedioxy), 73.483D (C-6), 76.051D (C-12), 84.307S (C-14), 111.099S (C-20).

EXAMPLE 19

3β, 12β, 14-Trihydroxy-14β-pregn-5-en-20-one (15)

A mixture of the triol (30) (80 mg, 0.20 mmol) in acetone (20 ml) and hydrochloric acid (1M, 10 ml) was refluxed at 60° C. for 2 hours. The reaction mixture was cooled and saturated sodium bicarbonate solution (20 ml) was added. The acetone was evaporated and the aqueous layer extracted with chloroform (3×20 ml), the chloroform layer was dried (MgSO$_4$), filtered and evaporated to give the epimeric trihydroxy steroids (15a, 15b) (42 mg, 61%). Separation of the epimeric mixture (15a, 15b) (15 mg) was achieved by flash chromatographic separation using chloroform:methanol (9:1 v/v) as the eluant to give the pure 17β-epimer (15a), (10 mg), m.p. 224–229° C. (acetone), (lit. 226–223°), (Found M 348.234, C; 72.32, H 9.21% C$_{21}$H$_{32}$O$_4$ requires: C, 72.38; H 9.26%, M 348.236), and the 17α-epimer (15B) (3 mg), m.p. 183–1910C (acetone), (lit 184–1960).

3β,12β,14-Trihydroxy-14β-pregn-5-en-20-one (15a)

$\delta_H$ 0.963 (1H, s, 19-H), 1.192 (3H, s, 18-H), 2.236 (3H, s 21-H), 3.325 (1H, dd, $^3$ J 11 2 Hz, 3.9 Hz, 12-H), 3.464 (1H, s, OH), 3.5140 (1H, m, 3-H), 3.598 (1H, dd, $^3$ J 9.6 Hz, 9.6 Hz, 17-H), 4.255 (1H, s, OH), 5.383 (1H, m, 5-H). $\delta_C$ 8.275Q (C-18), 19.414Q (C-19), 24.400T (C-11) 24.581T (C-16), 27.443T (C-7), 30.062T (C-2), 32.972Q (C-21), 34.543T (C-15), 35.864D (C-8), 36.975S (C-10), 37.337T (C-1), 42.144T (C-4), 43.565D (C-9), 55.101S (C-13), 57.038D (C-17), 71.597D (C-3), 73.558D (C-12), 85.566S (C-14), 122.223D (C-6), 138.932S (C-5), 217.011S (C-20).

3β,12β,14-Trihydroxy-14β-pregn-5-en-20-one (15b)

$\delta_H$ 0.996 (1H, s, 19-H), 1.144 (3H, s, 18-H), 2.221 (3H, S 21-H), 3.339 (1H, dd, $^3$ J 9.4 Hz, 9.4 Hz, 17-H), 3.492 (1H, m, 3-H), 3.629 (1H, dd, $^3$ J 11.1 Hz, 3.9 Hz, 12-H), 3.712 (1H, s, OH), 4.325 (1H, s, OH), 5.383 (1H, m, 5-H).

Examples 20 to 28 illustrate the procedures whereby the intermediate compounds may be prepared to form the first monosaccharide (40).

EXAMPLE 20

Methyl-4,6-0-benzylidene-α-D-glucopyranoside (32)

A mixture of methyl-α-D-glucopyranoside (30 g, 0,15 mol), benzaldehyde (70 ml) and zinc chloride (20 g) is stirred at room temperature for 24 hours. The reaction product is poured into ice water and stirring continued for 15 min. The white precipitate is filtered and washed with diethyl ether. The solid material is stirred with a solution of sodium metabisulphite (10% soln), for 15 min, filtered and washed with water. The solid material is crystallized from chloroform and ether to yield the benzylidene product (32) (31 g, 72%)

EXAMPLE 21

Methyl-4,6-0-benzylidene-2-0-tosyl-α-D-glucopyranoside (33)

p-Toluene sulfonyl chloride (25 g, 1,2 eq) in pyridine (100 ml) is added dropwise to a solution of the benzylidene glucose (32) (31 g, 0.12 mol) in pyridine (100 ml) at 0° C. The reaction is stirred at room temperature for 48 hours. Ice is added to the reaction mixture. The resulting white solid material is washed with water and recrystallized from hot ethanol to yield the tosylated glucose (33) (28 g, 60%).

EXAMPLE 22

Methyl-4,6-0-benzylidene-3-0-methyl-α-D-altropyranoside (34)

The tosylate (33) (28 g, 64 mmol) in a solution of sodium (7 g) in methanol (150 ml) is heated at 110° C. for 48 hour in an autoclave. The reaction vessel is cooled and solid carbon dioxide is added to the reaction mixture. After filtration, the methanol is evaporated and the solid material is then taken up in water. The aqueous layer is extracted with chloroform (×3). The chloroform is dried (MgSO$_4$), filtered and evaporated. The crude mixture is purified by silica gel column chromatography eluting with chloroform:acetone (9:1) to yield the altroside (34) (10 g, 52%)

EXAMPLE 23

Methyl-6-bromo-4-0-benzoyl-3-0-methyl-6-deoxy-α-D-altropyranoside (35)

The benzylidene altroside (34) (10 g, 33 mmol) is added to a solution of N-bromosuccinimide (7.6 g) and barium carbonate (20 g) in carbon tetrachloride and the reaction mixture is refluxed at 75° C. for 3 hours. The reaction mixture is filtered and the carbon tetrachloride layer is washed with water. The organic layer is dried (MgSO4), filtered and evaporated to yield 6-bromo-altroside (35), (9 g, 69%).

EXAMPLE 24

Methyl-4-0-benzoyl-3-0-methyl-6-deoxy-α-D-altrolyranoside (36)

Sodium borohydride (18 g) in water (30 ml) is added dropwise to a solution of the bromoaltroside (35) (9 g, 23 mmol) and nickel chloride (18 g) in ethanol (300 ml) at 0° C. The reaction mixture is refluxed at 75° C. for 1 hour and then it is filtered. The ethanol is evaporated and the remaining aoueous layer is extracted with chloroform (×3). The chloroform is dried (MgSO$_4$), filtered and evaporated, to yield the 6-deoxy-altroside (36) (5 g, 72%)

EXAMPLE 25

4-0-Benzoyl-3-0-methyl-6-deoxy-αβ-D-phenylthioaltropyranoside (37)

Phenylthiotrimethylsilane (5 ml) and trimethylsilyltrifluoromethane sulphonate (2 ml) are added at 0° C. to a solution of the 6-deoxy-altroside (36) (5 g, 17 mmol) in dichloromethane (200 ml). The reaction mixture is stirred at room temperature for 6 hours. Saturated sodium bicarbonate is added to the reaction mixture. The dichloromethane layer is dried (MgSO$_4$), filtered and evaporated. The crude mixture is purified by silica gel column chromatography eluting with chloroform:acetone (9:1) to yield the αβ-phenylthioaltroside (37) (4 g, 63%)

EXAMPLE 26

4-0-Benzoyl-3-0-methyl-2-phenylthio-2,6-dideoxy-αβ-D-fluorocymaronyranoside (38)

Diethylaminosulphurtrifluoride (0,65 g) is added rapidly to a solution of the αβ-phenylthioaltroside (37) (0,5 g, 1,33 mmol) in dichloromethane at 0° C. The reaction is stirred for 0,5 h at 0° C. and then saturated sodium bicarbonate is added. The dichloromethane is separated from the aqueous layer, dried (MgSO$_4$), filtered and evaporated to yield the αβ-fluorocymarose (38) (450 mg, 90%).

EXAMPLE 27

4-0-Benzoyl-3-0-methyl-2-0-t-butyldimethylsilyl-αβ-D-phenylthio-altroside (39)

The 6-deoxy altroside (37) (5 g) is silylated using t-butyldimethylsilylchloride (3 g) and imidazole (3 g) in pyridine (50 ml). The reaction is worked-up by extracting with ethyl acetate, washing the ethyl acetate with hydrochloric acid (6 N), then with sodium bicarbonate, and finally with water. The ethyl acetate layer is dried (MgSO$_4$), filtered and evaporated to yield the silylated benzoyl phenylthioaltroside (39) (80%).

EXAMPLE 28

3-0-methyl-2-0-t-butyldimethylsilyl-αβ-D-phenylthioaltroside (40)

The silylated benzoyl phenylthioaltroside (39) (6 g) is treated with sodium methoxide (100 ml) for 4 hours. The methanol is evaporated and water is added to the reaction. The water layer is acidified (pH 5, ACOH) and extracted with ethyl acetate. The ethyl acetate is washed with water, dried (MgSO$_4$), filtered and evaporated to yield silylated methyl phenylthioaltroside (40) (75%).

Examples 29 to 37 illustrate the procedures synthetic whereby the intermediate compounds may be prepared to form the second monosaccharide (50).

EXAMPLE 29

1,2: 5,6-Di-O-isopropylidene-α-D-glucofuranose (42)

Sulfuric acid (40 ml) is added dropwise to a solution of α-D-glucose (41) (50 g, 0,28 mol) in acetone (1 l) at 0° C. The reaction mixture is stirred for 24 h and then it is neutralized using sodium hydroxide (6 M). The acetone is evaporated and the aqueous layer is extracted with chloroform (X2). The chloroform is dried (MgSO$_4$) filtered and evaporated. Crystallization from cyclohexane yielded the di-isopropylidene glucose (42) (41 g, 57%).

EXAMPLE 30

1,2: 5,6-Di-O-isopropylidene-3-0-methyl-α-D-glucofuranose (43)

The α-D-glucofuranose (42) (41 g, 0,16 mol) in tetrahydrofuran (300 ml) is added dropwise to a suspension of sodium hydride (5 g) in tetrahydrofuran (200 ml). After 0,5 h, methyl iodide (25 g) in tetrahydrofuran (100 ml) is added dropwise to the reaction mixture which is then stirred for 24 h. Water is added to the reaction mixture which is then extracted with ether (×3). The ether layer is dried (MgSO$_4$), filtered and evaporated to yield the methyl protected glucose (43) (38 g, 83%).

EXAMPLE 31

3-0-Methyl-αβ-D-glucocyranoside (44)

The methyl diisopropylidene compound (43) (38 g, 0,14 mol) is dissolved in acetic acid (50%, 700 ml) and the solution refluxed for 18 h. After cooling the acetic acid is evaporated. The crude product is purified by column chromatography eluting with chloroform:methanol:acetone:water (70:27:2 1) to yield 3-0-methyl-αβ-glucopyranoside (44) (13 g, 50%).

EXAMPLE 32

Methyl 3-0-methyl-αβ-D-glucoyranoside (45)

The 3-0-methyl-αβ-glucopyranoside (44) (10 g) is dissolved in methanol (50 ml) and HCl (conc.) (1 ml) and refluxed overnight. Solid NaHCO$_3$ is added and the reaction is filtered. The methanol is evaporated to give 1,3-di-0-methyl-αβ-D-glucopyranoside (45), (95%).

EXAMPLE 33

Methyl 4,6-0-benzylidene-3-0-methyl-αβ-glucopyranoside (46)

The glucopyranoside (45) (8 g) is stirred at room temperature in a solution of benzalaldehyde (20 ml) and zinc chloride (5 g). After 24 hours, ice is added and the aqueous layer is extracted with chloroform. The chloroform layer is dried (MgSO$_4$), filtered and evaporated. The benzalaldehyde is removed by vacuum distillation and the product is purified by silica gel column chromatography eluting with acetone:chloroform (0,5:9,5), to yield benzylidene-αβ-glucopyranoside (46) (60%).

EXAMPLE 34

Methyl 4-0-benzoyl-0-methyl-6-deoxy-αβ-glucopyranoside (47)

The benzylidene compound (46) (5 g) is refluxed at 80° C. in a mixture of N-bromosuccinimide (3,7 g) and barium carbonate (4 g) in carbon tetrachloride. After 4 hours, the reaction is filtered and the carbon tetrachloride is washed with water, dried (MgSO$_4$), filtered and evaporated to give the bromo compound (70%).

The bromo compound (4,3 g) is dissolved in a solution of ethanol (300 ml) and nickel chloride (8,6 g) at 0° C. To this solution, sodium borohydride (8,6 g) in water (50 ml) is added dropwise over a period of 15 minutes. The reaction mixture is refluxed at 100° C. for 45 minutes, cooled, filtered and evaporated. Chloroform is added, and the chloroform layer is washed with water, dried (MgSO$_4$), filtered and evaporated to give the 6-deoxy sugar (47) (70%).

EXAMPLE 35

4-0-Benzoyl-3-0-methyl-1-phenylthio-6-deoxy-αβ-glucolyranoside (48)

The 6-deoxy glucopyranoside (47) (3 g) is dissolved in dichloromethane (50 ml). To this solution, phenylthiotrimethylsilane (2 g) and trimethylsilyltrifluoromethanesulphonate (0,2 ml) are added. The solution is stirred at room temperature overnight, after which saturated sodium bicarbonate is added. The dichloromethane layer is dried (MgSO$_4$), filtered and evaporated. The product is purified by silica gel column chromatography eluting with ethyl acetate:hexane (2:8), to give the compound (48) (60%).

EXAMPLE 36

4-0-Benzoyl-3-0-methyl-2-0-pivaloyl-1-Phenylthio-6-deoxy-αβ-glucopyranoside (49)

To a solution of the glucopyranoside (48) (2 g) in pyridine (20 ml), pivaloyl chloride (2 ml) is added. The solution is stirred at room temperature overnight after which water is added. The aqueous layer is extracted with ethyl acetate, and the organic layer is washed with HCl (6 N). The organic layer is dried (MgSO$_4$), filtered and evaporated to give the pivaloyl ester (49) (80%).

EXAMPLE 37

4-0-Benzoyl-3-0-methyl-2-0-Pivaloyl-1-fluoro-6-deoxy-β-alucocranoside (50)

N-Bromosuccinimide (1,2 g) and diethylaminosulphur trifluoride (1,2 g) are added to a solution of the pivaloyl ester (49) (2 g) in dichloromethane (100 ml) at 0° C. After 1 hour, saturated sodium bicarbonate is added. The dichloromethane layer is dried (MgSO$_4$), filtered and evaporated. The β-fluoropyranoside (50) is purified by silica gel column chromatography eluting with ethyl acetate:hexane (2:8), (yield 45%).

Example 38 illustrates the synthetic procedure whereby the compound 3-0-[4-0-benzoyl-2-phenylthio-β-D-cymaropyranosyl]-12,14β-dihydroxy-pregnan-5-ene-20-one(51) may be prepared.

EXAMPLE 38

3-0-[4-0-benzoyl-2-phenylthio-β-D-cymaropyranosyl]-12,14β-dihydroxy-pregn-5-en-20-one (51)

Tin chloride (190 mg, 1 mmol) is added to a solution of 3,12,14β-trihydroxy pregnan-5-ene-20-one (15) (100 mg, 0,28 mmol) and the fluorocymaropyranoside (38) (210 mg, 0,56 mmol), in dry diethyl ether and 4 Å molecular sieves at −15° C. The reaction mixture is maintained at −15° C. for 3 days. Saturated sodium bicarbonate is added to the reaction mixture. The ether layer is dried (MgSO$_4$), filtered and evaporated. The product is purified by silica gel column chromatography eluting with chloroform : methanol (9, 5:0,5) to yield the glycoside (51) (30 mg, 15%).

Examples 39 to 41 illustrate the synthetic procedures whereby the cymarose and thevetose moieties may be coupled.

EXAMPLE 39

Thevetose-cymarose dissaccharide (53)

A solution of thevetose (50 A) (1,5 g), cymarose (40) (1,3 g), and molecular sieves 4 Å in dichloromethane is stirred at room temperature for 1 hour. The reaction mixture is cooled to −15° C., and tin (II) chloride (0,8 g) and silver trifluoromethanesulphonate (1,1 g) are added. The mixture is stirred at −15° C. for 16 hours, after which triethylamine (0,5 ml) is added. The reaction product is filtered and the dichloromethane is evaporated. The dissaccharide (53) is purified by silica gel column chromatography eluting with ethyl acetate:hexane (2:8), yield 15%.

EXAMPLE 40

Thevetose-cymarose dissaccharide (54)

To a solution of the dissaccharide (53) (200 mg) in tetrahydrofuran (20 ml), tetrabutylammonium fluoride (0,4 ml) is added. The mixture is stirred at room temperature for 1 hour, after which saturated sodium bicarbonate is added. The reaction mixture is extracted with ethyl acetate and the ethyl acetate layer is dried (MgSO$_4$), filtered and evaporated.

The dissaccharide (54) is purified by silica gel column chromatography (acetone:chloroform, 0,5:9,5) yield 60%.

EXAMPLE 41

Thevetose-cymarose dissaccharide (55)

To a solution of the dissaccharide (54) (80 mg) in dichloromethane (10 ml), diethylamino sulphur trifluoride (80 μl) is added at 0° C. After stirring at 0° C. for 0,5 hour, saturated sodium bicarbonate and more dichloromethane are added. The dichloromethane is dried ($MgSO_4$), filtered and evaporated. Purification by silica gel column chromatography (ethyl acetate:hexane 1:9), gives the dissaccharide (55) in a 65% yield.

EXAMPLE 42

The results of the following three bioassays on the appetite suppressant are set out below, viz.
a) Irwin Test;
b) Acute Toxicity Test; and
c) Oral Dose Anorectic Test.

a) Irwin Test

The purpose of this test was to evaluate the appetite suppressant of the invention produced from a plant extract as hereinbefore described, according to the reduced animal Irwin test for tranquillising and sedative action.
Experimental Procedure The appetite suppressant was extracted from plant material by the Applicant by the method as hereinbefore described and administered to two of four groups of three animals each: one group receiving no treatment, one group receiving the solvent dimethylsulfoxide (DMSO), one group receiving the test sample at 50 mg/kg, and one group receiving the test sample at 300 mg/kg. Treatment took place by intraperitoneal injection, and observations were made at specific intervals up to five hours post treatment. Only symptoms other than those observed in the DMSO-treated animals were used in the interpretation of the results.
Results It was clear that the solvent, DMSO, had a marked is effect on the animals, especially on the heat regulating mechanism. Body temperatures of all the animals treated with the solvent, alone or together with the test sample, showed a marked drop.

Animals in the low dose group showed decreased dispersion in the cage and decreased locomotor activity, as in all the other groups, including the control group. Apathy was seen in the same degree as in the DMSO-treated group. Decreased respiration was observed 15–60 minutes after treatment. Ptosis (closing of the eyelids) was also observed to a larger degree than in the DMSO group. A pinna (ear) response was seen as well as a positive finger response, indicating fearfulness. Body temperature dropped to 32,7° C. after treatment.

Animals in the high dose group showed as in the other groups an initial decreased dispersion in the cage and decreased locomotor activity, but showed increased dispersion and locomotor activity before death, which occurred approximately 1 hour after treatment. Severe clonic symmetrical convulsions occurred 30 minutes after treatment. Respiration decreased initially, but increased before death. A pinna (ear) response was delayed and a positive finger response was observed, indicating fearfulness, both as observed in animals in the low dose group. Body temperature dropped to 30,7° C. after treatment. Increased positional passivity was observed as well as decreased body tone. Abnormal limb rotation was observed, the grip strength decreased, no pain response was present and loss of righting reflex occurred.
Discussion When compared with the control and DMSO-treated animals, animals receiving the low dose (50 mg/kg) only showed decreased respiration and an increased degree of ptosis. Animals receiving the high dose (300 mg/kg) of the test sample reacted very intensely by showing convulsions and death. All other observations made in these animals can be ascribed to the animals being in convulsions and dying. Signs suggestive of tranquillising and sedative actions such as marked decreased dispersion in the cages, decreased locomotor activity and apathy in the test groups that could be ascribed to the test sample were not seen.

It can therefore be concluded that the test sample is lethal to mice at 300 mg/kg and has respiratory suppressive effects on mice at 50 mg/kg, when given intraperitoneally with DMSO as solvent.

b) Acute Toxicity Test

The purpose of this test was to gain information on the toxicity of the test sample.
Experimental Procedure A plant extract prepared in accordance with the invention as hereinbefore described, and having appetite suppressive action was purified and one test sample was tested at increasing doses by oral treatment in mice. Two animals were used per dose group, except in the highest dose group where only one animal was treated. Animals were examined for good health and their body masses determined on the day of treatment.

Doses ranged from 100 mg/kg up to 3 028,5 mg/kg. The dose was calculated and mixed into prepared potato starch, so that each animal received a total dose of 0,2 ml. Animal 13 received 0,25 ml. Potato starch was prepared by mixing 20 g starch into a small volume of cold water, and adding it to boiling water, to make up a volume of 1 litre. The suspension was allowed to cool to room temperature before dosing.

Animals in groups 1 and 2 were treated on the same day. They were observed for 24 hours and if no signs of toxicity developed, the next group was treated. The same approach was followed until all the animals were treated. This schedule was followed to ensure that animals were not unnecessarily treated when an acute toxic dose had been reached in the previous group.

Animals were observed for clinical signs of toxicity immediately (1–2 hours) after treatment and daily thereafter. Body mass was determined once a week and total food and water intakes of each animal were measured. Surviving animals were euthanased by intraperitoneal injection of pentobarbitone sodium (commercially available under the trade name Euthanaze, Centaur®) on day 14 of the experiment. A post-mortem examination was performed on these animals, as well as on the one animal which died during the experiment. Samples for histopathology were collected.
Results
Group 1 (Control Group)

No clinical signs of toxicity were observed during the 14-day observation period. Food and water intakes were within the normal parameters. Changes in body mass were also within normal parameters. No histopathological changes were recorded in the liver samples.

Group 2 (100 mg/kg)

No clinical signs of toxicity were observed during the observation period. Food and water intakes were normal and changes in body mass over the observation period were also normal. No macroscopical pathology was observed and no histopathological or morphological changes were recorded in the liver samples.

Group 3 (200 mg/kg)

Animals in this group showed no clinical symptoms of toxicity during the experiment. Food and water intakes were normal, as was the change in body mass. No macroscopic pathology was observed, but the livers showed histopathological changes on examination. Cloudy swelling of the hepatocytes was mild in animal 6, but moderate in animal 5. Moderate hydropic degeneration also occurred in the hepatocytes of animal 5.

Group 4 (400 mg/kg)

No clinical signs of toxicity were observed during the observation period, and no macroscopic pathology was observed during the post-mortem examination. Moderate cloudy swelling and mild hydropic changes of the hepatocytes were observed on histology.

Water and food intakes and the increase in body mass in animal 7 were normal. Animal 8 consumed almost double the total food intake of animal 7 (144,6 g and 73,9 g respectively), but the increase in body mass was only 0,81 g compared to 2,7 g.

Group 5 (800 mg/kg)

One animal (animal 10) died three hours after dosing without showing any specific signs. The other animal (animal 9) survived the entire observation period without any signs of toxicity. Water intake in the surviving animal was normal (42,42 ml), while food intake was high (134,2 g). The body mass increased by 2,85 g which was the highest of all animals in the experiment.

At the postmortem examination of animal 10, which died shortly after oral dosing, the lungs were congested. No foreign body reaction which would have indicated inhalation of test material was present. No macroscopic pathology was observed in animal 9. Mild cytoplasmic vacuolisation (hydropic degeneration) was present in animal 10, but moderate in animal 9. The glandular cytoplasmic appearance of the liver was classified as moderate in both animals Group 6 (1 600 mg/kg)

None of the animals presented any clinical signs of toxicity during the duration of the experiment. No macroscopic pathology was observed at post-mortem examination, but moderate degenerative changes in the liver of animal 11 were observed at histopathological examination. Animal 12 showed moderate cloudy swelling and mild hydropic changes of the hepatocytes. Food and water intakes were normal, as was the increase in body mass over the experimental period.

Group 7 (3 028,5 mg/kg)

Only one animal was treated at this dose. This animal showed no signs of toxicity during the observation period, and no macroscopic pathology was observed. At histopathological examination, moderate cloudy swelling and hydropic degeneration of the hepatocytes was observed. The animal showed a loss of body mass over the observation period (−0,82 g), but food and water intakes were normal.

Discussion

Since a very small number of animals were used in each dose group, it is difficult to make any conclusions. The fact that only one animal died at a low dose rate, without showing any symptoms, might indicate that death was not related to the test sample, but due to stress during and/or after treatment. No animals in higher dose groups died or showed any signs of toxicity, which further supports this assumption.

The increased food intake observed in animal 8 could possibly be ascribed to excessive spillage of food as was reflected in the small increase in body mass. It should be kept in mind that all the animals in this experiment were only treated once, and that it is unlikely that an appetite suppressor will have a marked influence on either the food or water intakes, or body mass over a 14 day period, as was the case in this experiment.

From the histopathological examination of the liver samples, it was clear that the pathological changes were dose related, with animals receiving higher doses showing the extensive changes. The pathology observed was not metabolic of nature, but possibly test sample-induced. The changes were only degenerative and therefore reversible. No signs of irreversible hepatocellular changes were observed.

It can, therefore, be concluded that only one animal died at a lower dose (800 mg/kg), but that the death was possibly not test sample related. None of the other animals in any of the dose groups showed any signs of toxicity during the 14 day observation period after treatment, or died as result of the treatment. A single oral dose of the test sample induced reversible dose-related hepatocellular changes.

c) Oral Dose Anorectic Test

The purpose of this test was to determine the activity of a plant extract prepared in accordance with the invention, and the minimum effective dose, and at the same time investigate any possible side-effects such as respiratory suppression, as experienced in the Irwin Test (referred to above).

Experimental Procedure

Animals were allocated to treatment groups using randomisation tables. Each treatment group consisted of three animals, with 6 animals in the control group The test sample was dosed to young female rats with body weight 100–150 g at acclimatisation, for three consecutive days. Animals were identified by means of metallic ear tags and $KMnO_4$ skin markings for easy identification. Animals were housed individually in standard rodent polycarbonate cages, and water and powdered commercial rodent pellets were available ad libitum. Water and food intakes were measured and calculated for each day. In order to find the minimum effective dose of the test sample, five doses were tested. Treatment was by oral gavage, with the test sample suspended in potato starch.

The test substance was compound (1), a white granular powder prepared from an extract from plant material in accordance with the invention, and the measured quantity of the test sample was mixed with prepared potato starch and dosed. Mixing with potato starch took place immediately before dosing on each day. Before withdrawal of the dosing volume for each animal, the suspensions were mixed thoroughly using a Vortex.

A range of five doses was tested, with a control group receiving only the carrier substance. Doses were chosen on the basis of the effects observed in the aforedescribed Irwin Test and were:

Group 1: 0,00 mg/kg (Control Group)
Group 2: 6,25 mg/kg
Group 3: 12,50 mg/kg
Group 4: 25,00 mg/kg
Group 5: 37,50 mg/kg
Group 6: 50,00 mg/kg Results Treatment did not affect the health of the animals during the study period. Animals treated with the test sample in all dose groups, showed a significantly reduced mean body mass gain over the total study period, and animals in three of the five treatment groups actually lost body mass.

Mean food intakes for all the treatment groups were reduced over the study period. Animals in the higher dose groups showed an increased water consumption.

Respiratory rate in none of the animals in any dose group was significantly effected.

Animals in all dose groups presented with friable livers at post-mortem examination, but no macroscopic pathology was observed.

Discussion

Data collected during the acclimatisation period confirmed that all animals included in the experiment were healthy and body mass gain was comparable between the animals.

The reduction, and in some animals even a loss, in body mass gain, in combination with the reduced food intake is strongly indicative of suppression of the appetite centre.

Reduced food intake and reduced body mass gain was experienced even with the lowest dose group (6,25 mg/kg). Actual loss in body mass was experienced in the 12,50 mg/kg group.

It is important to note that the treatment groups all had an increased water consumption when feed consumption decreased (FIG. 2). This could be due to a diuretic effect of the test sample, or to stimulation of the thirst centre in the brain.

The fact that no respiratory suppression occurred as had been observed in the acute toxicity test referred to above, with the intraperitoneal route, is seen as a positive aspect. This could be due to reduced absorption from the gastrointestinal tract, with consequent reduced bioavailability. The bioavailability at the oral doses tested was, however, sufficient for the test sample to be effective. The slight reduction in respiratory rate 1 hour post treatment in most groups could be ascribed to filling of the stomach with the dose volume and consequent passivity of the animals.

The friable livers observed in the treatment groups could be due to a change in the energy metabolism secondary to the reduced food intake, causing increased fat metabolism and overload on the liver. If this was indeed the case, these changes could possibly be regarded these changes as transitory which might recover with time after a steady state had been reached, or after withdrawal of the test sample. The possible effect on the liver also needs further investigation.

Since this study was intended primarily as a screening test, small groups of test animals were used. This makes statistical interpretation of the data difficult, especially where individual animals react totally differently. However, the data indicates that the test sample has appetite suppressive action, even at the lowest dose tested (6,25 mg/kg) No clinical signs of respiratory suppression occurred at the doses tested.

EXAMPLE 43

Harvested Hoodia plants received either from the natural environment or through a cultivation programme are first stored at 4° C. for a maximum of 48 hours. The plants are washed in tap water and thereafter sliced into ±1 cm slices. The sliced pieces are all combined and then pressed through a hydraulic press at 300 bar pressure for a minimum of 0.5 hour per pressing. During the pressing the sap of the plant is collected separately. The sap is stored at −18° C. until further processing is required.

The sap is spray-dried under suitable conditions to obtain a free flowing powder. The moisture content in the powder is preferably less than 5% after spray drying and, if necessary, it is further dried in a vacuum oven or using a fluid bed drier.

Both the sap and the spray-dried material have been shown effective as an appetite suppressant in biological assays in rats.

Experimental 50 kg of *Hoodia gordonii* plants were washed with tap water and thereafter sliced into 1 cm slices. The sliced plants were then pressed through a hydraulic press at 300 bar for a minimum of 0.5 hour per batch. The sap was collected and the mass was found to be 10 kg when *Hoodia gordonii* plants from the environment were used, and 20 kg when *Hoodia gordonii* plants from the cultivation programme was used. The sap (500 g) was spray-dried using the following conditions:

| Flow rate | 2.85 ml/min |
|---|---|
| Inlet temperature | 110° C. |
| Outlet temperature | 70° C. |
| Chamber temperature | 78° C. |

The spray-dried powder obtained was a free flowing powder (22 g) with a moisture content of 6.9%.

The spray dried powder was analysed for active ingredient concentration using HPLC techniques. The concentration of the active was determined to be 13 g/kg of spray dried powder.

HPLC Analysis Method

| Eluant | Acetonitrile: water (7:3), isocratic |
|---|---|
| Column | Reverse phase C-18 |
| UV absorbance | 225 nm |
| Flow rate | 1 ml/min |
| Injection volume | 10 $\mu$l |

Method

Spray-dried powder (10 mg) was dissolved in water (0.5 ml) and acetonitrile (0.5 ml) 10 $\mu$l of this solution was injected into the HPLC and the concentration of the active compound (1) was determined using a standard curve which was prepared from the pure compound (1).

EXAMPLE 44

The results of a study designed to assess the possible anorectic effects of compound (1) in the rat are presented below. In the following, the samples tested are pure sap (Sample 1), spray-dried sap (Sample 2) and active moiety (Sample 3). Samples 1 and 2 are the sap and the spray-dried sap respectively, as described in Example 43 above. Sample 3 is solvent-extracted compound (1) of $\geq$95% purity.

Sample 1 to 3 were each administered as a single oral dose to male Wistar rats. Two additional control groups received vehicle (distilled water or DMSO). Orally administered fenfluramine (7.5 mg/kg) was included as a reference standard.

Sample 1 (pure sap) administered orally, produced dose-dependent reductions in food consumption which were statistically significant at doses of 1600 mg/kg and above when compared with vehicle-treated controls. Concomitant reductions in bodyweight (or growth rate) were also recorded. On the day of dosing, statistically significant increases in water consumption were recorded at 3 hours post-dose (6400 and 10000 mg/kg) and 6 hours post-dose (10000 mg/kg). Between 24 and 48 hours post-dose, statistically significant reductions in water consumption were recorded at doses of 3200 mg/kg and above.

Sample 2 (spray-dried sap) administered orally at 76 mg/kg also produced statistically significant reductions in food consumption and bodyweight when compared with vehicle-treated animals. No statistically significant effects on water consumption were recorded.

Sample 3 (active moiety) produced statistically significant reductions in food consumption at an oral dose of 5.0 mg/kg. No statistically significant effects on bodyweights were produced by the active moiety although examination of the data revealed a slight delay in growth when compared with vehicle-treated control animals. No statistically significant effects on water consumption were recorded.

The reference standard, fenfluramine (7.5 mg/kg), produced statistically significant reductions in food consumption at 6 and 24 hours post-dose when compared with the relevant vehicle-treated control group. No statistically significant effects on water consumption or bodyweight were recorded.

No treatment-related effects on the livers were recorded.

TEST SUBSTANCE

| Identity | Sample 1 (pure sap) | Sample 2 (spray-dried sap) | Sample 3 (active moiety) |
| --- | --- | --- | --- |
| Appearance | Brown liquid | Powder | White powder |
| Storage conditions | $-20°$ C. in the dark | Room temperature in the dark | $4°$ C. in the dark |
| Purity | Pure sap | Pure spray-dried sap | $\geq 95\%$ |
| Vehicle | Distilled water | Distilled water | Dimethyl-sulphoxide (DMSO) |

Experimental Procedure

Fifty-five male Wistar rats were used for the study.

Bodyweights, food consumption (food hopper weight) and water consumption (bottle weight) were recorded daily at the same time each day from the day of arrival until the termination of the study.

On Day 1, the rats received a single oral (gavage) dose according to the following table:

| Group | n | Oral treatment | Dose (mg/kg) |
| --- | --- | --- | --- |
| 1 | 5 | Vehicle (distilled water) | — |
| 2 | 4 | Sample 1 (pure sap) | 800 |
| 3 | 5 | Sample 1 (pure sap) | 1600 |
| 4 | 5 | Sample 1 (pure sap) | 3200 |
| 5 | 5 | Sample 1 (pure sap) | 6400 |
| 6 | 5 | Sample 1 (pure sap) | 10000 |
| 7 | 5 | Sample 2 spray-dried sap | 38 |
| 8 | 5 | Sample 2 spray-dried sap | 76 |
| 9 | 5 | Sample 3 (active moiety) | 2.5 |
| 10 | 5 | Sample 3 (active moiety) | 5.0 |
| 11 | 3 | Fenfluramine | 7.5 |
| 12 | 3 | Vehicle (DMSO) | — |

Groups 1–8 were dosed using a constant dose volume of 10 ml/kg and groups 9–12 were dosed using a dose volume of 1 mg/kg.

Food water consumption were also measured at 1,3 and 6 hours after dosing on Day 1.

Following the measurements of Day 8, the animals were killed by carbon dioxide asphyxiation, and the livers excised and placed in lost buffered formalin, prior to histology. Paraffin wax sections of each liver were taken at 4–5 $\mu$m and stained with haematoxylin and eosin. Additional sections were cut on a cryostat at 12 $\mu$m and stained for fat with Oil Red O (ORO).

Data Analysis

The post-dose food and water consumption measurements and bodyweights at each time-point for the P57-treated animals were compared with those for the relevant, similarly-treated vehicle control group using analysis of variance followed by Williams' test for comparisons with controls.

The data for the fenfluramine-treated animals was compared with that for the vehicle-treated control group using Student's t test.

Results

The results are summarised in the tables.

Sample 1 (pure sap) administered orally produced marked, dose-related reductions in daily food consumption. The duration and amplitude of these reductions in food consumption were dose-dependent. At 24 hours post-dose, Sample 1 (pure sap) produced statistically significant reductions in food consumption at doses of 1600 mg/kg and above when compared with vehicle-treated controls. The highest dose of Sample 1 (sap) (10000 mg/kg) produced statistically significant reductions in food consumption on a daily basis up to 5 days post-dose.

Sample 2 (spray-dried sap) and Sample 3 (active moiety) produced marked and statistically significant reductions in food consumption at oral doses of 76 and 5.0 mg/kg respectively. In both cases the effects lasted 48 hours post-dose.

The reference standard, fenfluramine (7.5 mg/kg, p.o.) produced statistically significant reductions in food consumption at 6 and 24 hours post-dose when compared with the relevant vehicle-treated control group (Group 12).

Sample 2 (spray-dried sap) and Sample 3 (active moiety) produced no marked, dose-related effects on water consumption. On the day of dosing, the pure sap produced statistically significant increases in water consumption at 3 hours post-dose (6400 and 10000 mg/kg) and 6 hours post-dose (10000 mg/kg). Two days after dosing however, statistically significant decreases in water consumption were recorded in animals receiving Sample 1 (sap) at 3200, 6400 and 10000 mg/kg. These reductions however, were not clearly dose-related and only occurred between 1 and 2 days post-dose. The biological significance of these effects therefore remains unclear.

Sample 1 (pure sap) produced dose-related, statistically significant effects on bodyweights when compared with the vehicle-treated control group (Group 1). When administered orally at doses of 3200 mg/kg and above, Sample 1 (pure sap) produced statistically significant reductions in bodyweight or decreased growth rates when compared with vehicle-treated animals. These effects were statistically significant from 48 hours post-dose until the end of the study.

Sample 2 (spray-dried sap) administered orally at 76 mg/kg also produced statistically significant reductions in growth of the animals when compared with the vehicle-treated control group (Group 1). These effects were statistically significant between Days 3 (48 hours post-dose) and 5 inclusive.

Although Sample 3 (active moiety) appeared to delay the growth of the animals at the highest dose (5.0 mg/kg) when compared with the relevant vehicle-treated control group (Group 12), this effect was not statistically significant.

Fenfluramine, (7.5 mg/kg) produced no marked or statistically significant effects on water consumption or bodyweights when compared with the vehicle-treated control group (Group 12).

No treatment-related effects on the livers were recorded.

TABLE 1

Effects of oral administration on food consumption in the rat (daily pre-dose data)

| | | | Group mean food consumption (g ± sd) between Days: | | | | |
|---|---|---|---|---|---|---|---|
| Group | Oral treatment | Dose (mg/kg) | −6—−5 | −5—−4 | −4—−3 | −3—−2 | −2—−1 |
| 1 | Vehicle (water) | — | 27.8 ± 1.54 | 24.2 ± 1.83 | 27.6 ± 3.67 | 28.3 ± 3.50 | 29.4 ± 2.66 |
| 2 | Sample 1 sap | 800 | 28.3 ± 1.43 | 24.9 ± 0.82 | 27.7 ± 0.76 | 28.4 ± 1.51 | 30.1 ± 0.27 |
| 3 | Sample 1 sap | 1600 | 29.0 ± 1.39 | 25.0 ± 2.16 | 27.4 ± 1.96 | 28.8 ± 0.61 | 29.5 ± 1.55 |
| 4 | Sample 1 sap | 3200 | 27.2 ± 2.33 | 25.1 ± 2.46 | 26.0 ± 2.52 | 28.5 ± 2.29 | 27.6 ± 1.15 |
| 5 | Sample 1 sap | 6400 | 28.7 ± 1.64 | 25.3 ± 1.73 | 27.3 ± 1.45 | 29.2 ± 1.09 | 30.3 ± 0.90 |
| 6 | Sample 1 sap | 10000 | 28.5 ± 2.38 | 23.7 ± 2.73 | 26.0 ± 2.31 | 27.0 ± 3.50 | 28.7 ± 2.26 |
| 7 | Sample 2 spray-dried | 38 | 28.1 ± 1.24 | 23.9 ± 1.79 | 24.5 ± 2.30 | 27.6 ± 1.61 | 28.5 ± 1.87 |
| 8 | Sample 2 spray-dried | 76 | 28.7 ± 0.91 | 26.5 ± 1.55 | 27.1 ± 1.01 | 28.7 ± 1.99 | 28.9 ± 1.37 |
| 9 | Sample 3 active moiety | 2.5 | 28.8 ± 1.49 | 26.4 ± 3.12 | 29.0 ± 1.99 | 29.4 ± 1.76 | 29.5 ± 2.81 |
| 10 | Sample 3 active moiety | 5.0 | 28.3 ± 2.1 | 25.8 ± 1.86 | 28.1 ± 2.65 | 28.0 ± 2.65 | 28.5 ± 3.03 |
| 11 | Fenfluramine | 7.5 | 29.1 ± 0.66 | 25.3 ± 4.03 | 27.0 ± 1.53 | 30.8 ± 0.54 | 29.7 ± 2.84 |
| 12 | Vehicle (DMSO) | — | 27.9 ± 1.8 | 26.7 ± 2.11 | 28.7 ± 1.99 | 28.1 ± 4.06 | 30.5 ± 2.54 |

Effects of oral administration on food consumption in the rat (daily post-dose data)

| | | Dose | Group mean food consumption (g ± sd) between Days: | | | | | | |
|---|---|---|---|---|---|---|---|---|---|
| Group | Oral treatment | (mg/kg) | 1–2 | 2–3 | 3–4 | 4–5 | 5–6 | 6–7 | 7–8 |
| 1 | Vehicle (water) | — | 29.5 ± 3.15 | 29.6 ± 2.84 | 30.6 ± 3.49 | 31.8 ± 3.49 | 30.7 ± 2.24 | 31.7 ± 3.03 | 32.8 ± 3.18 |
| 2 | Sample 1 sap | 800 | 26.1 ± 0.98 | 29.3 ± 1.49 | 30.7 ± 1.15 | 30.9 ± 0.60 | 33.3 ± 1.69 | 32.7 ± 0.80 | 40.1 ± 13.40 |
| 3 | Sample 1 sap | 1600 | 22.6** ± 3.17 | 26.9 ± 2.06 | 30.9 ± 2.54 | 30.9 ± 1.22 | 34.1 ± 1.36 | 33.7 ± 1.69 | 33.8 ± 1.61 |
| 4 | Sample 1 sap | 3200 | 20.1** ± 1.39 | 19.0** ± 1.88 | 22.8** ± 1.77 | 28.0 ± 3.14 | 31.4 ± 2.82 | 32.3 ± 2.91 | 33.0 ± 3.01 |
| 5 | Sample 1 sap | 6400 | 18.2** ± 4.18 | 14.8** ± 1.75 | 18.4** ± 0.97 | 22.4** ± 3.01 | 26.9 ± 2.81 | 31.0 ± 2.31 | 32.0 ± 2.34 |
| 6 | Sample 1 sap | 10000 | 15.1** ± 2.98 | 12.4** ± 2.61 | 16.0** ± 3.15 | 19.7** ± 4.31 | 22.6* ± 5.70 | 30.1 ± 4.79 | 32.6 ± 5.90 |
| 7 | Sample 2 spray-dried | 38 | 25.6 ± 2.85 | 27.3 ± 0.95 | 30.3 ± 2.06 | 31.0 ± 2.13 | 31.8 ± 1.63 | 31.1 ± 1.94 | 31.8 ± 2.45 |
| 8 | Sample 2 spray-dried | 76 | 24.2* ± 3.25 | 25.2* ± 3.24 | 29.9 ± 1.85 | 30.2 ± 2.28 | 31.2 ± 2.26 | 32.3 ± 1.44 | 33.1 ± 0.61 |
| 9 | Sample 3 active moiety | 2.5 | 26.8 ± 3.33 | 29.1 ± 3.43 | 31.7 ± 3.08 | 34.0 ± 2.95 | 34.4 ± 4.32 | 33.1 ± 4.11 | 34.8 ± 3.71 |
| 10 | Sample 3 active moiety | 5.0 | 22.1†† ± 2.19 | 21.0 †† ± 3.07 | 27.6 ± 5.26 | 30.5 ± 3.33 | 33.00 ± 3.16 | 32.4 ± 3.25 | 33.0 ± 3.84 |
| 11 | Fenfluramine | 7.5 | 22.4† ± 3.19 | 31.9 ± 0.84 | 32.7 ± 2.50 | 33.0 ± 2.55 | 30.4 ± 0.23 | 32.7 ± 1.90 | 32.4 ± 1.60 |
| 12 | Vehicle (DMSO) | — | 29.9 ± 3.36 | 30.6 ± 4.43 | 30.1 ± 4.17 | 32.4 ± 5.26 | 31.8 ± 3.08 | 32.8 ± 3.98 | 33.3 ± 3.76 | sd Standard deviation
Groups 2–8 were compared with vehicle Group 1: *p < 0.05, **p < 0.01
Groups 9–11 were compared with vehicle Group 12: †p < 0.05, ††p < 0.01

TABLE 2a

Effects of oral administration on water consumption in the rat (daily pre-dose data)

| | | | Group mean water consumption (g ± sd) between Days: | | | | |
|---|---|---|---|---|---|---|---|
| Group | Oral treatment | Dose (mg/kg) | −6—−5 | −5—−4 | −4—−3 | −3—−2 | −2—−1 |
| 1 | Vehicle (water) | — | 40.9 ± 4.61 | 34.8 ± 4.15 | 37.6 ± 5.63 | 33.5 ± 7.42 | 32.2 ± 6.32 |
| 2 | Sample 1 sap | 800 | 36.6 ± 1.96 | 37.1 ± 9.74 | 36.4 ± 4.81 | 28.1 ± 1.83 | 30.4 ± 4.75 |
| 3 | Sample 1 sap | 1600 | 43.4 ± 10.53 | 35.9 ± 3.84 | 38.4 ± 4.56 | 31.1 ± 4.47 | 36.5 ± 5.39 |
| 4 | Sample 1 sap | 3200 | 40.1 ± 5.58 | 33.3 ± 3.01 | 37.3 ± 4.46 | 31.3 ± 3.48 | 31.7 ± 3.18 |
| 5 | Sample 1 sep | 6400 | 43.8 ± 8.57 | 36.3 ± 9.02 | 35.4 ± 8.18 | 34.0 ± 6.62 | 35.1 ± 5.72 |
| 6 | Sample 1 sap | 10000 | 37.4 ± 5.34 | 32.7 ± 3.35 | 33.2 ± 4.86 | 29.0 ± 5.11 | 32.2 ± 3.27 |
| 7 | Sample 2 spray-dried | 38 | 40.0 ± 4.35 | 35.8 ± 4.92 | 34.7 ± 3.20 | 30.2 ± 1.88 | 31.4 ± 2.98 |
| 6 | Sample 2 spray-dried | 76 | 38.6 ± 1.98 | 37.0 ± 1.95 | 48.8 ± 21.5 | 31.6 ± 4.56 | 39.0 ± 17.27 |
| 9 | Sample 3 active moiety | 2.5 | 42.0 ± 6.70 | 37.0 ± 5.05 | 34.1 ± 3.16 | 28.0 ± 2.58 | 31.6 ± 3.12 |
| 10 | Sample 3 activo moiety | 5.0 | 40.9 ± 4.48 | 34.2 ± 3.00 | 32.7 ± 1.26 | 28.2 ± 1.65 | 33.1 ± 14.82 |
| 11 | Fonfluramine | 7.5 | 47.0 ± 5.3 | 35.5 ± 7.49 | 34.7 ± 3.73 | 30.9 ± 2.12 | 31.6 ± 2.80 |
| 12 | Vehicle (DMSO) | — | 43.3 ± 6.67 | 34.5 ± 4.97 | 35.2 ± 4.34 | 28.3 ± 4.64 | 31.4 ± 6.44 |

Effects of oral administration on water consumption in the rat (daily post-dose data)

| | | Dose | Group mean water consumption (g ± sd) between Days: | | | | | | |
|---|---|---|---|---|---|---|---|---|---|
| Group | Oral treatment | (mg/kg) | 1–2 | 2–3 | 3–4 | 4–5 | 5–6 | 6–7 | 7–8 |
| 1 | Vehicle (water) | — | 34.9 ± 5.45 | 36.9 ± 6.06 | 38.0 ± 7.59 | 37.2 ± 6.16 | 37.7 ± 5.54 | 35.3 ± 2.86 | 36.5 ± 5.85 |
| 2 | Sample 1 sap | 800 | 30.9 ± 3.77 | 34.4 ± 8.12 | 38.2 ± 13.71 | 35.9 ± 13.51 | 39.5 ± 11.20 | 28.8 ± 1.22 | 31.8 ± 5.58 |
| 3 | Sample 1 sap | 1600 | 29.2 ± 1.66 | 31.7 ± 5.35 | 41.3 ± 11.21 | 34.8 ± 4.10 | 48.1 ± 12.27 | 37.8 ± 7.28 | 36.9 ± 9.28 |
| 4 | Sample 1 sap | 3200 | 35.9 ± 5.68 | 26.2* ± 2.66 | 30.5 ± 2.44 | 34.1 ± 4.80 | 45.8 ± 16.54 | 51.0 ± 35.21 | 42.6 ± 13.88 |

TABLE 2a-continued

| | | | | | | | | | |
|---|---|---|---|---|---|---|---|---|---|
| 5 | Sample 1 sap | 6400 | 33.4 ± 12.04 | 27.4* ± 8.13 | 32.6 ± 10.67 | 35.4 ± 10.78 | 45.2 ± 8.72 | 36.2 ± 6.72 | 35.9 ± 9.58 |
| 6 | Sample 1 sap | 10000 | 31.7 ± 12.74 | 28.5* ± 8.65 | 32.4 ± 8.87 | 36.6 ± 6.50 | 40.7 ± 11.51 | 38.0 ± 8.66 | 37.5 ± 6.21 |
| 7 | Sample 2 spray-dried | 38 | 36.0 ± 6.02 | 34.5 ± 1.79 | 36.2 ± 7.16 | 39.6 ± 7.09 | 42.7 ± 9.74 | 45.6 ± 17.15 | 46.1 ± 9.49 |
| 8 | Sample 2 spray-dried | 76 | 45.0 ± 19.03 | 39.1 ± 16.59 | 46.9 ± 18.34 | 35.9 ± 3.40 | 41.9 ± 12.37 | 36.9 ± 6.47 | 38.1 ± 6.93 |
| 9 | Sample 3 active moiety | 2.5 | 32.2 ± 4.01 | 36.1 ± 12.42 | 38.3 ± 11.71 | 41.5 ± 16.60 | 34.7 ± 7.57 | 33.0 ± 4.20 | 35.3 ± 8.70 |
| 10 | Sample 3 active moiety | 5.0 | 33.9 ± 2.40 | 31.5 ± 8.12 | 35.1 ± 3.82 | 37.7 ± 5.99 | 39.5 ± 7.78 | 37.4 ± 11.07 | 37.8 ± 6.42 |
| 11 | Fenfluramine | 7.5 | 34.1 ± 3.60 | 37.2 ± 1.48 | 36.7 ± 3.92 | 33.6 ± 2.89 | 33.7 ± 5.43 | 32.1 ± 1.93 | 33.6 ± 2.50 |
| 12 | Vehicle (DMSO) | — | 40.7 ± 9.10 | 33.8 ± 9.37 | 32.8 ± 7.07 | 35.8 ± 11.49 | 33.8 ± 9.62 | 32.3 ± 7.44 | 32.0 ± 7.22 | sd Standard deviation
Groups 2–8 were compared with vehicle Group 1: *p < 0.05
Groups 9–11 were compared with vehicle Group 12 (no significances)

TABLE 3

Effects of oral administration on bodyweight in the rat (daily pre-dose data)

| | | | Group mean bodyweight (g ± sd) on Day: | | | | |
|---|---|---|---|---|---|---|---|
| Group | Oral treatment | Dose (mg/kg) | −5 | −4 | −3 | −2 | −1 |
| 1 | Vehicle (water) | — | 130.9 ± 5.56 | 150.7 ± 5.37 | 157.3 ± 5.29 | 168.1 ± 6.20 | 177.5 ± 6.70 |
| 2 | Sample 1 sap | 800 | 131.6 ± 4.34 | 150.1 ± 4.84 | 158.5 ± 4.35 | 169.6 ± 4.99 | 177.7 ± 4.10 |
| 3 | Sample 1 sap | 1600 | 130.1 ± 4.3 | 148.6 ± 6.59 | 156.7 ± 6.38 | 167.5 ± 6.04 | 176.6 ± 6.37 |
| 4 | Sample 1 sap | 3200 | 130.8 ± 6.19 | 147.7 ± 7.56 | 154.4 ± 8.06 | 165.2 ± 8.43 | 175.8 ± 9.10 |
| 5 | Sample 1 sap | 6400 | 132.6 ± 7.01 | 151.3 ± 7.23 | 158.4 ± 8.50 | 169.0 ± 8.79 | 178.1 ± 7.75 |
| 6 | Sample 1 sap | 10000 | 132.3 ± 6.75 | 151.8 ± 9.08 | 157.3 ± 9.37 | 167.1 ± 10.41 | 175.4 ± 10.90 |
| 7 | Sample 2 spray-dried | 38 | 131.7 ± 8.28 | 149.0 ± 5.85 | 156.2 ± 5.81 | 166.7 ± 5.54 | 175.6 ± 8.42 |
| 8 | Sample 2 spray-dried | 76 | 130.0 ± 6.99 | 146.1 ± 6.00 | 155.9 ± 6.59 | 166.0 ± 6.87 | 175.1 ± 6.55 |
| 9 | Sample 3 active moiety | 2.5 | 132.6 ± 7.63 | 158.9 ± 8.51 | 157.3 ± 8.91 | 169.8 ± 8.96 | 179.4 ± 8.71 |
| 10 | Sample 3 active moiety | 5.0 | 133.5 ± 6.45 | 150.5 ± 9.55 | 158.8 ± 8.48 | 171.0 ± 7.72 | 179.0 ± 9.20 |
| 11 | Fenfluramine | 7.5 | 133.2 ± 9.21 | 152.7 ± 9.09 | 160.0 ± 9.82 | 170.0 ± 9.15 | 182.8 ± 10.21 |
| 12 | Vehicle (DMSO) | — | 129.1 ± 3.17 | 147.3 ± 4.37 | 155.0 ± 6.29 | 166.0 ± 5.91 | 174.8 ± 8.26 |

Effects of oral administration on bodyweight in the rat (daily post-dse data)

| Group | Oral treatment | Dose (mg/kg) | Pre-dose (1) | 2 | 3 | 4 | 5 | 6 | 7 | 8 |
|---|---|---|---|---|---|---|---|---|---|---|
| 1 | Vehicle (water) | — | 185.4 ± 7.77 | 192.6 ± 7.16 | 202.0 ± 10.17 | 211.2 ± 7.98 | 220.2 ± 10.35 | 227.2 ± 10.26 | 235.6 ± 11.62 | 242.8 ± 11.97 |
| 2 | Sample 1 sap | 800 | 186.0 ± 4.90 | 187.8 ± 4.55 | 198.5 ± 4.20 | 206.8 ± 5.91 | 214.6 ± 4.65 | 222.6 ± 4.99 | 231.5 ± 3.70 | 240.0 ± 3.65 |
| 3 | Sample 1 sap | 1600 | 185.0 ± 6.67 | 181.0 ± 8.28 | 193.2 ± 6.42 | 204.0 ± 5.61 | 212.4 ± 6.40 | 223.0 ± 6.33 | 232.6 ± 7.70 | 240.4 ± 6.86 |
| 4 | Sample 1 sap | 3200 | 181.8 ± 11.18 | 184.6 ± 8.88 | 186.2* ± 6.67 | 189.8** ± 9.99 | 199.2 ± 9.34 | 210.6** ± 10.21 | 219.0* ± 11.29 | 226.4* ± 12.18 |
| 5 | Sample 1 sap | 6400 | 166.6 ± 7.96 | 185.6 ± 6.39 | 183.8** ± 6.67 | 185.2** ± 9.16 | 191.2** ± 7.69 | 201.0 ± 6.69 | 213.0** ± 6.98 | 222.0** ± 7.94 |
| 6 | Sample 1 sap | 10000 | 182.8 ± 12.22 | 181.4 ± 14.06 | 179.8** ± 15.85 | 180.6* ± 13.85 | 185.6** ± 11.28 | 192.2** ± 10.99 | 203.4 ± 11.68 | 212.4** ± 11.35 |
| 7 | Sample 2 spray-dried | 38 | 183.4 ± 11.11 | 185.8 ± 9.23 | 195.8 ± 7.79 | 205.6 ± 9.79 | 214.4 ± 9.61 | 222.6 ± 9.34 | 231.4 ± 10.62 | 239.6 ± 11.46 |
| 8 | Sample 2 spray-dried | 76 | 160.6 ± 6.47 | 163.4 ± 7.57 | 188.6* ± 6.73 | 196.2* ± 8.50 | 206.0* ± 9.43 | 214.0 ± 9.51 | 222.0 ± 9.49 | 232.2 ± 9.66 |
| 9 | Sample 3 active moiety | 2.5 | 166.2 ± 9.42 | 191.2 ± 11.15 | 200.0 ± 11.25 | 209.6 ± 12.28 | 219.6 ± 12.95 | 229.4 ± 13.69 | 236.4 ± 14.50 | 247.0 ± 14.35 |
| 10 | Sample 3 active moiety | 5.0 | 186.4 ± 10.02 | 192.0 ± 9.93 | 192.4 ± 9.64 | 201.0 ± 11.27 | 209.4 ± 12.70 | 219.8 ± 11.66 | 226.2 ± 12.26 | 236.0 ± 13.65 |
| 11 | Fenfluramine | 7.5 | 190.3 ± 9.71 | 190.3 ± 10.97 | 197.7 ± 7.37 | 207.7 ± 7.23 | 217.7 ± 10.69 | 224.3 ± 10.12 | 234.3 ± 12.70 | 243.3 ± 9.24 |
| 12 | Vehicle (DMSO) | — | 183.3 ± 8.33 | 190.3 ± 10.26 | 199.0 ± 10.82 | 207.7 ± 12.66 | 215.7 ± 14.05 | 222.3 ± 11.64 | 230.7 ± 15.95 | 239.0 ± 17.35 | sd Standard deviation
Groups 2–8 were compared with vehicle Group 1: *p 21 0.05, **p < 0.01
Groups 9–11 were compared with vehicle Group 12 (no significances)

Histopathology Report

Histological examination was restricted to the liver. No treatment-related changes were detected for Sample 1 (liquid), Sample 2 (spray-dried sap), Sample 3 (active moiety), fenfluramine or the DMSO control group.

The findings recorded were of a similar incidence in control and treated groups.

TABLE

Microscopic pathology incidence summary

|  | Group 1 | Group 2 | Group 3 | Group 4 | Group 5 | Group 6 |
|---|---|---|---|---|---|---|
| Sex: Males | 0 mg/kg | 800 mg/kg | 1600 mg/kg | 3200 mg/kg | 6400 kg/mg | 10000 mg/kg |
| Males on study | 5 | 4 | 5 | 5 | 5 | 5 |
| Animals completed | 5 | 4 | 5 | 5 | 5 | 5 |
| Liver |  |  |  |  |  | 5 |
| Examined | 5 | 4 | 5 | 5 | 5 | 0 |
| No abnormalities detected | 0 | 0 | 1 | 2 | 3 | 3 |
| Parenchymal inflammatory cell foci (Total) | 0 | 1 | 0 | 0 | 0 | 3 |
| Minimal | 0 | 1 | 0 | 0 | 0 | 1 |
| Hepatocyte hypertrophy - centrilobular (Total) | 0 | 0 | 0 | 0 | 0 | 1 |
| Minimal | 0 | 0 | 0 | 0 | 0 | 0 |
| Extramedullary haemopoiesis (Total) | 2 | 0 | 0 | 0 | 0 | 0 |
| Minimal | 2 | 0 | 0 | 0 | 0 | 0 |
| Hepatocyte necrosis - focal (Total) | 1 | 0 | 0 | 0 | 0 | 0 |
| Minimal | 1 | 0 | 0 | 0 | 0 | 0 |
| Portal lymphoid infiltration (Total) | 3 | 4 | 4 | 3 | 2 | 2 |
| Minimal | 3 | 4 | 4 | 3 | 2 | 2 |
| Eosinophilic hepatocytes - focal (Total) | 1 | 0 | 0 | 0 | 0 | 0 |
| Minimal | 1 | 0 | 0 | 0 | 0 | 0 |
| Portal fibrosis (Total) | 0 | 0 | 1 | 0 | 0 | 0 |
| Minimal | 0 | 0 | 1 | 0 | 0 | 0 |
| Liver (ORO stain) |  |  |  |  |  |  |
| Examined | 5 | 4 | 5 | 5 | 5 | 5 |
| No abnormalities detected | 2 | 3 | 2 | 4 | 3 | 3 |
| Hepatocyte fat - centrilobular (Total) | 3 | 1 | 2 | 1 | 2 | 2 |
| Minimal | 3 | 1 | 2 | 1 | 2 | 2 |
| Hepatocyte fat - periportal (Total) | 0 | 0 | 1 | 0 | 0 | 0 |
| Minimal | 0 | 0 | 1 | 0 | 0 | 0 |
|  | Group 7 | Group 8 | Group 9 | Group 10 | Group 11 | Group 12 |
| Sex: Males | 38 mg/kg | 76 mg/kg | 2.5 mg/kg | 5 mg/kg | 7.5 mg/kg | 0 mg/kg |
| Males on study | 5 | 5 | 5 | 5 | 3 | 3 |
| Animals completed | 5 | 5 | 5 | 5 | 3 | 3 |
| Liver |  |  |  |  |  |  |
| Examined | 5 | 5 | 5 | 5 | 3 | 3 |
| No abnormalities detected | 2 | 2 | 0 | 1 | 0 | 2 |
| Parenchymal inflammatory cell foci (Total) | 0 | 0 | 0 | 0 | 0 | 1 |
| Minimal | 0 | 0 | 0 | 0 | 0 | 1 |
| Hepatocyte necrosis - focal (Total) | 0 | 0 | 1 | 0 | 0 | 0 |
| Minimal | 0 | 0 | 1 | 0 | 0 | 0 |
| Portal lymphoid infiltration (Total) | 3 | 3 | 5 | 4 | 3 | 1 |
| Minimal | 3 | 3 | 5 | 4 | 3 | 1 |
| Portal leucocytes (Total) | 0 | 0 | 1 | 0 | 0 | 0 |
| Minimal | 0 | 0 | 1 | 0 | 0 | 0 |
| Liver (ORO stain) |  |  |  |  |  |  |
| Examined | 5 | 5 | 5 | 5 | 3 | 3 |
| No abnormalities detected | 5 | 3 | 3 | 3 | 2 | 2 |
| Hepatocyte fat - centrilobular (Total) | 0 | 2 | 2 | 2 | 1 | 1 |
| Minimal | 0 | 2 | 2 | 2 | 1 | 0 |

EXAMPLE 45

A further bioassay, which employed the same test samples as described in Example 44, is described below. Animals in this study received a restricted diet i.e. animals only received food between 12:00 and 3:00 pm daily. This is different from all other biological assays conducted thus far, whereby food was available to the rats at lib. Animals were acclimatised over a seven day period (days −7 to −1), dosing took place from day 0 to day 6 at 9:00 am by oral gavage. The recovery period was from days 7 to day 13. Dosage groups are described in Table 1 below. It should be noted that the actual control group is labelled Group 09. Group 5 is a controlled group which received a diet equivalent to that of Group 4. The purpose of this group was to evaluate the effect a restricted diet has on the lives of the animals.

Results

The results generated during the study showed that the acclimatization period was too short. Rats feed mainly during the night and the sudden change to a restricted access to feed for 3 hours during day-time, resulted in low daily intakes. The daily intake of feed was still increasing in most groups at the end of the acclimatization period when dosing with the test items started. As a result of this, the effect of the test materials did not significantly affect the food intake of the rats during the period of dosing.

Figure 5:
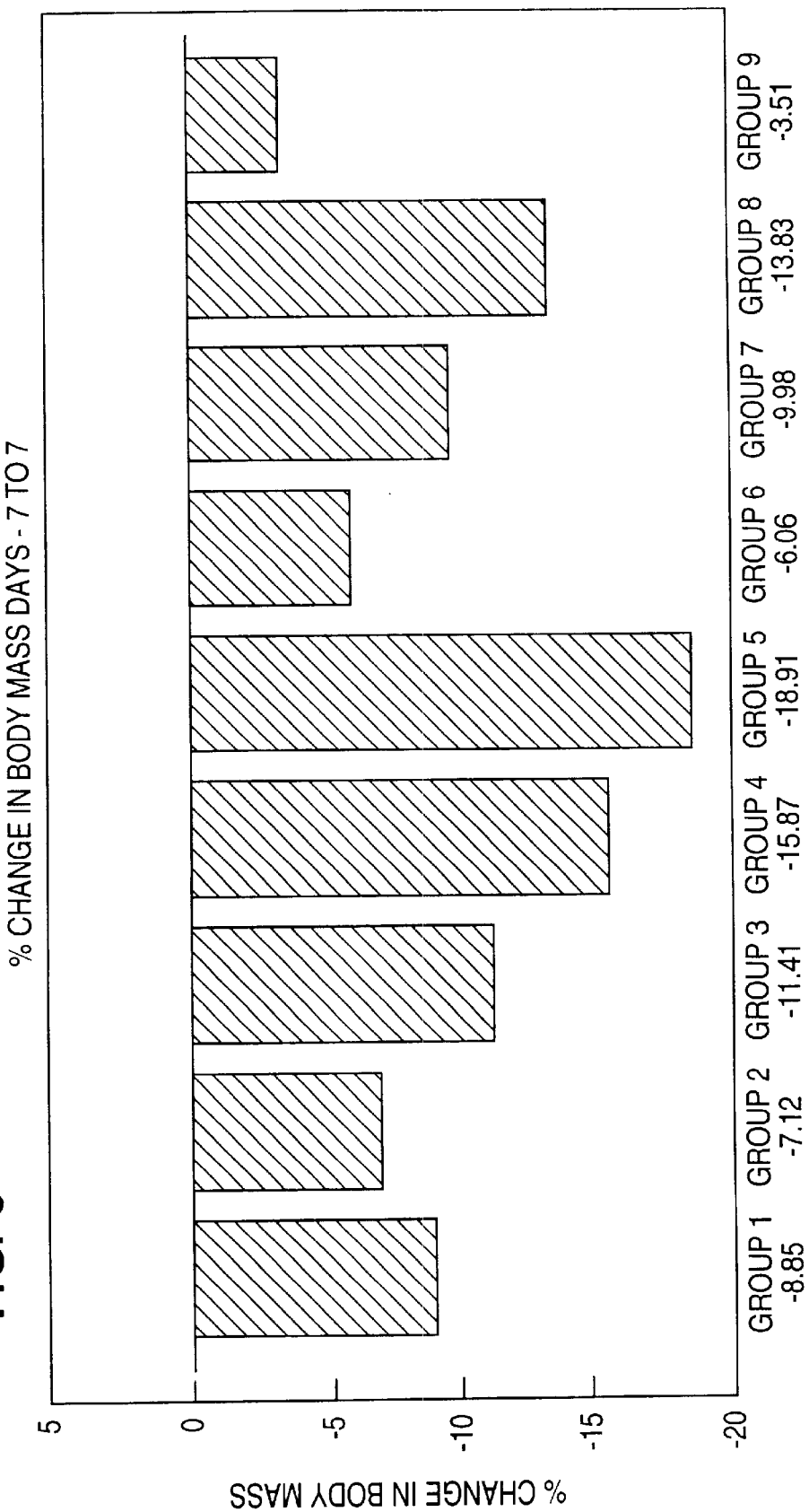

The mean body masses for the different groups for day −7 to −1 and days 0 to 6 are shown in the Table D1 and Table D2. The effect of the different dosages of the sap and spray-dried sap is shown in the accompanying graphs as a change in body mass day 0 to 7 (FIG. 5), and % change in body mass day −7 to 7 (FIG. 6). The loss in body mass is clearly dose-related especially with the higher dosages.

The histopathological examination of the livers did not show any significant pathology in the groups receiving the cast items.

Food

Food consumption was measured daily, during acclimatization and during the study. Food was available for a 3 hour feeding period daily, starting at 12:00 and ending at 15:00. The animals were fasted for the remainder of the time. Animals in Group 5 received a measured quantity food on Day 1, equivalent to the average food consumption of Group 4 on Day 0. This controlled feeding pattern for Group 5, as determined from the average food consumption of Group 4 from the previous day, was followed for Days 1–7.

Water

Water was provided in standard containers. Water (Magalies Water Board Tap Water, suitable for human consumption) was available ad libitum. Water consumption was measured once daily, at the same time each day, after food consumption determination.

Acclimatization

The animals were acclimatized for seven days before the start of the stud y, during which time food and water consumption were determined as described above. The body masses were determined on a daily basis during this time.

Study Design and Procedures

TABLE 1

STUDY DESIGN

| GROUP | TEST | NUMBERS | DOSE | TEST ITEM |
|---|---|---|---|---|
| 01 | 6♂ | 001–006 | 100 mg/kg | Frozen sap |
| 02 | 6♂ | 007–012 | 400 mg/kg | Frozen sap |
| 03 | 6♂ | 013–018 | 1600 mg/kg | Frozen sap |
| 04 | 6♂ | 019–024 | 3200 mg/kg | Frozen sap |
| 05 | 6♂ | 025–030 | CONTROL | Elga Option 4 Purified Water |
| 06 | 6♂ | 031–036 | 2.2 mg/kg | Spray-dried sap |
| 07 | 6♂ | 037–042 | 8.8 mg/kg | Spray-dried sap |
| 08 | 6♂ | 043–048 | 35 mg/kg | Spray-dried sap |
| 09 | 6♂ | 049–054 | CONTROL | Elga Option 4 Purified Water |

Route of Administration

The test items were administered on a daily basis for seven days, using an intra-gastric needle. Animals were fasted for 8 hours prior to the item administration (starting at 09:00).

Duration of Treatment

Animals were treated for seven consecutive days (from Day 0–Day 6). Three animals of each group were sacrificed 24 hours after the last dosing (Day 7). The remaining three animals were sacrificed 7 days after the last treatment (Day 13). This procedure was followed for all the groups except for Group 5 where three animals were sacrificed 24 hours after the last controlled feeding (Day 8), the remaining three animals were sacrificed 7 days after the last reatment (Day 13).

Body Masses

Body masses were determined daily, at approximately the same time each day for the duration of the study, including during the acclimatization period.

Euthanasia

Three animals of each group were sacrificed 24 hours after the last dosing (Day 7).

The remaining three animals were sacrificed 7 days after the last treatment. This procedure was followed for all the groups except for Group 5 where three animals were sacrificed 24 hours after the last controlled feeding (Day 8), the remaining three animals were sacrificed 7 Days after the last treatment (Day 13). The animals were euthanased at the end of the study period with $CO_2$ gas.

Ophthalmoscopic Examinations

Ophthalmoscopic examinations, using an ophthalmoscope, were done prior to the first adminstration of the test item and at termination, in all animals in all groups.

Macroscopic Pathology

A full post mortem examination was performed on every animal which was euthanased at the end of the study period.

Histopathology

Histopathological examination was performed on the liver of each of the animals.

TA8LE D

MEAN BODY MASSES/GROUP 1 WEEK

| Group | Oral treatment | Dose (mg/kg) | Mean body masses (g) & Standard deviation | | | | | | |
|---|---|---|---|---|---|---|---|---|---|
| | | | Day −7 | Day −6 | Day −5 | Day −4 | Day −3 | Day −2 | Day −1 |
| 01 | Sample 1 (Sap) | 100 | 203.38 ± 95.39 | 197.13 ± 90.63 | 192.75 ± 89.49 | 188.62 ± 86.75 | 164.95 ± 84.80 | 182.48 ± 83.47 | 182.25 ± 82.57 |
| 02 | Sample 1 (Sap) | 400 | 192.53 ± 65.60 | 183.92 ± 61.20 | 178.25 ± 59.37 | 173.17 ± 58.10 | 170.82 ± 57.42 | 168.25 ± 58.40 | 169.37 ± 59.25 |
| 03 | Sample 1 (Sap) | 1600 | 149.25 ± 54.80 | 142.87 ± 51.89 | 136.85 ± 52.17 | 132.37 ± 49.64 | 131.50 ± 49.50 | 129.67 ± 48.89 | 131.12 ± 48.22 |
| 04 | Sample 1 (Sap) | 3200 | 224.15 ± 80.70 | 214.45 ± 77.25 | 207.10 ± 76.38 | 201.82 ± 75.42 | 198.25 ± 74.82 | 194.83 ± 75.34 | 196.77 ± 74.56 |
| 05 | Elga Option 4 purified water (control) | — | 214.55 ± 74.90 | 204.65 ± 72.41 | 198.57 ± 71.79 | 193.48 ± 68.49 | 192.40 ± 67.48 | 190.67 ± 67.39 | 190.15 ± 65.24 |
| 06 | Sample 2 (Spray-dried sap) | 2.2 | 206.65 ± 65.74 | 199.37 ± 62.49 | 193.18 ± 61.18 | 188.25 ± 60.89 | 186.22 ± 59.98 | 184.55 ± 58.86 | 185.97 ± 56.78 |
| 07 | Sample 2 (Spray-dried sap) | 8.8 | 256.95 ± 77.55 | 246.02 ± 73.67 | 237.47 ± 73.53 | 232.62 ± 71.73 | 229.78 ± 71.76 | 228.07 ± 69.88 | 228.45 ± 68.81 |
| 08 | Sample 2 (Spray-dried sap) | 35 | 194.37 ± 43.74 | 185.83 ± 42.70 | 777.53 ± 41.10 | 172.05 ± 40.13 | 170.10 ± 39.49 | 167.25 ± 37.61 | 168.00 ± 38.83 |
| 09 | Elga Option 4 purified water (control) | — | 171.52 ± 69.81 | 162.67 ± 62.68 | 154.95 ± 61.83 | 151.38 ± 59.46 | 149.63 ± 57.66 | 148.30 ± 57.12 | 149.07 ± 56.01 |

TABLE D-continued

MEAN BODY MASSES/GROUP 1 WEEK

| Group | Oral treatment | Dose (mg/kg) | Mean body masses (g) & Standard deviation | | | | | | |
|---|---|---|---|---|---|---|---|---|---|
| | | | Day 0 | Day 1 | Day 2 | Day 3 | Day 4 | Day 5 | Day 6 |
| 01 | Sample 1 (Sap) | 100 | 183.87 ± 83.33 | 175.83 ± 81.82 | 175.72 ± 79.05 | 175.48 ± 77.54 | 175.53 ± 76.20 | 177.95 ± 73.99 | 178.43 ± 72.68 |
| 02 | Sample 1 (Sap) | 400 | 173.45 ± 60.73 | 164.58 ± 58.52 | 164.75 ± 58.37 | 166.22 ± 57.69 | 166.55 ± 57.79 | 169.93 ± 57.47 | 171.77 ± 57.29 |
| 03 | Sample (Sap) | 1600 | 134.38 ± 46.01 | 129.20 ± 44.74 | 127.53 ± 43.20 | 127.20 ± 41.36 | 126.70 ± 39.19 | 128.00 ± 39.22 | 128.07 ± 38.66 |
| 04 | Sample (Sap) | 3200 | 199.60 ± 75.16 | 196.38 ± 73.96 | 192.20 ± 71.20 | 189.05 ± 69.11 | 186.57 ± 66.29 | 186.05 ± 67.45 | 185.68 ± 65.73 |
| 05 | Elga Option 4 purified water (control) | — | 194.27 ± 67.46 | 187.93 ± 65.48 | 181.97 ± 65.01 | 177.53 ± 64.73 | 174.73 ± 61.08 | 172.85 ± 58.63 | 171.45 ± 56.79 |
| 06 | Sample 2 (Spray-dried sap) | 2.2 | 189.07 ± 60.15 | 181.52 ± 58.99 | 181.48 ± 57.79 | 184.42 ± 55.64 | 185.75 ± 55.29 | 189.35 ± 54.66 | 189.68 ± 53.70 |
| 07 | Sample 2 (Spray-dried sap) | 8.8 | 230.28 ± 89.32 | 221.55 ± 68.02 | 220.17 ± 66.63 | 221.80 ± 63.88 | 222.82 ± 63.56 | 224.82 ± 62.38 | 224.90 ± 62.05 |
| 08 | Sample 2 (Spray-dried sap) | 35 | 169.10 ± 38.40 | 164.42 ± 38.03 | 162.50 ± 36.81 | 162.75 ± 36.36 | 162.52 ± 36.93 | 164.30 ± 37.69 | 164.22 ± 37.18 |
| 09 | Elga Option 4 purified water (control) | — | 151.02 ± 55.45 | 146.55 ± 53.77 | 148.10 ± 52.67 | 149.70 ± 52.05 | 152.58 ± 50.37 | 155.82 ± 49.91 | 157.85 ± 49.70 |

| Group | Oral treatment | Dose (mg/kg) | Mean body masses (g) & Standard deviation | | | | | | |
|---|---|---|---|---|---|---|---|---|---|
| | | | Day 7 | Day 8 | Day 9 | Day 10 | Day 11 | Day 12 | Day 13 |
| 01 | Sample 1 (Sap) (GHA I 35A) | 100 | 185.38 ± 72.64 | 234.73 ± 62.44 | 236.73 ± 62.39 | 234.07 ± 62.09 | 236.33 ± 62.31 | 239.07 ± 60.24 | 238.43 ± 59.85 |
| 02 | Sample 1 (Sap) (GHA I 35A) | 400 | 178.63 ± 58.24 | 225.63 ± 13.05 | 277.13 ± 14.18 | 227.10 ± 14.03 | 229.43 ± 16.97 | 234.93 ± 18.35 | 236.20 ± 15.97 |
| 03 | Sample 1 (Sap) (GHA I 35A) | 1600 | 132.22 ± 37.08 | 133.60 ± 55.17 | 135.23 ± 455.74 | 134.53 ± 54.96 | 138.30 ± 53.03 | 139.30 ± 51.10 | 142.60 ± 49.51 |
| 04 | Sample 1 (Sap) (GHA 9 35A) | 3200 | 188.57 ± 66.14 | 199.63 ± 61.07 | 196.90 ± 57.48 | 196.70 ± 54.55 | 194.73 ± 52.78 | 194.93 ± 50.78 | 197.93 ± 51.57 |
| 05 | Elga Option 4 purified water (control) | — | 173.97 ± 54.29 | 172.98 ± 52.06 | 157.80 ± 58.62 | 158.87 ± 57.76 | 160.80 ± 57.67 | 163.40 ± 56.27 | 167.60 ± 58.49 |
| 06 | Sample 2 (Spray-dried sap) (GHA I 59) | 2.2 | 196.00 ± 53.09 | 190.27 ± 27.76 | 190.27 ± 29.54 | 192.60 ± 29.09 | 194.73 ± 29.68 | 196.97 ± 29.04 | 198.60 ± 30.16 |
| 07 | Sample 2 (Spray-dried sap) (GHA I 59) | 8.6 | 231.30 ± 61.91 | 177.27 ± 24.48 | 176.17 ± 23.79 | 180.67 ± 25.04 | 182.03 ± 25.31 | 185.10 ± 24.60 | 169.73 ± 23.56 |
| 08 | Spray-dried sap (GHA I 59) | 35 | 167.48 ± 36.75 | 164.90 ± 22.54 | 166.63 ± 23.08 | 166.43 ± 22.66 | 171.67 ± 24.42 | 174.90 ± 25.70 | 178.57 ± 23.56 |
| 09 | Elga Option 4 purified water (control) | — | 165.50 ± 49.27 | 193.73 ± 22.37 | 196.67 ± 21.88 | 198.07 ± 21.02 | 199.83 ± 20.21 | 204.93 ± 18.65 | 207.13 ± 18.22 |

TABLE 1

HISTOLOGICAL EVALUATION
OF LIVER SECTIONS FROM MALE RATS
Sample 1

| | Animal no | Hepatic lesions | | |
|---|---|---|---|---|
| | GROUP 1: 100 mg/kg Sample 1 | | | |
| Day 7 | 01 | NPL | | |
| | 02 | NPL | | |
| | 03 | NPL | C1+ | |
| Day 13 | 04 | NPL | | MLC |
| | 05 | | FHS1+ | |
| | 06 | NPL | | |
| | GROUP 2: 400 mg/kg Sample 1 | | | |
| | 07 | | FHS1+ | |
| | 08 | NPL | C1+ | |
| | 09 | NPL | | |
| Day 13 | 10 | | DHS1+ | |
| | 11 | NPL | | |
| | 12 | | DHS1+ | |
| | GROUP 3: 1600 mg/kg Sample 1 | | | |
| Day 7 | 13 | NPL | | |
| | 14 | NPL | | |
| | 15 | NPL | | |
| Day 13 | 16 | NPL | | |
| | 17 | | DHS1+ | |
| | 18 | NPL | | |
| | GROUP 4: 3200 mg/kg Sample 1 | | | |
| | 19 | NPL | | |
| | 20 | NPL | | |
| | 21 | NPL | | |
| Day 13 | 22 | | DHS1+ | |
| | 23 | | FHS1+ | |
| | 24 | NPL | | |
| | GROUP 5: CONTROL: ELGA OPTION 4 PURIFIED WATER: RESTRICTED FOOD INTAKE | | | |
| | GROUP 5: CONTROL: Elga option purified water | | | |
| Day 7 | 25 | NPL | MLC | |
| | 26 | NPL | | |

TABLE 1-continued

HISTOLOGICAL EVALUATION
OF LIVER SECTIONS FROM MALE RATS
Sample 1

| | Animal no | Hepatic lesions | |
|---|---|---|---|
| Day 13 | 27 | NPL | |
| | 28 | | DHS1+ |
| | 29 | | DHS1+ |
| | 30 | NPL | |

Legend:
C = Congestion
DHS = Diffuse hydropic cell swelling
FHS = Focal hydropic cell swelling
NPL = No parenchymal fesions
MLC = Minimal lymphocytic cuffing
1+ = mild
2+ = moderate
3+ = severe

TABLE 2

HISTOLOGICAL EVALUATION
OF LIVER SECTIONS FROM MALE RATS
Sample 2

| | Animal no | Hepatic lesions | | |
|---|---|---|---|---|
| GROUP 6: 2.2 mg/kg Sample 2 | | | | |
| Day 7 | 31 | NPL | | |
| | 32 | NPL | MLC | |
| | 33 | | | FHS1+ |
| Day 13 | 34 | NPL | | |
| | 35 | | | DHS1+ |
| | 36 | NPL | | |
| GROUP 7: 8.8 mg/kg Sample 2 | | | | |
| | 37 | NPL | | |
| | 36 | NPL | | |
| | 39 | NPL | C1+ | |
| Day 13 | 40 | | | DHS1+ |
| | 41 | NPL | | |
| | 42 | | MLC | FHS1+ |
| GROUP 8: 35 mg/kg Sample 2 | | | | |
| Day 7 | 43 | NPL | | |
| | 44 | NPL | | |
| | 45 | NPL | | |
| Day 13 | 46 | NPL | | |
| | 47 | NPL | C1+ | |
| | 48 | | MLC | FHS1+ |
| GROUP 9 CONTROL: ELGA OPTION 4 PURIFIED WATER | | | | |
| GROUP 9: Control: Elga option 4 purified water | | | | |
| Day 7 | 49 | NPL | | |
| | 50 | NPL | | |
| | 51 | | | FHS1+ |
| Day 13 | 52 | | | DHS1+ |
| | 63 | NPL | | |
| | 54 | | | FHS1+ |

Legend:
C = Congestion
DHS = Diffuse hydropic cell swelling
FHS = Focal hydropic cell swelling
NPL = No parenchymal fesions
MLC = Minimal lymphocytic cuffing
1+ = mild
2+ = moderate
3+ = severe No specific lesions were recorded in the liver sections from the experimental rats which received the frozen sap as well as the spray-dried sap that could be attributed to the oral adminstration of the abovementioned chemicals. The hydropic cell swelling recorded in both control and experimental rats may indicate normal metabolic cell swelling and anoxic changes. Minimal foci of lymphocytic perivascular cuffing were found in some animals and is most likely an incidental observation. In a few rats congestion of mild degree is present in the hepatic sinusoids and should be regarded as an incidental observation.

An important feature of the invention shown by the results of this study is that no tolerance to any of the samples developed over the test period. This may provide considerable benefit, particularly in relation to the use of the compounds and compositions of the invention in the treatment of obesity.

While the compounds and compositions of the invention have primarily been described in relation to their properties as appetite suppressants, it should be noted that this expression—"appetite suppressant"—is used herein to denote activity which tends to limit appetite and/or increase the sense of satiety, and thus tends to reduce total calorific intake; this in turn tends to counteract obesity. Accordingly, this invention extends to a method of treating, preventing or combating obesity in a human or non-human animal which comprises administering to said human or non-human animal an obesity treating, preventing or combating amount of a compound of formula (2). A preferred embodiment of this aspect of the invention utilises a composition or extract containing a compound of formula (1).

The term "animal" as used herein extends to, but is not restricted to, companion animals, e.g. household pets and domesticated animals; non-limiting examples of such animals include cattle, sheep, ferrets, swine, camels, horses, poultry, fish, rabbits, goats, dogs and cats.

As an anorectic agent or in the treatment or prevention of obesity in a human, a compound of formula (2), preferably of formula (1), or the composition defined in any one of claims 9 and 25–31 hereafter, is advantageously administered to said human in a dosage amount of from about 0.01 mg/kg/day to about 10 mg/kg/day. A preferred dosage range is 0.05 mg/kg/day to 0.5 mg/kg/day. When using the spray dried powder form of the extract of this invention, a preferred dosage range is 0.1 mg/kg/day to 20 mg/kg/day; especially preferred is 0.5 mg/kg/day to 5 mg/kg/day.

What is claimed is:

1. An extract obtainable from a plant of the genus Trichocaulon or of the genus Hoodia which comprises an appetite suppressant agent having the formula

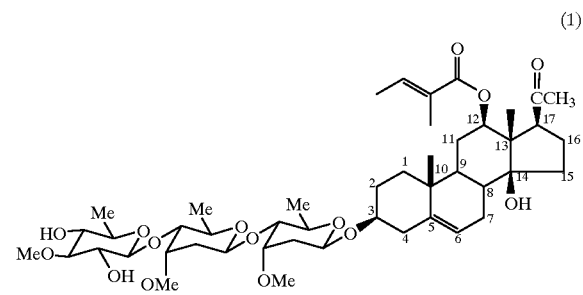

(1)

2. An extract as claimed in claim 2 wherein the plant of the genus Trichocaulon is selected from the species *Trichocaulon piliferum* and *Trichocaulon officinale* and the plant of the genus Hoodia is selected from the species *Hoodia curroii*, *Hoodia gordonii* and *Hoodia lugardii*.

3. An extract as claimed in claim 2 wherein substantially all the non-active impurities have been removed.

4. An extract as claimed in claim 1 which has been processed to a free-flowing powder.

5. A composition having appetite suppressant activity comprising the extract as claimed in claim 1.

6. A composition as claimed in claim 5 when admixed with a pharmaceutical excipient, diluent or carrier.

7. A composition as claimed in claim 5, which is prepared in unit dosage form.

8. The use of an extract as claimed in claim 1 in the manufacture of a medicament having appetite suppressant activity.

9. An extract as claimed in claim 1 for use as a medicament having appetite suppressant activity.

10. A method of combating obesity in a human or animal comprising administering to said human or animal an obesity combating amount of an extract as claimed in claim 1.

11. A compound having the structural formula:

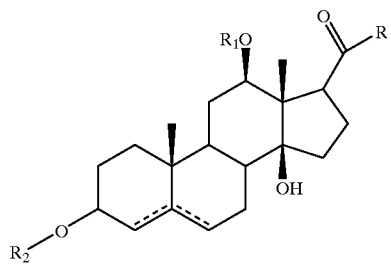

(2)

in which R=alkyl;
R$_1$=H, alkyl, tigloyl, benzoyl, or any other organic ester group;
R$_2$=H, or one or more 6-deoxy carbohydrates, or one or more 2,6-dideoxy carbohydrates, or glucose molecules, or combinations thereof;
and in which the broken lines indicate the optional presence of a further bond between C4–C5 or C5–C6.

12. A compound as claimed in claim 11 wherein there is a bond between C5–C6, R=methyl, R$_1$=tigloyl, R$_2$=3-0-[-β-D-thevetopyranosyl-(1→4)-β-D-cymaropyranosyl-(1→4)-β-D-cymaropyranosyl], the compound having the structural formula

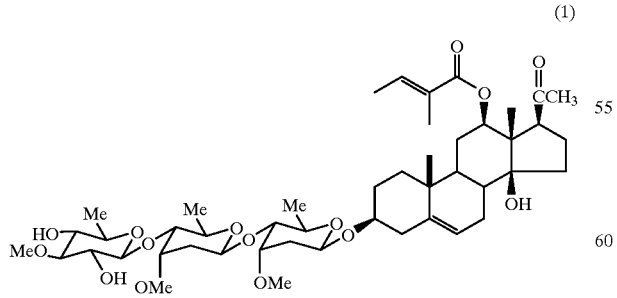

(1)

13. A process of forming a trisaccharide and coupling the resultant trisaccharide to a steroid intermediate, which includes the steps of i) coupling a selectively protected cymarose moiety of formula (40) and compound (45) using tin (II) chloride, AgOTf, Cp$_2$ZrCl$_2$ to produce a compound of the formula

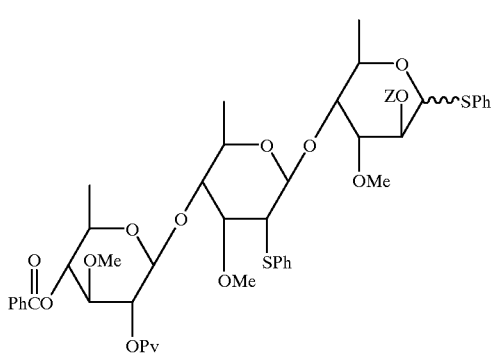

(57)

in which Z=TBDMS=t-butyldimethylsilyl;

ii) treating compound (57) with tetrabutylammonium fluoride and diethylaminosulphur trifluoride to produce a trisaccharide compound having the formula

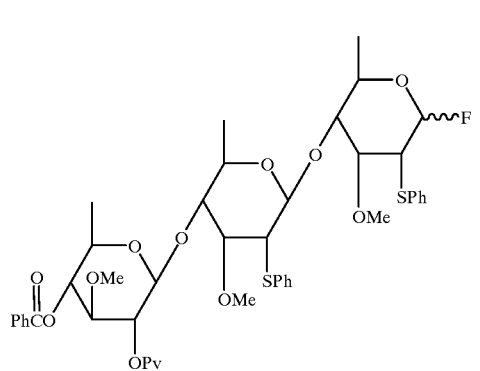

(58)

and iii) coupling the trisaccharide of formula (58) with a steroid intermediate of the formula

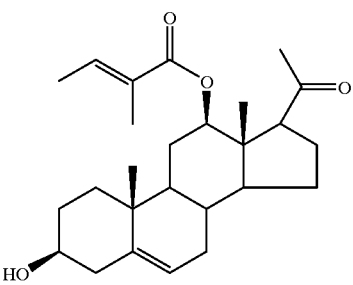

(59)

using tin (II) chloride, AgOTf, Cp$_2$ZrCl$_2$ to produce compound (1) as claimed in claim 12.

14. A composition having appetite suppressant activity comprising a compound as claimed in claim 11.

15. A composition as claimed in claim 14 wherein the compound is the compound of formula (1).

16. A composition as claimed in claim 14 when admixed with a pharmaceutical excipient, diluent or carrier.

17. A composition as claimed in claim 14, which is prepared in unit dosage form.

18. The use of a compound as claimed in claim 11 in the manufacture of a medicament having appetite suppressant activity.

19. The use as claimed in claim 18 of a compound of formula (1).

20. A compound as claimed in claim 11 for use as a medicament having appetite suppressant activity.

21. A compound claim 20 which is the compound of formula (1).

22. A foodstuff or beverage comprising an effective quantity of a compound as claimed in claim 11 to have an appetite suppressant effect when ingested.

23. A foodstuff or beverage as claimed in claim 22 wherein the compound is the compound of formula (1).

24. A compound of formula (1) as claimed in claim 11 isolated from a plant of the genus Trichocaulon or from the genus Hoodia for use as a medicament having appetite suppressant activity.

25. A compound as claimed in claim 24 wherein the compound is isolated from a plant of the species *Trichocaulon piliferum* or *Trichocaulon officinale* of from *Hoodia currorii*, *Hoodia gordonii* or *Hoodia lugardii*.

26. A compound of claim 11, wherein $R_1$ is tigloyl.

27. A compound of claim 11 having the following stereochemical structure:

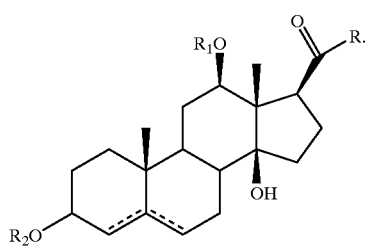

28. A compound having the structural formula

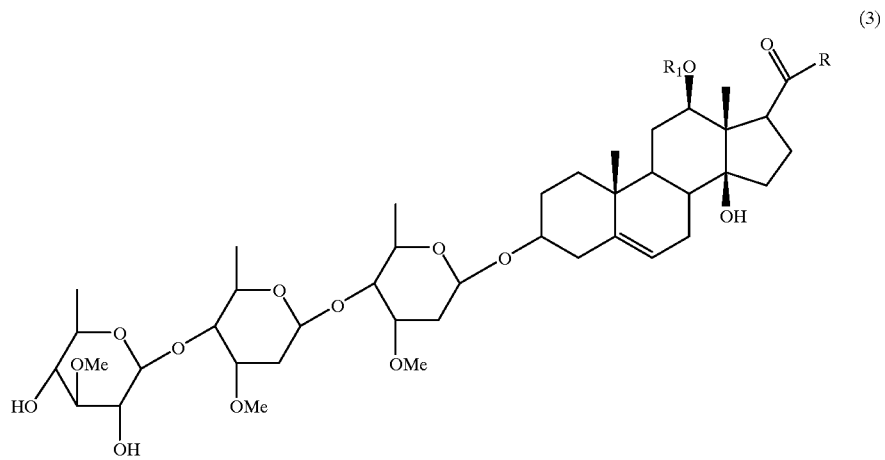

(3)

in which R=alkyl; and $R_1$=H, alkyl, tigloyl, benzoyl, or any other organic ester group.

29. A compound of claim 28, wherein $R_1$ is tigloyl.

30. A compound of claim 28 having the following stereochemical structure:

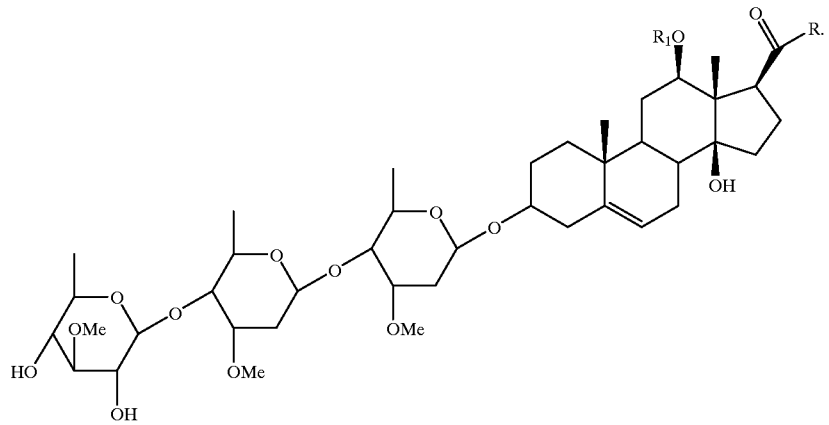

31. A compound having the structural formula:
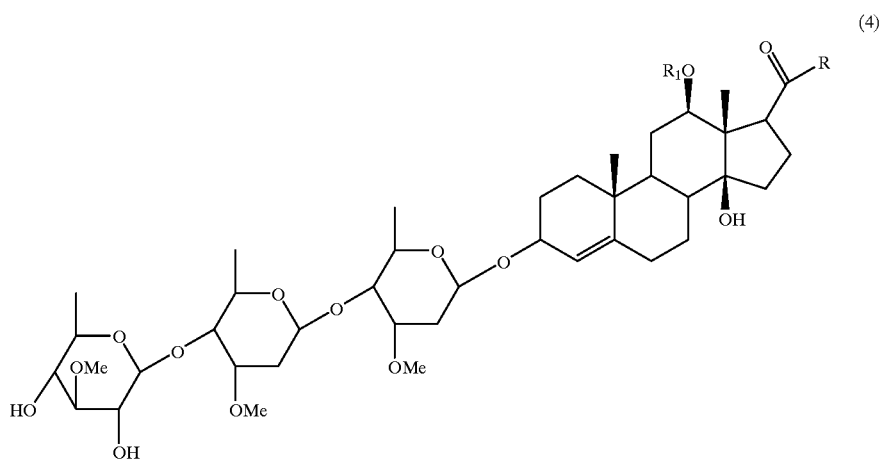
(4)
in which R=alkyl; and
R₁=H, alkyl, tigloyl, benzoyl, or any other organic ester group.
32. A compound of claim 31, wherein $R_1$ is tigloyl.
33. A compound of claim 31, having the following stereochemical structure:
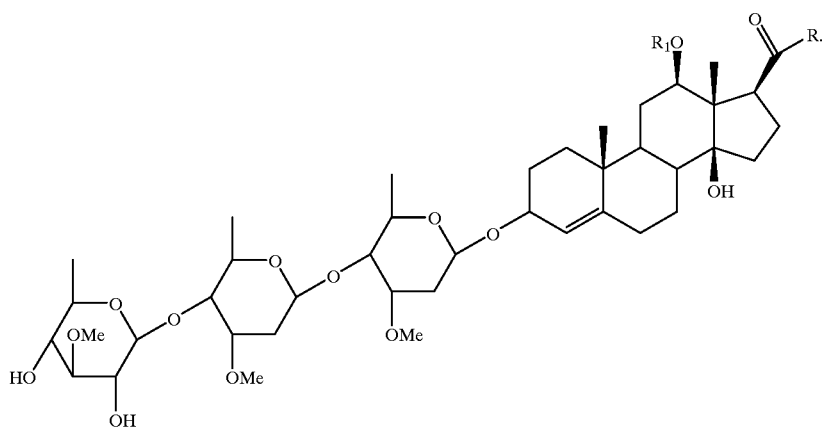
34. A compound having the structural formula:
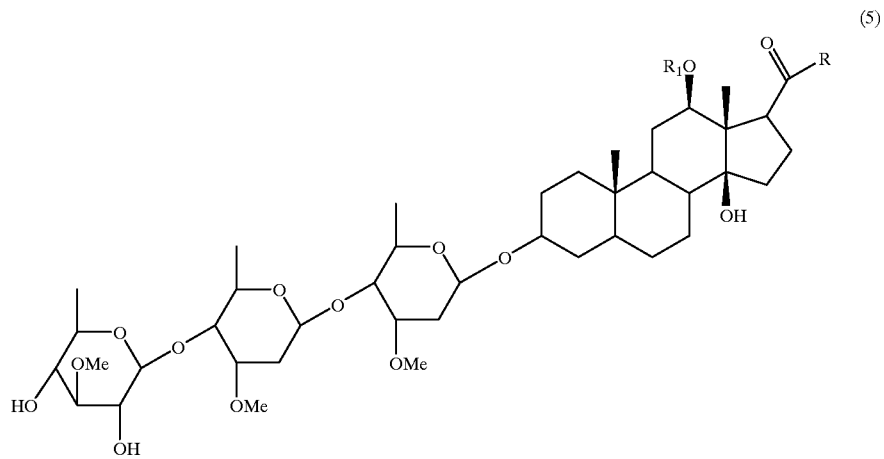
(5)

in which R=alkyl; and

R₁=H, alkyl, tigloyl, benzoyl, or any other organic ester group.

35. A compound of claim 34, wherein $R_1$ is tigloyl.

36. A compound of claim 34 having the following stereochemical structure:

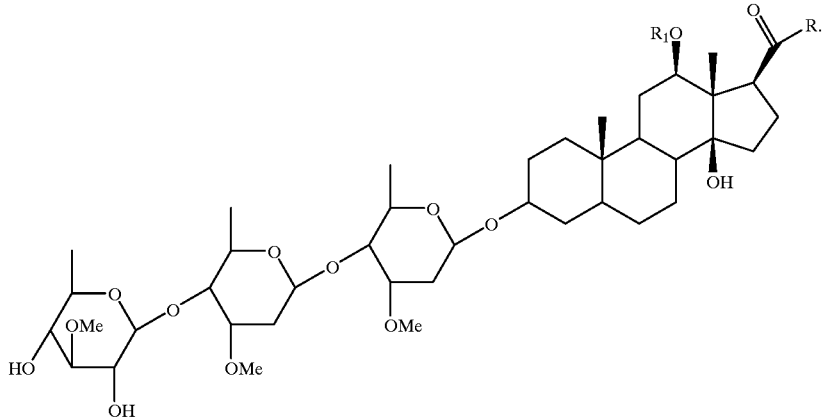

37. A compound having the structural formula:

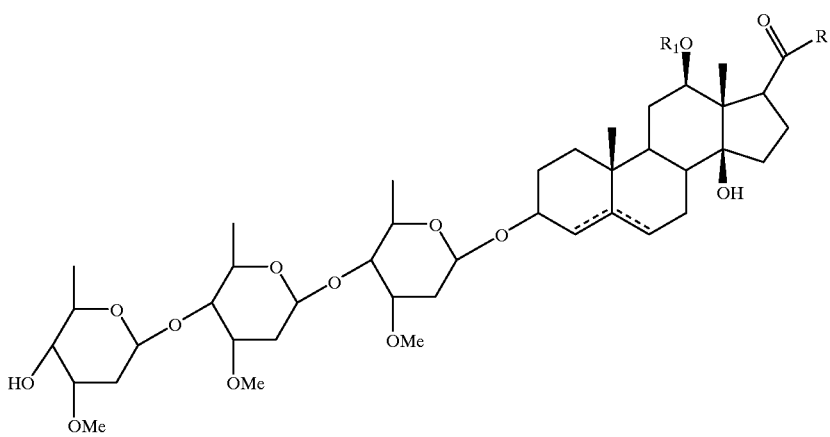

(6)

in which R=alkyl; and

R₁=H, alkyl, tigloyl, benzoyl, or any other organic ester group.

38. A compound of claim 37, wherein $R_1$ is tigloyl.

39. A compound of claim 37 having the following stereochemical structure:

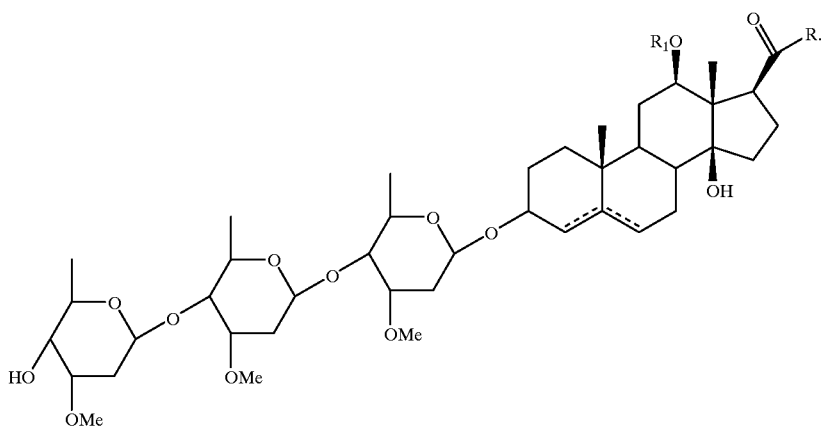

40. A compound having the structural formula:

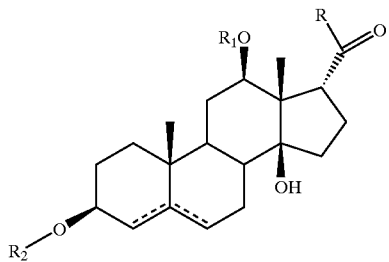

(8)

in which R=alkyl;
R₁=H, alkyl, tigloyl, benzoyl, or any other organic ester group;
R₂=H, or one or more 6-deoxy carbohydrates, or one or more 2,6-dideoxy carbohydrates, or glucose molecules, or combinations thereof;
and in which the broken lines indicate the optional presence of a further bond between C4–C5 or C5–C6.

41. A compound having the structural formula:

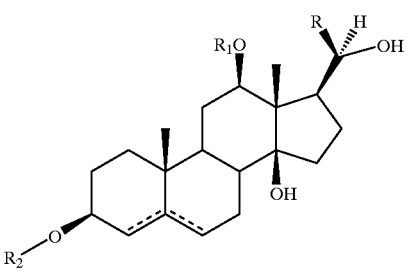

(9)

in which R=alkyl;
R₁=H, alkyl, tigloyl, benzoyl, or any other organic ester group;
R₂=H, or one or more 6-deoxy carbohydrates, or one or more 2, 6-dideoxy carbohydrates, or glucose molecules, or combinations thereof;
and in which the broken lines indicate the optional presence of a further bond between C4–C5 or C5–C6.

42. A compound having the structural formula:

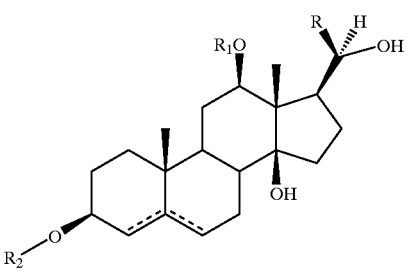

(10)

in which R=alkyl;
R₁=H, alkyl, tigloyl, benzoyl, or any other organic ester group; and
R₂=H, or one or more 6-deoxy carbohydrates, or one or more 2,6-dideoxy carbohydrates, or glucose molecules, or combinations thereof;

and in which the broken lines indicate the optional presence of a further bond between C4–C5 or C5–C6.

43. A compound having the structural formula:

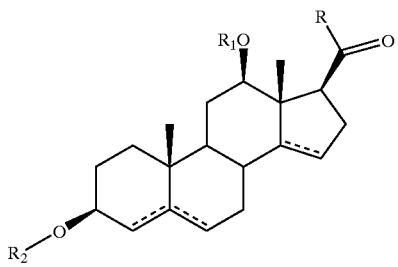

(11)

in which R=alkyl;
R₁=H, alkyl, tigloyl, benzoyl, or any other organic ester group; and
R₂=H, or one or more 6-deoxy carbohydrates, or one or more 2,6-dideoxy carbohydrates, or glucose molecules, or combinations thereof;
and in which the broken lines indicate the optional presence of a further bond between C4–C5, C5–C6 or C14–C15.

44. A compound having the structural formula:

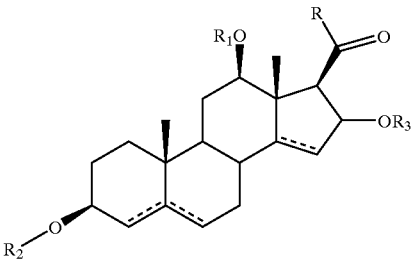

(12)

in which R=alkyl;
R₁=H, alkyl, tigloyl, benzoyl, or any other organic ester group; and
R₂=H, or one or more 6-deoxy carbohydrates, or one or more 2,6-dideoxy carbohydrates, or glucose molecules, or combinations thereof;
and in which the broken lines indicate the optional presence of a further bond between C4–C5, C5–C6 or C14–C15.

45. A compound having the structural formula:

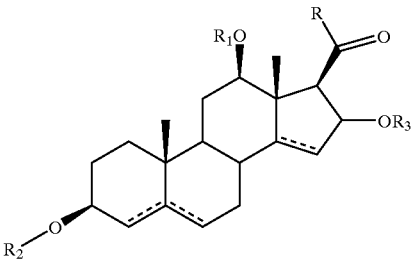

(13)

in which R=alkyl;
R₁=H, alkyl, tigloyl, benzoyl, or any other organic ester group;

$R_2$=H, or one or more 6-deoxy carbohydrates, or one or more 2,6-dideoxy carbohydrates, or glucose molecules, or combinations thereof;

and in which the broken lines indicate the optional presence of a further bond between C4–C5, C5–C6 or C14–C15; and $R_3$=H, alkyl, aryl, acyl, or glucoxy.

46. A compound having the structural formula:

(14)

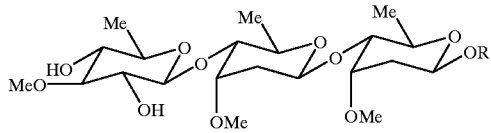

in which R=H, alkyl, aryl, or any steroid possessing a C14 beta hydroxy group, a C12 beta hydroxy functionality, a C17 acyl group, a C5–C6 olefin, or combinations thereof.

47. A process of coupling a monosaccharide cymarose to a steroid intermediate, which includes the steps of i) reacting a cymarose moiety of formula (38) with a steroid intermediate of formula (15) in the presence of tin chloride in a solvent to produce a compound 3-O-[4-O-benzoyl-2-phenylthio-β-D-cymaropyranosyl]-12,14-β-dihydroxy-pregnan-5-ene-20-one of the formula (51)

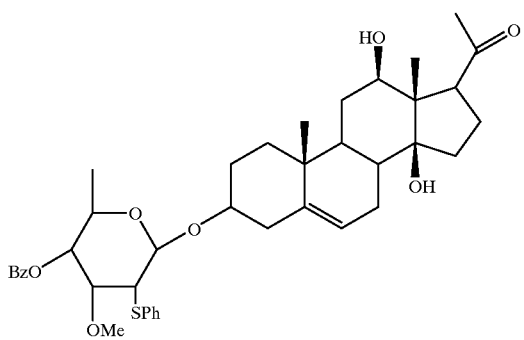

and (ii) treating the compound (51) with tiglic acid chloride in pyridine and thereafter with a base to produce a compound 3-O-[4-O-benzoyl-2-phenylthio-β-D-cymaropyranosyl]-12β-tigloyl-14β-hydroxy-pregnan-5-ene-20-one of the formula (52)

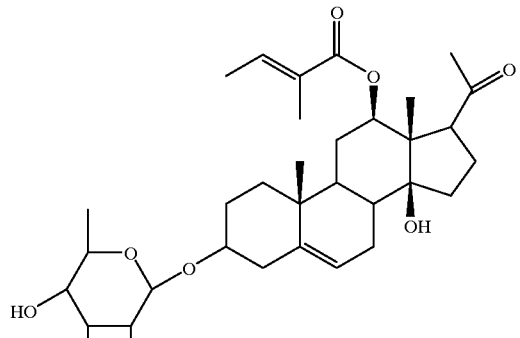

48. A compound of formula (52) when produced by a process as claimed in claim 47.

49. A process of coupling a monosaccharide cymarose moiety to a monosaccharide thevetose moiety and coupling the resultant disaccharide to the compound of formula (52) as claimed in claim 48 which includes the steps of i) coupling a selectively protected cymarose moiety of formula (40) and a monosaccharide thevetose moiety of formula (50 A) using tin chloride (SnCl$_2$) and silver trifluoromethanesulphonate to produce a compound of the formula (53)

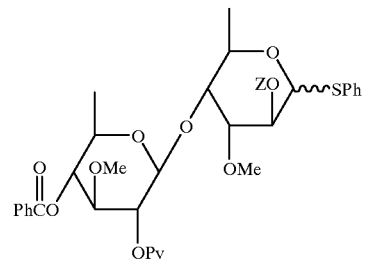

in which Z=TBDMS=t-butyldimethylsilyl ii) treating compound (53) with tetrabutylamtnoniumfluoride to produce a compound of the formula (54)

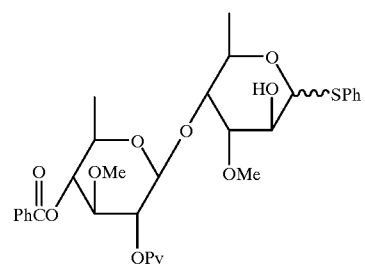

iii) treating compound (54) with diethylaminosulphur trifluoride to produce a compound of the formula

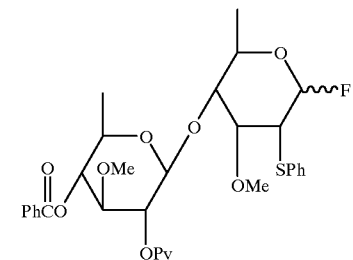

(55)

iv) reacting compound (55) with compound (52) as claimed in claim 48 to produce a compound of the formula

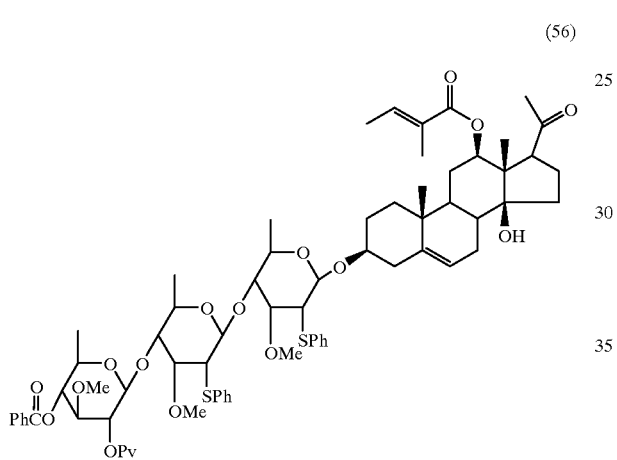

(56)

and (v) treating compound (56) in a Raney-Nickel reaction and thereafter with a base to produce compound (1) as claimed in claim 12.

50. A composition having appetite suppressant activity comprising a compound of formula (1) isolated from a plant of the genus Trichocaulon or of the genus Hoodia.

51. A composition as claimed in claim 50 wherein the compound is isolated and/or purified from a plant of the species *Trichocaulon piliferum* or *Trichocaulon officinale* or from of the species *Hoodia currorii, Hoodia gordonii* or *Hoodia lugardii*.

52. A composition as claimed in claim 50 wherein the compound is isolated and/or purified from an extract derived from a plant of the species *Trichocaulon piliferum, Trichocaulon officinale* or from a plant of the species *Hoodia currorii, Hoodia gordonii* or *Hoodia lugardii*.

53. A composition as claimed in claim 50, when admixed with a pharmaceutical excipient, diluent or carrier.

54. A composition as claimed in claim 53 which is prepared in unit dosage form.

55. A compound having the structural formula

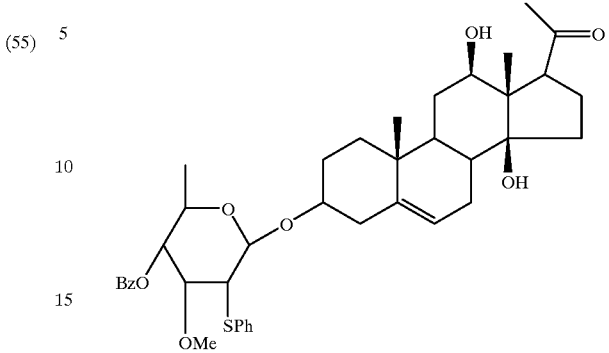

(51)

56. A compound having the structural formula

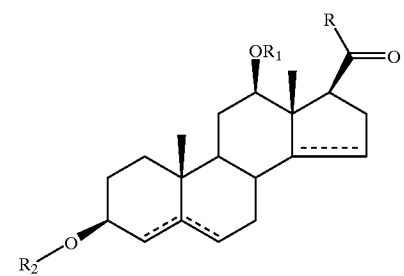

(12)

57. A compound having the structural formula

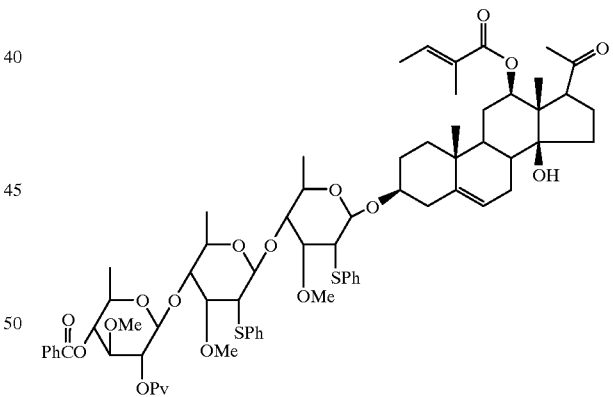

(56)

58. A structure of the formula 3-O-β-D-theverosyl-(1→4)-p-D-cymaropyranosyl-(1→4)-β-D-cymaropyranoside-12β-O-tigloyl-14β-hydroxy-pregnane-5-ene-20-one.

* * * * *

UNITED STATES PATENT AND TRADEMARK OFFICE
CERTIFICATE OF CORRECTION

PATENT NO. : 6,376,657 B1  Page 1 of 1
DATED : April 23, 2002
INVENTOR(S) : Fanie Retief Van Heerden et al.

It is certified that error appears in the above-identified patent and that said Letters Patent is hereby corrected as shown below:

Column 70,
Lines 45-46 and 64, delete "Trichocaulon" and insert -- *Trichocaulon* --
Lines 46 and 66, delete "Hoodia" and insert -- *Hoodia* --

Column 73,
Line 8, insert -- as claimed in -- between "compound" and "claim"
Line 16, delete "Trichocaulon" and insert -- *Trichocaulon* --
Line 17, delete "Hoodia" and insert -- *Hoodia* --

Column 82,
Lines 48-49, delete "tetabutylamtnoniumfluoride" and insert
-- tetrabutylammoniumfluoride --

Column 83,
Line 46, delete "Trichocaulon" and insert -- *Trichocaulon* --
Line 46, delete "Hoodia" and insert -- *Hoodia* --

Signed and Sealed this

Ninth Day of March, 2004

JON W. DUDAS
*Acting Director of the United States Patent and Trademark Office*